(12) United States Patent
Gorin et al.

(10) Patent No.: US 8,053,190 B2
(45) Date of Patent: Nov. 8, 2011

(54) SUSCEPTIBILITY GENES FOR AGE-RELATED MACULOPATHY (ARM) ON CHROMOSOME 10Q26

(75) Inventors: Michael B. Gorin, Pittsburgh, PA (US); Johanna Jakobsdottir, Pittsburgh, PA (US); Yvette P. Conley, White Oak, PA (US); Daniel E. Weeks, Pittsburgh, PA (US); Tammy S. Mah-Fraser, Edmonton (CA); Robert E. Ferrell, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 141 days.

(21) Appl. No.: 12/701,098

(22) Filed: Feb. 5, 2010

(65) Prior Publication Data

US 2010/0216149 A1 Aug. 26, 2010

Related U.S. Application Data

(63) Continuation of application No. 11/448,267, filed on Jun. 7, 2006, now Pat. No. 7,695,909.

(60) Provisional application No. 60/688,572, filed on Jun. 8, 2005.

(51) Int. Cl.
*C12P 19/34* (2006.01)
*C12Q 1/66* (2006.01)

(52) U.S. Cl. .................. 435/6.11; 435/6.12; 436/63

(58) Field of Classification Search .................. None
See application file for complete search history.

(56) References Cited

U.S. PATENT DOCUMENTS

| | | | |
|---|---|---|---|
| 6,417,342 B1 | 7/2002 | Stone et al. | |
| 6,593,104 B1 | 7/2003 | Stone et al. | |
| 7,695,909 B2 | 4/2010 | Gorin et al. | |
| 2003/0017501 A1 | 1/2003 | Hageman et al. | |
| 2003/0138798 A1 | 7/2003 | Stone et al. | |
| 2004/0265924 A1 | 12/2004 | Hollyfield et al. | |
| 2005/0059010 A1 | 3/2005 | Stone et al. | |

OTHER PUBLICATIONS

Abecasis et al. (2004) Age-related macular degeneration: a high-resolution genome scan for susceptibility Loci in a population enriched for late-stage disease. Am J Hum Genet 74:482-494.
Abecasis GR, et al. (2000) MERLIN—Multipoint Engine for Rapid Likelihood Inference. Am J Hum Genet 67 (Suppl 2): 327, 50th Annual Meeting of Am Soc Hum Genet, Oct. 3-6, 2000, Abstract 1816.
Age-Related Eye Disease Study Research Group (1999) The Age-Related Eye Disease Study (AREDS): design implications. AREDS report No. 1. Control Clin Trials. 20, 573-600.
Age-Related Eye Disease Study Research Group (2000) Risk factors associated with age-related macular degeneration. A case-control . . . : AREDS Report No. 3. Ophthalmology. 107, 2224-2232.
Ayyagari, et al. (2001) Evaluation of the ELOVL4 gene in patients with age-related macular degeneration. Opthalmic Genet. 22, 233-239.
Baird, P.N., et al. (2004) The epsilon2 and epsilon4 alleles of the apolipoprotein gene are associated with age-related macular degeneration. Invest Ophthalmol Vis Sci. 45, 1311-1315.
Barrett et al. (2005) Haploview: analysis and visualization of LD and haplotype maps. Bioinformatics 21:263-265.
Browning SR, et al. (2005) Case-control single-marker and haplotypic association analysis of pedigree data. Genet Epidemiol 28:110-122.
Conley, Y.P., et al. (2005) Candidate gene analysis suggests a role for fatty acid biosynthesis and regulation of the complement system in the etiology . . . Hum Mol Genet. 14, 1991-2002.
Cordell et al (2005) Genetic association studies. Lancet. 366,1121-1131.
De Luca et al. (2004) Pattern of expression of HtrA1 during mouse development. J Histochem Cytochem 2:1609-1617.
DerSimonian, R. and Laird, N. (1986) Meta-analysis in clinical trials. Control Clin Trials. 7, 177-188.
Dowler et al. (2000) Identification of pleckstrin-homology-domain-containing proteins with novel phosphoinositide-binding specificities. Biochem J 351:19-31.
Edwards et al. (2005) Complement Factor H Polymorphism and Age-Related Macular Degeneration. Science 308, 421-424.
Esparza-Gordillo et al. (2004) Genetic and environmental factors influencing the human factor H plasma levels. Immunogenetics 56:77-82.
Fan and Malik (2003) Toll-like receptor-4 (TLR4) signaling augments chemokine-induced neutrophil migration by modulating cell surface expression of chemokine receptors. Nat Med 9:315-321.
Fisher et al. (2005) Meta-analysis of genome scans of age-related macular degeneration. Hum Mol Genet. 14(15):2257-64.
Fried et al. (1991) The Cardiovascular Health Study: design and rationale. Ann Epidemiol. 1, 263-276.
Gauderman, W.J. and Morrison, J.M. (2006) QUANTO 1.1: A computer program for power and sample size calculations for genetic-epidemiology studies, http://hydra.usc.edu/gxe).
GenBank Accession No. NM_002775. NCBI Database, National Center for Biotechnology Information, NIH (Bethesda, MD, USA), Dec. 3, 2006.
GenBank Accession No. NM_002925. NCBI Database, National Center for Biotechnology Information, NIH (Bethesda, MD, USA), Nov. 18, 2006.
GenBank Accession No. NM_005308. NCBI Database, National Center for Biotechnology Information, NIH (Bethesda, MD, USA), Dec. 3, 2006.
GenBank Accession No. NM_021662. NCBI Database, National Center for Biotechnology Information, NIH (Bethesda, MD, USA), Nov. 18, 2006.
GenBank Accession No. NM_001001974. NCBI Database, National Center for Biotechnology Information, NIH (Bethesda, MD, USA), Nov. 18, 2006.
GenBank Accession No. NM_001005339. NCBI Database, National Center for Biotechnology Information, NIH (Bethesda, MD, USA), Nov. 18, 2006.

(Continued)

*Primary Examiner* — Sarae Bausch
(74) *Attorney, Agent, or Firm* — The Webb Law Firm

(57) ABSTRACT

Allelic variations in the genes PLEKHA1 and LOC387715 are identified herein as risk factor for Age Related Maculopathy (ARM). A method is therefore provided for identifying a risk of development of ARM in an individual that comprises identification of allelic variations in PLEKHA1 and/or LOC387715. Related apparatus, such as an array, are identified as being useful in implementing those methods.

6 Claims, 32 Drawing Sheets

OTHER PUBLICATIONS

GenBank Accession No. NP_002766. NCBI Database, National Center for Biotechnology Information, NIH (Bethesda, MD, USA), Dec. 3, 2006.
GenBank Accession No. NP_005299. NCBI Database, National Center for Biotechnology Information, NIH (Bethesda, MD, USA), Dec. 3, 2006.
GenBank Accession No. NP_067635. NCBI Database, National Center for Biotechnology Information, NIH (Bethesda, MD, USA), Nov. 18, 2006.
GenBank Accession No. NP_001001974. NCBI Database, National Center for Biotechnology Information, NIH (Bethesda, MD, USA), Nov. 18, 2006.
GenBank Accession No. XM_373477. NCBI Database, National Center for Biotechnology Information, NIH (Bethesda, MD, USA), Aug. 20, 2004.
Gudbjartsson et al. (2000) Allegro, a new computer program for multipoint linkage analysis. Nat Genet 25:12-13.
Hageman and Mullins (1999) Molecular composition of drusen as related to substructural phenotype. Molecular Vision 5:28.
Hageman, G.S. et al. (2005) From the Cover: A common haplotype in the complement regulatory gene factor H (HF1/CFH) . . . Proc Natl Acad Sci U S A 102:7227-7232.
Hageman et al. (2001) An integrated hypothesis that considers drusen as biomarkers of immune-mediated processes . . . Progress in Retinal & Eye Research 20:705-732.
Haines, J.L., et al. (2005) Complement factor H variant increases the risk of age-related macular degeneration. Science. 308, 419-421.
Haribabu and Snyderman (1993) Identification of additional members of human G-protein-coupled receptor kinase multigene family. Proc Natl Acad Sci U S A 90:9398-9402.
Hollborn et al (2004) Contrary effects of cytokines on mRNAs of cell cycle- and ECM-related proteins in hRPE cells in vitro. Curr Eye Res 28:215-223.
Howson et al. (2005) Comparison of population- and family-based methods for genetic association analysis in the presence of interacting loci. Genet Epidemiol. 29, 51-67.
Huang et al. (2004) Ignoring linkage disequilibrium among tightly linked markers induces false-positive evidence of linkage for affected sib pair analysis. Am J Hum Genet 75:1106-11.
Iyengar et al. (2004) Dissection of genomewide-scan data in extended families reveals a major locus and oligogenic susceptibility for age-related macular degeneration. Am J Hum Genet 74:20-39.
Jakobsdottir et al. (2005) Susceptibility genes for age-related maculopathy on chromosome 10q26. Am J Hum Genet. 77, 389-407.
Johnson et al. (2000) A potential role for immune complex pathogenesis in drusen formation. Experimental Eye Research 70:441-449.
Johnson LV, et al. (2001) Complement activation and inflammatory processes in Drusen formation and age related macular degeneration. Experimental Eye Research 73:887-89.
Kenealy et al. (2004) Linkage analysis for age-related macular degeneration supports a gene on chromosome 10q26. Mol Vis 10:57-61.
Klaver, C.C., et al. (1998) Genetic association of apolipoprotein E with age-related macular degeneration. Am J Hum Genet. 63, 200-206.
Klein et al. (1998) Age-related macular degeneration. Clinical features in a large family and linkage to chromosome 1q. Archives of Ophthalmology 116:1082-1088.
Klein, R., et al. (2003) Early age-related maculopathy in the cardiovascular health study. Ophthalmology. 110, 25-33.
Klein, R.J., et al. (2005) Complement factor H polymorphism in age-related macular degeneration. Science. 308, 385-389.
Kong et al. (2004) A combined linkage-physical map of the human genome. Am J Hum Genet 75:1143-1148.
Lange et al. (2001) MENDEL Version 4.0: A complete package for the exact genetic analysis of . . . Am J of Hum Genet 69 (Supplement):A1886, 51st Annual Meeting of ASHG, Abstract 1886.
Li C, et al. (2004) Assessing whether an allele can account in part for a linkage signal: the Genotype-IBD Sharing Test (GIST). Am J Hum Genet 74:418-431.
Lohmueller, K.E., et al. (2003) Meta-analysis of genetic association studies supports a contribution of common variants to susceptibility to common disease. Nat Genet. 33, 177-182.
Magnusson, K.P., et al. (2006) CFH Y402H confers similar risk of soft drusen and both forms of advanced AMD. PLoS Med. 3, e5.
Majewski et al. (2003) Age-related macular degeneration—a genome scan in extended families. Am J Hum Genet 73:540-550.
MIM No. 600870. Online Mendelian Inheritance in Man, OMIM (TM). Johns Hopkins University, Baltimore, MD. URL: http://www.ncbi.nlm.nih.gov/omim/. Last edited: Oct. 26, 2005.
MIM No. 602194. Online Mendelian Inheritance in Man, OMIM (TM). Johns Hopkins University, Baltimore, MD. URL: http://www.ncbi.nlm.nih.gov/omim/. Last edited: Nov. 17, 2006.
MIM No. 602856. Online Mendelian Inheritance in Man, OMIM (TM). Johns Hopkins University, Baltimore, MD. URL: http://www.ncbi.nlm.nih.gov/omim/. Last edited: Sep. 12, 2002.
MIM No. 607772. Online Mendelian Inheritance in Man, OMIM (TM). Johns Hopkins University, Baltimore, MD. URL: http://www.ncbi.nlm.nih.gov/omim/. Last edited: Sep. 6, 2005.
Moratz et al. (2004) Regulation of chemokine-induced lymphocyte migration by RGS proteins. Methods Enzymol 389:15-32.
Mukhopadhyay et al. (2004) Comparative study of multipoint methods for genotype error detection. Hum Hered 58:175-189.
Mukhopadhyay et al. (2005) Mega2: data-handling for facilitating genetic linkage and association analyses. Bioinformatics, 21(10): 2556-7.
Mullins et al. (2000) Drusen associated with aging and age-related macular degeneration contain proteins common to extracellular deposits . . . FASEB Journal 14:835-846.
Murwantoko et al. (2004) Binding of proteins to the PDZ domain regulates proteolytic activity of HtrA1 serine protease. Biochem J 381:895-904.
Normand, S.L. (1999) Meta-analysis: formulating, evaluating, combining, and reporting. Stat Med. 18, 321-359.
North et al. (2005) Application of logistic regression to case-control association studies involving two causative loci. Hum Hered 59:79-87.
O'Connell and Weeks (1998) PedCheck: A program for identifying genotype incompatibilities in linkage analysis. Am J Hum Genet 63:259-266.
Oka et al. (2004) HtrA1 serine protease inhibits signaling mediated by TGFfbeta family proteins. Development 131:1041-1053.
Okamoto et al (2006) Complement factor H polymorphisms in Japanese population with age-related macular degeneration. Mol Vis. 12, 156-158.
R Development Core Team (2004) R: A language and environment for statistical computing. R Foundation for Statistical Computing, Austria. ISBN 3-900051-07-0, URL: <http://www.r-project.org/>.
Rinaldo et al. (2005) Characterization of multilocus linkage disequilibrium. Genetic Epidemiology 28:193-206.
Risch et al. (2001) Implications of multilocus inheritance for gene-disease association studies. Theor Popul Biol. 60, 215-220.
Rivera, A., et al. (2005) Hypothetical LOC387715 is a second major susceptibility gene for age-related macular degeneration, contributing independently of . . . Hum Mol Genet. 14, 3227-3236.
Santangelo et al. (2005) A Discordant Sib-Pair Linkage Analysis of Age-Related Macular Degeneration. Ophthalmic Genetics 26:61-68.
Schaid et al. (2002) Caution on pedigree haplotype inference with software that assumes linkage equilibrium. Am J Hum Genet 71:992-995.
Schick et al. (2003) A whole-genome screen of a quantitative trait of age-related maculopathy in sibships from the Beaver Dam Eye Study. Am J Hum Genet 72:1412-1424.
Schmidt et al. (2004) Ordered subset linkage analysis supports a susceptibility locus for age-related macular degeneration on chromosome 16p12. BMC Genet 5:18.
Schmidt et al (2006) Cigarette smoking strongly modifies the association of LOC387715 and age-related macular degeneration Am J Hum Genet. 78, 852-864.
Schmidt, S., et al. (2000) Association of the apolipoprotein E gene with age-related macular degeneration: possible effect modification by family history, age, and gender. Mol Vis. 6, 287-293.

Schmidt, S., et al. (2002) A pooled case-control study of the apolipoprotein E (APOE) gene in age-related maculopathy. Ophthalmic Genet. 23, 209-223.

Seddon et al. (2003) A genomewide scan for age-related macular degeneration provides evidence for linkage to several chromosomal regions. Am J Hum Genet 73:780-790.

Sepp, T., et al. (2006) Complement factor H variant Y402H is a major risk determinant for geographic atrophy and choroidal neovascularization . . . Invest Ophthalmol Vis Sci. 47, 536-540.

Shi et al. (2004) Toll-like receptor signaling alters the expression of regulator of G protein signaling proteins in dendritic cells: implications for G protein-coupled . . . J Immunol 172:5175-5184.

Souied, E.H., et al. (2005) Y402H complement factor H polymorphism associated with exudative age-related macular degeneration in the French population. Mol Vis. 11, 1135-1140.

UniGene Hs.120359. NCBI Database, National Center for Biotechnology Information, NIH (Bethesda, MD, USA), printed May. 2005.

UniGene Hs.287830. NCBI Database National Center for Biotechnology Information, NIH (Bethesda, MD, USA), printed May 2005.

UniGene Hs.501200. NCBI Database, National Center for Biotechnology Information, NIH (Bethesda, MD, USA), printed May 2005.

UniGene Hs.501280. NCBI Database, National Center for Biotechnology Information, NIH (Bethesda, MD, USA), printed May 2005.

UniGene Hs.524625. NCBI Database, National Center for Biotechnology Information, NIH (Bethesda, MD, USA), Printed May 2005.

van Houwelingen, H.C., et al. (2002) Advanced methods in meta-analysis: multivariate approach and meta-regression. Stat Med. 21, 589-624.

van Leeuwen, R., et al. (2003) Epidemiology of age-related maculopathy: a review. Eur J Epidemiol. 18, 845-854.

Weeks et al. (2004) Age-related maculopathy: a genomewide scan with continued evidence of susceptibility loci within the 1q31, 10q26, and 17q25 regions. An J Hum Genet. 75, 174-189.

Weeks et al. (2000) A full genome scan for age-related maculopathy. Human Molecular Genetics 9:1329-1349.

Weeks, D.E., et al. (2001) Age-related maculopathy: an expanded genome-wide scan with evidence of susceptibility loci within the 1q31 and 17q25 regions. Am J Ophthalmol. 132, 682-692.

Zareparsi et al. (2005) Toll-like receptor 4 variant D299G is associated with susceptibility to age-related macular degeneration. Hum Mol Genet 12:1449-55.

Zareparsi, S., et al. (2004) Association of apolipoprotein E alleles with susceptibility to age-related macular degeneration in a large cohort . . . Invest Ophthalmol Vis Sci. 45, 1306-1310.

Zareparsi, S., et al. (2005) Strong association of the Y402H variant in complement factor H at 1q32 with susceptibility to age-related macular degeneration. Am J Hum Genet. 77, 149-153.

U.S. Appl. No. 11/448,267 (USPN 7,695,909), Excerpts from File History of parent patent application, 2009.

GeneCard for HSP12A, Heat Shock 70kDa, printed Aug. 18, 2008, available at www.genecards.org. pp. 1-13.

GeneCard for LOC387715, printed Aug. 18, 2008, available at www.genecards.org. pp. 1-12.

GeneCard for ARMS2, printed Aug. 18, 2008, available at www.genecards.org. pp. 1-12.

Ioannidis, JPA, PLoS Medicine (Aug. 2005) 2(8):696-701.

Hegele, RA, Arterioscler. Thromb. Vasc. Biol. 2002;22;1058-1061.

Kroese, M, Genet Med 2004:6(6):475-480.

Chromosome 10: 196 SNPs

Chromosome 10: 159 SNPs (H-clust 0.5)

Chromosome 1: 697 SNPs

LOC387715

```
  1 mlrlypgpmv teaegkggpe maslsssvvp vsfistlres vldpgvggeg asdkqrskls
 61 lshsmipaak ihtelclpaf fspagtqrrf qqpqhhltls iihtaar 1 gagatggcag ctggcttggc aaggggacag cacctttgtc accacattat gtccctgtac
 61 cctacatgct gcgcctatac ccaggaccga tggtaactga ggcggagggg aaaggagggc
121 ctgagatggc aagtctgtcc tcctcggtgg ttcctgtgtc cttcatttcc actctgcgag
181 agtctgtgct ggaccctgga gttggtggag aaggagccag tgacaagcag aggagcaaac
241 tgtctttatc acactccatg atcccagctg ctaaaatcca cactgagctc tgcttaccag
301 ccttcttctc tcctgctgga acccagagga ggttccagca gcctcagcac cacctgacac
361 tgtctatcat ccacactgca gcaaggtgat tctgccaaaa catatctcct taaaagccaa
421 ctggagcttc tcatcagcat caatgtgaag ccaaaaatcc ttaggaggac agagggagtc
481 cctcacaacc tagactggtc cccttccctc cagctgcctc aactgtccac aggactctct
541 tcccacctgc ggccacactg tgcaacctgg aatttcccca cctgggcgga ctcatcacgt
601 catcaccaat tggatgcatc ttctgctctg tgcagctggt gaaatctttc tcaacccttg
661 agatgcagcc caatcttctc ctaacatctg gattcctctc tgtcactgca ttccctcctg
721 tcatcctgcc tttgttttct tgccctcctt tctctcccgg gtgataggca ttaactaaaa
781 ttaaataaaa attcagatca tccttgca
```

Fig. 16

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Forward PCR primer for rs11538141

<400> SEQUENCE: 1
cagagtcgcc atgcagatcc          20

<210> SEQ ID NO 2
<211> LENGTH: 20
<212> TYPE: DNA
<213> ORGANISM: Artificial Sequence
<220> FEATURE:
<223> OTHER INFORMATION: Reverse PCR primer for rs11538141

<400> SEQUENCE: 2
cccgaagggc accacgcact          20

<210> SEQ ID NO 3
<211> LENGTH: 20
<212> TYPE: DNA
<213> ORGANISM: Artificial Sequence
<220> FEATURE:
<223> OTHER INFORMATION: Forward PCR Primer for rs2736911

<400> SEQUENCE: 3
gcacctttgt caccacatta          20

<210> SEQ ID NO 4
<211> LENGTH: 20
<212> TYPE: DNA
<213> ORGANISM: Artificial Sequence
<220> FEATURE:
<223> OTHER INFORMATION: Reverse PCR primer for rs2736911

<400> SEQUENCE: 4
gcctgatcat ctgcatttct          20

<210> SEQ ID NO 5
<211> LENGTH: 20
<212> TYPE: DNA
<213> ORGANISM: Artificial Sequence
<220> FEATURE:
<223> OTHER INFORMATION: Forward PCR Primer for rs10490923

<400> SEQUENCE: 5
gcacctttgt caccacatta          20

<210> SEQ ID NO 6
<211> LENGTH: 20
<212> TYPE: DNA
<213> ORGANISM: Artificial Sequence
<220> FEATURE:
<223> OTHER INFORMATION: Reverse PCR Primer for rs10490923

<400> SEQUENCE: 6
gcctgatcat ctgcatttct          20

<210> SEQ ID NO 7
<211> LENGTH: 20
<212> TYPE: DNA

```
<213> ORGANISM: Artificial Sequence
<220> FEATURE:
<223> OTHER INFORMATION: Forward PCR Primer for rs10490924

<400> SEQUENCE: 7
gcacctttgt caccacatta                                                  20

<210> SEQ ID NO 8
<211> LENGTH: 20
<212> TYPE: DNA
<213> ORGANISM: Artificial Sequence
<220> FEATURE:
<223> OTHER INFORMATION: Reverse PCR primer for rs10490924

<400> SEQUENCE: 8
gcctgatcat ctgcatttct                                                  20

<210> SEQ ID NO 9
<211> LENGTH: 20
<212> TYPE: DNA
<213> ORGANISM: Artificial Sequence
<220> FEATURE:
<223> OTHER INFORMATION: Forward PCR Primer for rs1803403

<400> SEQUENCE: 9
tgctgtccct ttgttgtctc                                                  20

<210> SEQ ID NO 10
<211> LENGTH: 20
<212> TYPE: DNA
<213> ORGANISM: Artificial Sequence
<220> FEATURE:
<223> OTHER INFORMATION: Reverse PCR primer for rs1803403

<400> SEQUENCE: 10
agacacagac acgcatcctg                                                  20

<210> SEQ ID NO 11
<211> LENGTH: 18
<212> TYPE: DNA
<213> ORGANISM: Artificial Sequence
<220> FEATURE:
<223> OTHER INFORMATION: Forward PCR primer for rs12258692

<400> SEQUENCE: 11
gccaggaaaa ggaacctc                                                    18

<210> SEQ ID NO 12
<211> LENGTH: 18
<212> TYPE: DNA
<213> ORGANISM: Artificial Sequence
<220> FEATURE:
<223> OTHER INFORMATION: Reverse PCR primer for rs12258692

<400> SEQUENCE: 12
gccaggcatc aagtcaga                                                    18

<210> SEQ ID NO 13
<211> LENGTH: 21
<212> TYPE: DNA
<213> ORGANISM: Artificial
<220> FEATURE:
<223> OTHER INFORMATION: Forward PCR Primer for ELOVL4

<400> SEQUENCE: 13
agatgccgat gttgttaaaa g                                                21
```

```
<210> SEQ ID NO 14
<211> LENGTH: 20
<212> TYPE: DNA
<213> ORGANISM: Artificial Sequence
<220> FEATURE:
<223> OTHER INFORMATION: Reverse PCR primer for ELOVL4

<400> SEQUENCE: 14
catctgggta tggtattaac                                                  20

<210> SEQ ID NO 15
<211> LENGTH: 24
<212> TYPE: DNA
<213> ORGANISM: Artificial Sequence
<220> FEATURE:
<223> OTHER INFORMATION: Forward PCR primer for CFH

<400> SEQUENCE: 15 tcttttgtg caaacctttg ttag                                              24

<210> SEQ ID NO 16
<211> LENGTH: 22
<212> TYPE: DNA
<213> ORGANISM: Artificial Sequence
<220> FEATURE:
<223> OTHER INFORMATION: Reverse PCR primer for CFH

<400> SEQUENCE: 16
ccattggtaa aacaaggtga ca                                               22

<210> SEQ ID NO 17
<211> LENGTH: 20
<212> TYPE: DNA
<213> ORGANISM: Artificial Sequence
<220> FEATURE:
<223> OTHER INFORMATION: Forward PCR primer for LOC387715

<400> SEQUENCE: 17
gcacctttgt caccacatta                                                  20

<210> SEQ ID NO 18
<211> LENGTH: 20
<212> TYPE: DNA
<213> ORGANISM: Artificial Sequence
<220> FEATURE:
<223> OTHER INFORMATION: Reverse PCR Primer for LOC387715

<400> SEQUENCE: 18
gcctgatcat ctgcatttct                                                  20

<210> SEQ ID NO 19
<211> LENGTH: 107
<212> TYPE: PRT
<213> ORGANISM: Homo sapiens

<400> SEQUENCE: 19

Met Leu Arg Leu Tyr Pro Gly Pro Met Val Thr Glu Ala Glu Gly Lys
1               5                   10                  15

Gly Gly Pro Glu Met Ala Ser Leu Ser Ser Val Val Pro Val Ser
            20                  25                  30

Phe Ile Ser Thr Leu Arg Glu Ser Val Leu Asp Pro Gly Val Gly Gly
        35                  40                  45

Glu Gly Ala Ser Asp Lys Gln Arg Ser Lys Leu Ser Leu Ser His Ser
    50                  55                  60
```

-continued

```
Met Ile Pro Ala Ala Lys Ile His Thr Glu Leu Cys Leu Pro Ala Phe
65                  70                  75                  80

Phe Ser Pro Ala Gly Thr Gln Arg Arg Phe Gln Gln Pro Gln His His
                85                  90                  95

Leu Thr Leu Ser Ile Ile His Thr Ala Ala Arg
            100                 105

<210> SEQ ID NO 20
<211> LENGTH: 808
<212> TYPE: DNA
<213> ORGANISM: Homo sapiens

<400> SEQUENCE: 20
gagatggcag ctggcttggc aaggggacag cacctttgtc accacattat gtccctgtac      60
cctacatgct gcgcctatac ccaggaccga tggtaactga ggcggagggg aaaggagggc     120
ctgagatggc aagtctgtcc tcctcggtgg ttcctgtgtc cttcatttcc actctgcgag     180
agtctgtgct ggaccctgga gttggtggag aaggagccag tgacaagcag aggagcaaac     240
tgtctttatc acactccatg atcccagctg ctaaaatcca cactgagctc tgcttaccag     300
ccttcttctc tcctgctgga acccagagga ggttccagca gcctcagcac cacctgacac     360
tgtctatcat ccacactgca gcaaggtgat tctgccaaaa catatctcct taaaagccaa     420
ctggagcttc tcatcagcat caatgtgaag ccaaaaatcc ttaggaggac agagggagtc     480
cctcacaacc tagactggtc cccttccctc cagctgcctc aactgtccac aggactctct     540
tcccacctgc ggccacactg tgcaacctgg aatttcccca cctgggcgga ctcatcacgt     600
catcaccaat tggatgcatc ttctgctctg tgcagctggt gaaatctttc tcaacccttg     660
agatgcagcc caatcttctc ctaacatctg gattcctctc tgtcactgca ttccctcctg     720
tcatcctgcc tttgttttct tgccctcctt tctctcccgg gtgataggca ttaactaaaa     780
ttaaataaaa attcagatca tccttgca                                       808
```

SUSCEPTIBILITY GENES FOR AGE-RELATED MACULOPATHY (ARM) ON CHROMOSOME 10Q26

CROSS REFERENCE TO RELATED APPLICATIONS

This application is a continuation of prior application Ser. No. 11/448,267, filed Jun. 7, 2006, now U.S. Pat. No. 7,695,909 which is incorporated herein by reference in its entirety, which claims the benefit under 35 U.S.C. §119(e) to U.S. Provisional Patent Application No. 60/688,572, filed Jun. 8, 2005, which is incorporated herein by reference in its entirety.

STATEMENT REGARDING FEDERALLY SPONSORED RESEARCH AND DEVELOPMENT

This invention was made with government support under Grant Nos. R01EY009859 and P30-EY008098, awarded by the National Institutes of Health, National Eye Institute. The government has certain rights in this invention.

BACKGROUND

Age-related maculopathy (also known as age-related macular degeneration) is a leading cause of central blindness in the elderly population and numerous studies support a strong underlying genetic component to this complex disorder. Genome-wide linkage scans using large pedigrees, affected sib pairs, and more recently, discordant sib pairs, have identified a number of potential susceptibility loci (Klein et al. 1998 Age-related macular degeneration. Clinical features in a large family and linkage to chromosome 1q. Archives of Ophthalmology 116:1082-1088; Weeks et al. 2000 A full genome scan for age-related maculopathy. Human Molecular Genetics 9:1329-1349; Majewski et al. 2003 Age-related macular degeneration—a genome scan in extended families. Am J Hum Genet 73:540-550; Schick et al. 2003 A whole-genome screen of a quantitative trait of age-related maculopathy in sibships from the Beaver Dam Eye Study. Am J Hum Genet 72:1412-1424; Seddon et al. 2003 A genomewide scan for age-related macular degeneration provides evidence for linkage to several chromosomal regions. Am J Hum Genet 73:780-790; Abecasis et al. 2004—Age-related macular degeneration: a high-resolution genome scan for susceptibility Loci in a population enriched for late-stage disease. Am J Hum Genet 74:482-494; Iyengar et al. 2004 Dissection of genomewide-scan data in extended families reveals a major locus and oligogenic susceptibility for age-related macular degeneration. Am J Hum Genet 74:20-39; Kenealy et al. 2004 Linkage analysis for age-related macular degeneration supports a gene on chromosome 10q26. Mol Vis 10:57-61; Schmidt et al. 2004 Ordered subset linkage analysis supports a susceptibility locus for age-related macular degeneration on chromosome 16p12. BMC Genet 5:18; Weeks et al. 2004 Age-related maculopathy: a genomewide scan with continued evidence of susceptibility loci within the 1q31, 10q26, and 17q25 regions. Am J Hum Genet 75:174-189; Santangelo et al. 2005 A Discordant Sib-Pair Linkage Analysis of Age-Related Macular Degeneration. Ophthalmic Genetics 26:61-68). Genome-wide linkage screen strongly implicated the 10q26 region as likely to contain an age-related macular degeneration (AMD) gene (Weeks et al. 2004); this region has also been supported by many other studies and is the top-ranked region in a recent meta analysis (Fisher et al. 2005 Meta-analysis of genome scans of age-related macular degeneration. Hum Mol Genet. 2005 Aug. 1; 14(15):2257-64). Recently, three papers appeared in Science (Edwards et al. 2005 Complement Factor H Polymorphism and Age-Related Macular Degeneration. Science 308, 421-424; Haines et al. 2005 Complement Factor H Variant Increases the Risk of Age-Related Macular Degeneration. Science 308, 419-421. Klein et al. 2005 Complement Factor H Polymorphism in Age-Related Macular Degeneration. Science 308, 385-389) identifying an allelic variant in complement factor H (CFH) as responsible for the linkage signal seen on Chromosome 1 and accounting for a significant attributable risk for ARM in both familial and sporadic cases. These findings have been confirmed (Conley et al. 2005 Candidate gene analysis suggests a role for fatty acid biosynthesis and regulation of the complement system in the etiology of age-related maculopathy. Hum Mol Genet 14: 1991-2002; Hageman et al. (2005a) From The Cover: A common haplotype in the complement regulatory gene factor H (HF1/CFH) predisposes individuals to age-related macular degeneration. Proc Natl Acad Sci USA 102:7227-7232; and Zareparsi et al. 2005a Strong Association of the Y402H Variant in Complement Factor H at 1q32 with Susceptibility to Age-Related Macular Degeneration. Am J Hum Genet 77:149-53). CFH has been previously suspected of playing a role in ARM due to the work of Hageman and Anderson (Hageman and Mullins 1999 Molecular composition of drusen as related to substructural phenotype. Molecular Vision 5:28; Johnson et al. 2000 A potential role for immune complex pathogenesis in drusen formation. Experimental Eye Research 70:441-449 Complement activation and inflammatory processes in Drusen formation and age related macular degeneration. Experimental Eye Research 73:887-896; Mullins et al. 2000 Drusen associated with aging and age-related macular degeneration contain proteins common to extracellular deposits associated with atherosclerosis, elastosis, amyloidosis, and dense deposit disease. FASEB Journal 14:835-846; Hageman et al. 2001 An integrated hypothesis that considers drusen as biomarkers of immune-mediated processes at the RPE-Bruch's membrane interface in aging and age-related macular degeneration. Progress in Retinal & Eye Research 20:705-732; Johnson et al. 2001), who have shown that the subretinal deposits (drusen) that are observed in many ARM patients contain complement factors. However until other genes that contribute to ARM are identified, CFH remains an isolated piece of the puzzle, implicating the alternative pathway and inflammation as part of the ARM pathogenesis, but failing to account for the unique pathology that is observed in the eye.

SUMMARY

To this end, as described below, allelic variants, including single nucleotide polymorphisms, have been identified on Chromosome 10q26. These allelic variants are shown herein to be associated with an increased risk of developing Age-Related Maculopathy. The allelic variants are located within LOC387715 and/or the PLEKHA1 gene on chromosome 10q26. In one embodiment, the allelic variation is within LOC387715.

In one non-limiting embodiment of the present invention, a method of identifying a human subject having an increased risk of developing Age-Related Maculopathy is provided. The method comprises identifying in a nucleic acid sample from the subject the occurrence of an allelic variant located in Chromosome 10q26 that is associated with risk of developing Age-Related Maculopathy. In one non-limiting embodiment, the allelic variant occurs in the PLEKHA1/LOC387715/PRSS11 locus of Chromosome 10q26. For example and without limitation, the allelic variant is an allelic variant of one or both of PLEKHA1 and LOC387715, such as, without limitation, a Ser69Ala variant in LOC387715.

In another non-limiting example, the variant is a polymorphism corresponding to one or more of the variants identified as rs4146894, rs10490924, rs1045216, rs1882907, rs760336, rs763720, rs800292, rs1483883 and rs1853886. The allelic variant may be, without limitation, a mutation that produces one of a non-functional gene product and altered expression of a gene product, such as one or more of a frameshift mutation, a promoter mutation and a splicing mutation.

In one embodiment, the method comprises further identifying in a nucleic acid sample from the subject the occurrence of an allelic variant of complement factor H, such as, without limitation, a variant corresponding to the single nucleotide polymorphism identified as rs1853883.

The method may employ any useful technology, such as without limitation: a nucleic acid amplification assay, such as one of a PCR, a reverse transcriptase PCR (RT-PCR), an isothermic amplification, a nucleic acid sequence based amplification (NASBA), a 5' fluorescence nuclease assay (for example TAQMAN assay), a molecular beacon assay and a rolling circle amplification. The allelic variation may be identified using an array that typically comprises one or more reagents for identifying in a nucleic acid sample from the subject the occurrence of an allelic variation corresponding to two or more of the single nucleotide polymorphisms identified as rs4146894, rs1045216, rs10490924, rs1882907, rs760336, rs763720, rs800292, rs1483883 and rs1853886.

In another non-limiting embodiment, an array is provided comprising one or more reagents sequences for identifying in a nucleic acid sample from a subject the occurrence of an allelic variation located on Chromosome 10q26 that is associated with risk of development of Age-Related Maculopathy. The allelic variation may, without limitation, may occur in the PLEKHA1/LOC387715/PRSS11 locus of Chromosome 10q26, and, for example, may correspond to one or more single nucleotide polymorphisms identified as rs4146894, rs1045216, rs10490924, rs1882907, rs760336, rs763720, rs800292, rs1483883 and rs1853886.

BRIEF DESCRIPTION OF THE DRAWINGS

FIG. 1-2 is split at line A-A'.

FIG. 2: Single-point and multipoint linkage results on Chromosome 10. FIG. 2-1 summarizes the results when all SNPs were used. FIG. 2-2 summarizes the results when only H-clust SNPs were used for analysis. The peaks marked with "F", represent likely false peaks due to high SNP-SNP LD, while the peaks marked "G" and "P," correspond to the loci containing GRK5 and PLEKHA1 respectively. The horizontal lines indicate the 1-unit support interval of multipoint $S_{all}$ (maximum $S_{all}$−1).

FIG. 3A: The false peak at 135 cM (see FIG. 2), FIG. 3B: The false peak at 142 cM (see FIG. 2), FIG. 3C: Linkage peak. FIGS. 3D-1, 3D-2, 3D-3 and 3D-4 are larger versions of FIG. 3C, divided at lines B-B', C-C' and D-D'. The SNP with the largest $S_{all}$ in false peaks (FIGS. 3A and 3B) are shown in gray and significant SNPs overlying the 5 genes (GRK5/RGS10/PLEKHA1/LOC387715/PRSS11) from CCREL (Table 5) are shown in gray in the true linkage peak. Shades of gray indicate significant LD between SNP pairs (dark gray squares with no numbers indicate pairwise D'=1), white squares indicate no evidence of significant LD and gray squares with no numbers indicate pairwise D' of 1 without statistical significance. LD is measured using D' and the numbers in the squares give pair wise LD in D'*100.

FIG. 4: Multipoint linkage results on Chromosome 1. FIG. 4-1 summarizes results when all SNPs were used and FIG. 4-2 summarizes results when only H-clust SNPs were used for analysis. The peaks marked with "F" represent likely false peaks due to high SNP-SNP LD, while the peaks marked with "C" correspond to the CFH gene. The horizontal lines indicate the 1-unit support interval of multipoint $S_{all}$ (maximum $S_{all}$ in CFH-1).

FIG. 5A: The false peak at 188 cM (see FIG. 4), FIG. 5B: The false peak at 202 cM (see FIG. 4), FIG. 5C: The linkage peak overlying the CFH loci. The SNP with the largest $S_{all}$ in false peaks are shown in gray and significant SNPs overlying CFH from CCREL (Table 5) are shown in grey in the true linkage peak. Shades of gray indicate significant LD between SNP pairs (dark gray squares with no numbers indicate pairwise D'=1), white squares indicate no evidence of significant LD and gray squares with no numbers indicate pairwise D' of 1 without statistical significance. LD is measured using D' and the numbers in the squares give pair wise LD in D'*100.

FIG. 6A: Linkage disequilibrium patterns in the GRK5 (Block 1), RGS10 (SNP 6), PLEKHA1 (Block 2), LOC387715 (Block 3), PRSS11 (Block 4). FIG. 6B: Linkage disequilibrium patterns in CFH (Block 1). Shades of gray indicate significant LD between SNP pairs (dark gray squares with no numbers indicate pairwise D'=1), white squares indicate no evidence of significant LD and gray squares with no numbers indicate pairwise D' of 1 without statistical significance. LD is measured using D' and the numbers in the squares give pair wise LD in D'*100. Significant SNPs from the CCREL allele test are highlighted in gray (see Table 6). Three SNPs (rs6428352, rs12258692 and rs11538141) were not included because of very low heterozygosity and one SNP, rs2736911, was not included because it was uninformative. Note the blocks were drawn to clearly show the position of the genes and do not represent haplotype blocks.

FIG. 16 provides an amino acid (SEQ ID NO: 19) and nucleotide sequence (SEQ ID NO: 20) for LOC387715.

DETAILED DESCRIPTION

Figure 1:
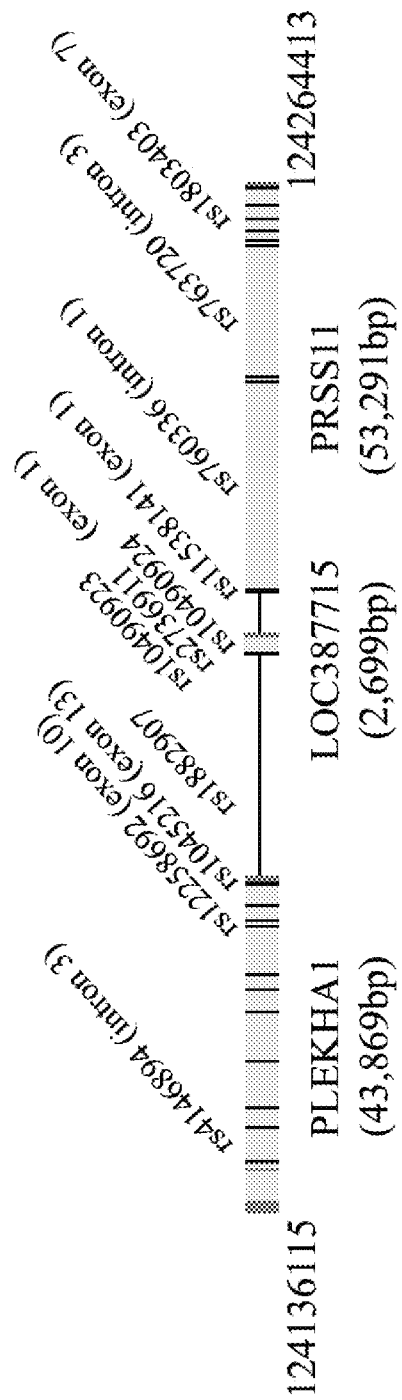
FIG. 1-1: Location of CIDR and locally genotyped SNPs with respect to candidate genes. Positions, distances and nucleotide position along Chromosome 10 are derived from NCBI Entrez-gene and SNP databases.

As described below, allelic variants, including single nucleotide polymorphisms, have been identified on Chromosome 10826. These allelic variants are shown herein to be associated with an increased risk of developing Age-Related Maculopathy. Example 1 identified PLEKHA1 and/or LOC387715 as loci of allelic variants related to ARM. Further studies, as shown in Example 2, confirm and add further support to the identified relevance of variations in LOC387715 as a marker for ARM. The relevance of variations of PLEKHA1 as a marker for ARM has not been ruled out but the evidence from the most recent genetic studies more strongly implicate the variants within the LOC387715 gene.

Methods are therefore provided for identifying a human subject having an increased risk of developing Age-Related Maculopathy (ARM). The methods comprise identifying in a nucleic acid sample from the subject the occurrence of an allelic variant or a specific haplotype (comprised of several allelic variants) of PLEKHA1 and/or LOC387715, and in one non-limiting embodiment, LOC387715. Specific single nucleotide polymorphisms (SNPs) have been identified within these loci, including, without limitation, those SNPs identified as rs4146894, rs1045216, rs10490924, rs1882907, rs760336 and rs763720. The method may further comprise identifying an allelic variation in Complement Factor H (CFH), such as, without limitation the allelic variant identified as rs1853883.

As used herein, an "allelic variation" refers to a variation in the nucleic acid and typically primary amino acid sequence of a gene in one or more alleles in a subject, such as a human patient. Allelic variations include single or multiple nucleic acid and amino acid substitutions, additions or deletions that have any one of a number of effect on protein expression, including without limitation: promoter activity that regulates transcription, frameshift, early protein termination, protein mis-folding, altered protein processing, destruction (or enhancement) of active sites or binding sites of a protein, mis-splicing of an mRNA or any other property of a nucleic acid or protein that effects the expression and/or function of the final gene products. An amino acid and nucleic acid sequence variation may or may not have be silent, that is, no phenotypic effect, such as risk of disease, can be associated with that sequence variation. On the other had, an allelic variation is a variation in a consensus "wild type" nucleic acid or amino acid sequence to which risk of a disease state, such as ARM, can be attributed, associated or otherwise connected, for example and without limitation, by statistical methods is described herein. Thus, the LOC387715 single nucleotide polymorphism identified as rs10490924 (Ser69Ala) is an allelic variation.

A large number of methods, including high throughput methods, are available for detection of SNPs and/or other allelic variations, for example and without limitation the PCR and Restriction Fragment Length Polymorphisms methods described in the Examples below. In one embodiment, DNA from a sample is sequenced (resequenced) by any method to identify a SNP or small alleic variation. A large variety of resequencing methods are known in the art, including high-throughput methods. Amplification-based methods also are available to identify allelic variations, such as SNPs, including, without limitation: PCR, reverse transcriptase PCR (RT-PCR), isothermic amplification, nucleic acid sequence based amplification (NASBA), 5' fluorescence nuclease assay (for example TAQMAN assay), molecular beacon assay and rolling circle amplification. Other methods, such as Restriction Fragment Length Polymorphisms RFLP, also maybe employed—as is appropriate and effective to identify variant allele(s). Assays may be multiplexed, meaning two or more reactions are carried out simultaneously in the same physical location, such as in the same tube or position on an array—so long as the reaction products of the multiplexed reactions can be distinguished. As a non-limiting example, TAQMAN or molecular beacon assays can be multiplexed by use of and by monitoring of accumulation or depletion of two different fluorochromes corresponding to two different sequence-specific probes. In most cases, the appropriate method is dictated by personal choice and experience, equipment and reagents on hand, the need for high throughput and/or multiplexed methods, cost, accuracy of the method, and the skill level, of technicians running the assay. Design and implementation of those techniques are broadly-known and are well within the abilities of those of average skill in the art.

In the implementation of the methods provided herein, an array may be utilized. Arrays are particularly useful in implementing high-throughput assays. The array typically comprises one or more reagents, for example and without limitation, nucleic acid primers and/or probes, for identifying in a nucleic acid sample from a human subject the occurrence of an allelic variation corresponding to one or more single nucleotide polymorphisms identified in LOC387715 and/or PLEKHA1, such as, without limitation, the SNPs identified as: rs4146894, rs1045216, rs10490924, rs1882907, rs760336, rs763720, rs800292, rs1483883, rs1853883 and rs1853886. An array would allow simultaneous testing and identification of one or more allelic variation in LOC387715 and/or PLEKHA1, such as, without limitation, the SNPs identified as: rs4146894, rs1045216, rs10490924, rs1882907, rs760336, rs763720, rs800292, rs1483883, rs1853883 and rs1853886 as well as simultaneous identification of allelic variations in CFH, other genes/loci and control genes/loci/nucleic acids.

As used herein, the term "array" refers to reagents for facilitating identification of allelic variations in a gene located at two or more identifiable locations. In one embodiment, an array is an apparatus having two or more discrete, identifiable reaction chambers, such as, without limitation a 96-well dish, in which reactions comprising identified constituents are performed. In an exemplary embodiment, two or more nucleic acid primers or probes are immobilized onto a substrate in a spatially addressable manner so that each individual primer or probe is located at a different and (addressable) identifiable location on the substrate. Substrates include, without limitation, multi-well plates, silicon chips and beads. In one embodiment, the array comprises two or more sets of beads, with each bead set having an identifiable marker, such as a quantum dot or fluorescent tag, so that the beads are individually identifiable using, for example and without limitation, a flow cytometer. In one embodiment, in the context of the present disclosure, an array may be a multi-well plate containing two or more well reaction chambers with primers for amplifying DNA to identify SNPs or probes for binding specific sequences. As such, reagents, such as probes and primers may be bound or otherwise deposited onto or into specific locations on an array. Regeants may be in any suitable form, including, without limitation: in solution, dried, lyophilized or glassified.

Useful Array technologies include, for example and without limitation an Affymetrix GeneChip® Array, for example, GeneChip® CustomSeq® Resequencing Arrays (commercially available from Affymetrix Inc. of Santa Clara, Calif.) and like technologies. Informatics and/or statistical software or other computer-implemented processes for analyzing array data and/or identifying genetic risk factors from data obtained from a patient sample, are known in the art.

As used herein, a "reagent for identifying in a nucleic acid sample from a subject the occurrence of an allelic variation" that either is identified specifically or is identified in the context of a gene or locus, refers to a reagent that enables identification of that specific allelic variation by any suitable method, for example and without limitations, by PCR, resequencing 5' exonuclease (TaqMan) assay and/or array or high-throughput assays. Non-limiting examples of such reagents include sequence-specific primers, primer sets and probes for use in any useful assay system. Primers and probes may take any useful form, but typically are nucleic acids, but may be nucleic acid analogs, such as, without limitation phosphorothiates.

In Example 1, a family-based linkage study and a case-control association study were undertaken using a high density SNP panel in two regions of linkage on 1q31 and 10q26. SNP linkage and association results for Chromosome 1q31 confirmed that the peak of linkage and the strongest associations with ARM were localized over the CFH gene. Both family and case-control data on Chromosome 10q26 were analyzed to identify the next major ARM susceptibility-related gene.

A follow-up study, described in Example 2, utilized a nested case-control design with subjects originally recruited through a Cardiovascular Health Study (CHS), a population-based cohort for which Age-Related Maculopathy (ARM) status was not a factor for ascertainment, and an Age-Related Eye Disease Study (AREDS), a population-based cohort for which ARM status was a factor for ascertainment. These cohorts were utilized to investigate the CFH, PLEKHA1, LOC387715 and ELOVL4 genes in ARM susceptibility in two cohorts with different ascertainment schemes. Furthermore, these two cohorts plus eleven and four additional case-control studies were included in a meta-analysis for CFH and LOC387715 respectively. CFH was significantly associated with ARM status in both cohorts (p<0.00001) and meta-analysis confirmed that the risk allele in the heterozygous or homozygous state (OR, 2.4 and 6.2; 95% CI (Confidence Interval), 2.2-2.7 and 5.4-7.2 respectively) confers this susceptibility. LOC387715 was significantly associated with ARM status in both cohorts (p<0.00001) and meta-analysis confirmed that the risk allele in the heterozygous and homozygous state (OR, 2.5 and 7.3; 95% CI, 2.2-2.9 and 5.7-9.4 respectively) confers this susceptibility. PLEKHA1, which is closely linked to LOC387715, was significantly associated with ARM status in the AREDS cohort but not the CHS cohort and ELOVL4 was not significantly associated ARM in either cohort. This study provides additional support for the CFH and LOC387715 genes in ARM susceptibility via the evaluation of cohorts that had different ascertainment schemes in regard to ARM status as well as further support through a meta-analysis.

Example 1

Material and Methods
Families and Case-Control Cohort

A total of 612 AMD families and 184 unrelated controls were sent to the Center for Inherited Disease Research (CIDR) for genotyping. Due to possible population substructure, analysis was restricted to the Caucasian subset of our data. The Caucasian subset had 594 AMD families, containing 1443 genotyped individuals, and 179 unrelated controls. The Caucasian families contained 430 genotyped affected sib pairs, 38 genotyped affected avuncular pairs, and 52 genotyped affected first cousin pairs.

A total of 323 Caucasian families, 117 unrelated controls, and 196 unrelated cases were also genotyped locally for additional SNPs. The local subset contained 824 genotyped individuals, 298 genotyped affected sib pairs, 23 genotyped affected avuncular pairs and 38 genotyped affected first cousin pairs. PedStats from the Merlin package (Abecasis et al. 2000) was used to easily get summary counts on family data.

Affection Status Models

Three classification models (A, B and C) were defined for the severity of ARM status (Weeks et al. 2004). For simplicity, attention was restricted to "Type A" affecteds, the most stringent and conservative diagnosis. Only unrelated controls were unaffected under all three diagnostic models were used. Unaffected individuals were those for whom eye care records and/or fundus photographs indicated either no evidence of any macular changes (including drusen) or a small number (less than 10) of hard drusen (50 microns or less in diameter) without any other RPE changes. Individuals with large numbers of extramacular drusen were not coded as unaffected when this information was available.

In efforts to examine specific ARM sub-phenotypes, only those with end stage disease, either those with evidence of a choroidal neovascular membrane (CNV) in either eye, or those with geographic atrophic (GA) in either eye were chosen to look at. There are a significant number of individuals who have been reported to have both geographic atrophy and CNV, though this is problematic since it is often difficult to tell in these cases if the geographic atrophy is secondary to the damage from the CNV or from the treatment given to limit the CNV growth (i.e., laser, surgery, or photodynamic therapy). Because it is often difficult to discern from photographs or records if a person had GA in an eye prior to the development of a CNV, those patients who had both pathologies within the CNV group were included. However, only a subset of this overlapping group were allowed to be included within the geographic atrophy group, specifically if there was reported geographic atrophy in one eye that did not have evidence of a CNV. Table 1 shows the numbers of such individuals for each of the three case sets. This approach may have excluded a small proportion of individuals from the geographic atrophy group who had asymmetric geographic atrophy prior to the development of CNV in the same eye or who may have had bilateral geographic atrophy, but developed CNV's in both eyes.

TABLE 1

The distribution of subphenotypes in patients with advanced ARM. Numbers in parentheses refer to number of individuals with both CNV and GA and also included in GA group (see the text for the selection criteria) for odds ratio and attributable risk estimation and association tests.

|  | Cases from CIDR families | | Cases from local families | | Local unrelated cases | |
| --- | --- | --- | --- | --- | --- | --- |
|  | GA | no GA | GA | no GA | GA | no GA |
| CNV | 220 (76) | 187 | 130 (45) | 106 | 71 (17) | 59 |
| no CNV | 108 | 62 | 57 | 28 | 40 | 26 |

Pedigree and Genotyping Errors and Data Handling

The program PedCheck (O'Connell and Weeks 1998 Ped-Check: A program for identifying genotype incompatibilities in linkage analysis. Am J Hum Genet 63:259-266) was used to check for Mendelian inconsistencies. Since it can be extremely difficult to determine which genotype within a small family is erroneous (Mukhopadhyay et al. 2004 Comparative study of multipoint methods for genotype error detection. Hum-Hered 58:175-189), all genotypes were set at each problematic marker to missing within each family containing a Mendelian inconsistency. Mega2 (Mukhopadhyay et al., Mega2: data-handling for facilitating genetic linkage and association analyses. Bioinformatics 2005 May 15; 21(10):2556-7) was used to set up files for linkage analysis as well as for allele frequency estimation by gene-counting.

Allele Frequencies and Hardy Weinberg Equilibrium

The allele frequencies used in the linkage analyses were estimated, by direct counting, from the unrelated and unaffected controls. All controls were unaffected under all three affection status models. Genotyped spouses that had no children or children who are not yet part of the study were combined with the controls for this study. The exact test of Hardy-Weinberg equilibrium, implemented in Mega2 (Mukhopadhyay et al. 2005 Mega2: data-handling for facilitating genetic linkage and association analyses. Bioinformatics), was performed on our SNPs.

Mendel version 5 (Lange et al. 2001 MENDEL Version 4.0: A complete package for the exact genetic analysis of discrete traits in pedigree and population data sets. Am J of Hum Genet 69 (Supplement):A1886) was also used to estimate allele frequencies directly from the family data, as Mendel properly accounts for relatedness of the subjects while estimating the allele frequencies. Since the majority of the genotyped family members are affected, these estimates are quite close to estimates obtained using unrelated affected cases.

Genetic Map

The Rutgers combined linkage-physical map (version 2.0) (Kong et al. 2004 A combined linkage-physical map of the human genome. Am J Hum Genet 75:1143-1148) was used to predict the genetic position of the SNPs that were not already present in the Rutgers map. Since the distribution of our SNPs is very dense in the regions of interest, the estimated recombination between several SNPs was zero; in these cases the recombination was set to 0.000001. The physical positions were obtained for all of our SNPs from NCBI dbSNP database (human build 35).

Linkage Disequilibrium Structure

Ignoring high linkage disequilibrium (LD) between SNPs when performing linkage analysis can result in false positive findings (Schaid et al. 2002 Caution on pedigree haplotype inference with software that assumes linkage equilibrium. Am J Hum Genet 71:992-995; Huang et al. 2004 Ignoring linkage disequilibrium among tightly linked markers induces false-positive evidence of linkage for affected sib pair analysis. Am J Hum Genet 75:1106-1112). Efforts to take high SNP-SNP LD into account included the following:

1. The LD structure in unrelated controls was studied using the H-cluster method (Rinaldo et al. 2005 Characterization of multilocus linkage disequilibrium. Genetic Epidemiology 28:193-206), which is implemented in R (R Development Core Team 2004 R: A language and environment for statistical computing. R Foundation for Statistical Computing, Vienna, Austria. ISBN 3-900051-07-0). The aim was to determine haplotype-tagging SNPs (htSNPs) for linkage analysis. The method uses hierarchical clustering to cluster highly correlated SNPs. After the clustering, the H-clust method chooses a htSNP for each cluster; the htSNP is the SNP that is most correlated with all other SNPs in the cluster. The SNPs were chosen so that each SNP had a correlation coefficient ($r^2$) greater than 0.5 with at least one htSNP;

2. The program HaploView (Barrett et al. 2005 Haploview: analysis and visualization of LD and haplotype maps. Bioinformatics 21:263-265.) was used to get a graphical view of SNP-SNP LD along Chromosomes 1 and 10; and 3. Haplotype-based association analyses was performed using two and three-SNP moving windows (See below).

Linkage Analysis

1. Single point analysis. As in our previous study (Weeks et al. 2004), LOD scores were computed under single simple dominant model (disease allele frequency=0.0001 and penetrance vector=[0.01 0.90 0.90]). Due to the complexities and late-onset of the ARM phenotype, only two disease phenotypes were used: "affected under model A" and "unknown". Parametric LOD scores were computed under heterogeneity (HLOD), while model-free LOD scores were computed using the linear $S_{all}$ statistic. Both scores were computed using Allegro (Gudbjartsson et al. 2000 Allegro, a new computer program for multipoint linkage analysis. Nat Genet 25:12-13.).

2. Multipoint analysis ignoring linkage disequilibrium. Since inter-marker distances are often very small, LD between SNPs can be high and thus violate the assumption of no LD made by most linkage analysis programs. Multipoint analyses ignoring LD were performed using Allegro (Gudbjartsson et al. 2000). Both HLODs and $S_{all}$ statistics were computed.

3. Multipoint analysis using htSNPs. When using only the htSNPs for LOD score calculation, the number of SNPs decreases to 533 on Chromosome 1 and 159 on Chromosome 10. Multipoint LOD analyses were done as before (Weeks et al. 2004). The SNPs that were omitted fit well to the SNP-SNP LD structure estimated with HaploView (Barrett et al. 2005).

Association Analysis

In order to use all of the cases from the families, the new CCREL program (Browning et al. 2005 Case-Control single-marker and haplotypic association analysis of pedigree data. Genet Epidemiol 28:110-122.) was used, which permits one to test for association using related cases simultaneously with unrelated controls. CCREL was used to analyze SNPs under the linkage peak on Chromosomes 1 and 10 to test for association. The CCREL test accounts for biologically-related subjects by calculating effective number of cases and controls. For these analyses, unrelated controls were given a "normal" phenotype, while family members that are not affected with 'Type A' ARM were given an "unknown" phenotype (The CCREL approach has not yet been extended to permit one to simultaneously use both related cases and related controls). The effective number of controls for each SNP used for association testing is therefore number of controls genotyped for that SNP. An allelic test, a haplotype test using two SNP sliding window, a haplotype test using three SNP sliding window and a genotype test were performed. The CCREL R package was used for analysis as provided by the authors (Browning et al. 2005).

GIST Analysis

To explore which allele/SNP contributes the most to the linkage signal, the genotype-IBD sharing test (GIST) was performed using locally genotyped SNPs and significant SNPs, from the CCREL test, around the linkage peak on both Chromosomes 1 and 10. The GIST test determines if an allele or an allele in LD with it accounts in part for observed linkage signal (Li et al. 2004). Weights were computed for each affected sibship under three different disease models (recessive, dominant, additive)—these weights are unbiased under the null hypothesis of no disease-marker association. The correlation between the family weight variable and nonparametric linkage (NPL) score is the basis of the test statistic. Since the GIST test is currently only applicable to affected sib pair families, families were broken into their component nuclear families before computing the NPL scores. Since the underlying disease model was unknown, we tested under three different disease models (recessive, dominant, additive), and then took the maximum, using a p-value that was adjusted for multiple testing over the three models.

Tripartite Analyses

Analyses were carried out in three sequential steps. First, the set of data that had been genotyped at CIDR was analyzed. Second, after locally genotyping 8 additional SNPs in the PLEKHA1/LOC387715/PRSS11 region on Chromosome 10, the locally-genotyped data set was then analyzed. Note that all of the known non-synonymous SNPs in the PLEKHA1 through PRSS11 region were investigated. As these two data sets differ in size and composition, it is most straightforward to analyze them separately (Table 2). Allele frequency estimation, CCREL association testing, and GIST testing were carried out on both of these (overlapping) data sets as described above. Third, we tested for interaction between the Chromosome 1 and Chromosome 10 regions was tested, as well as examined whether or not the risk differed as a function of the presence of either geographic atrophy or choroidal neovascular membranes.

TABLE 2

Summary of statistical analysis and sample sizes in each part.

Figures 1, 2:
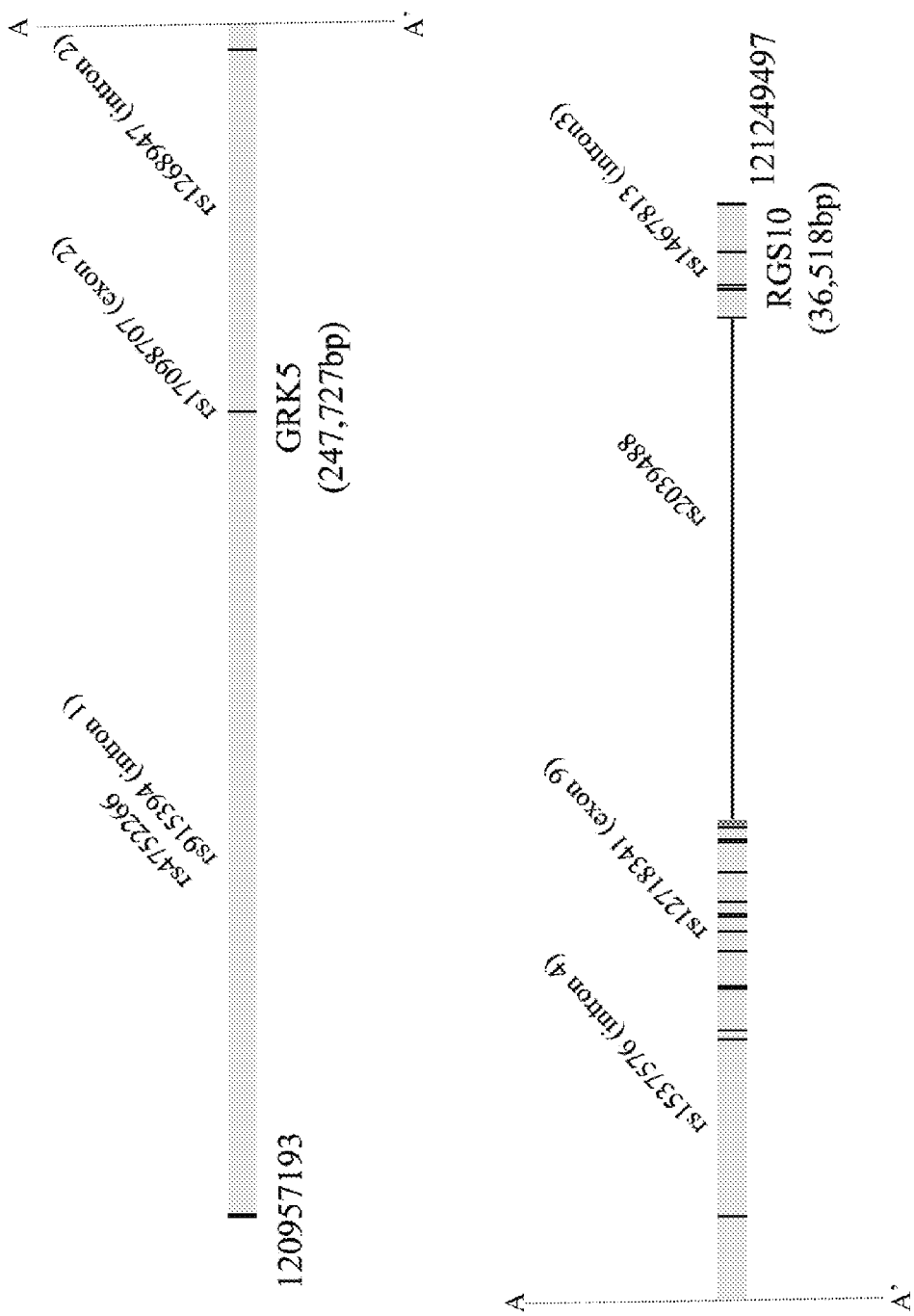
Figures 1, 2:
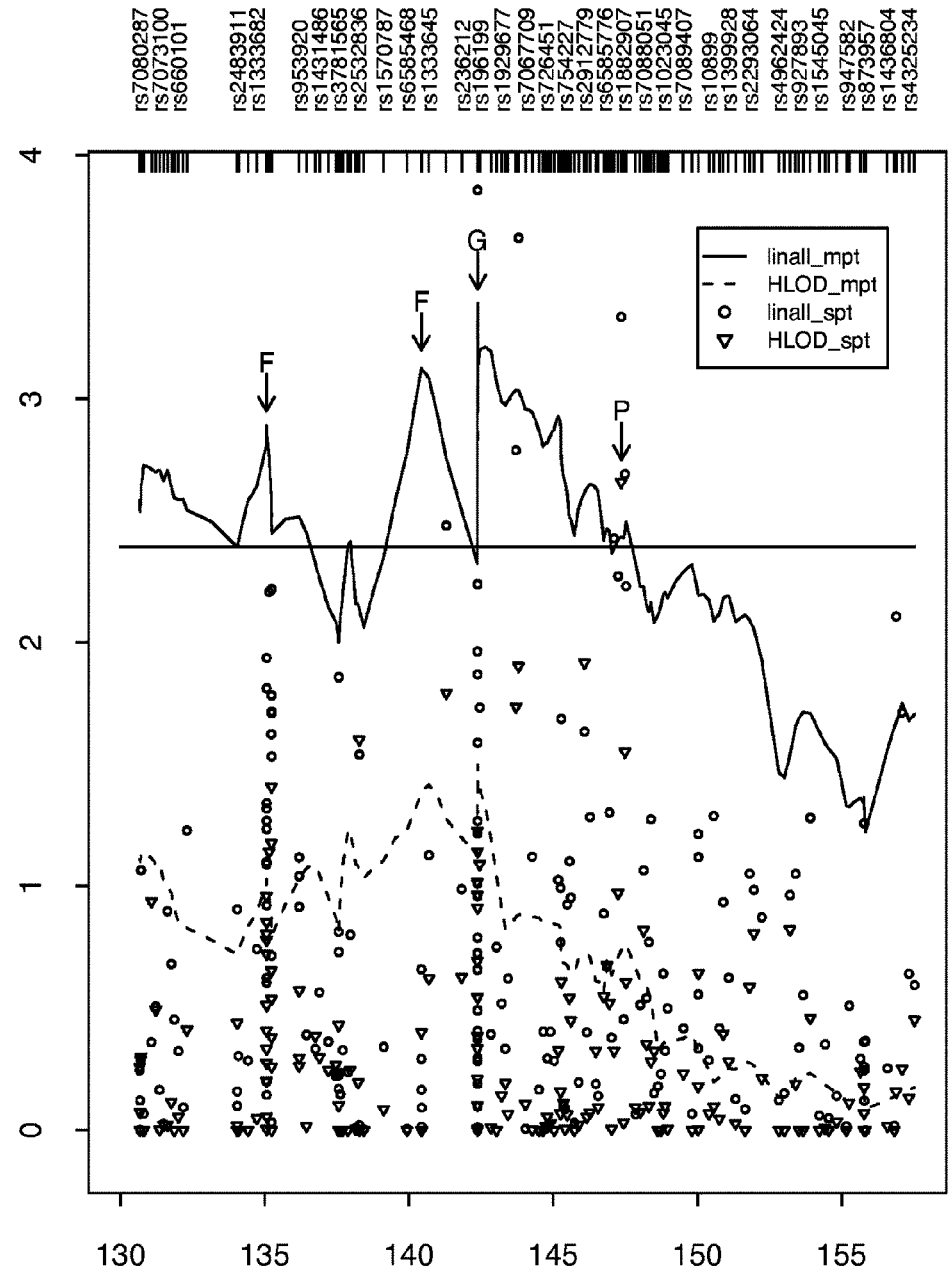
Figure 2:
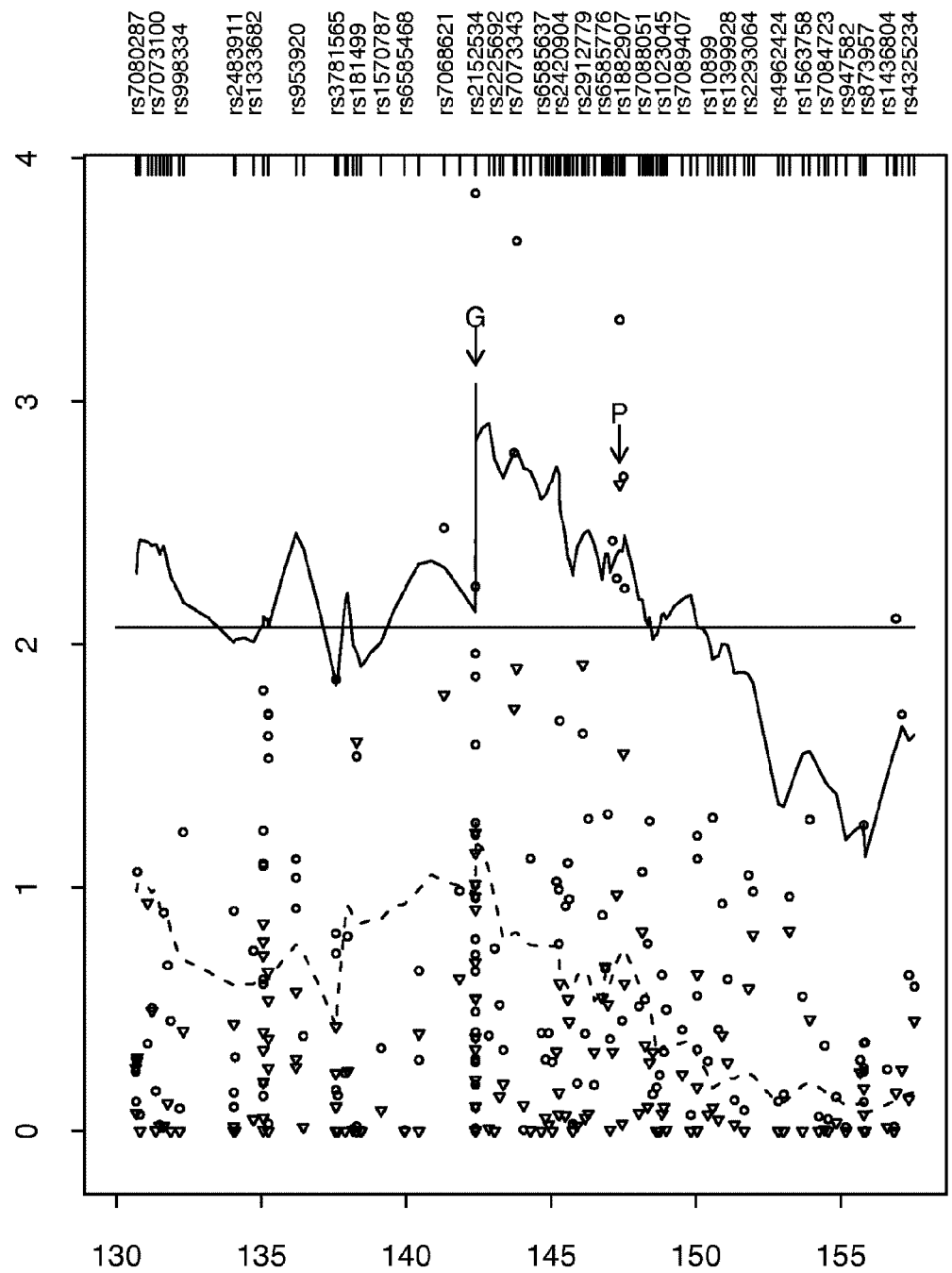
Figure 3A:
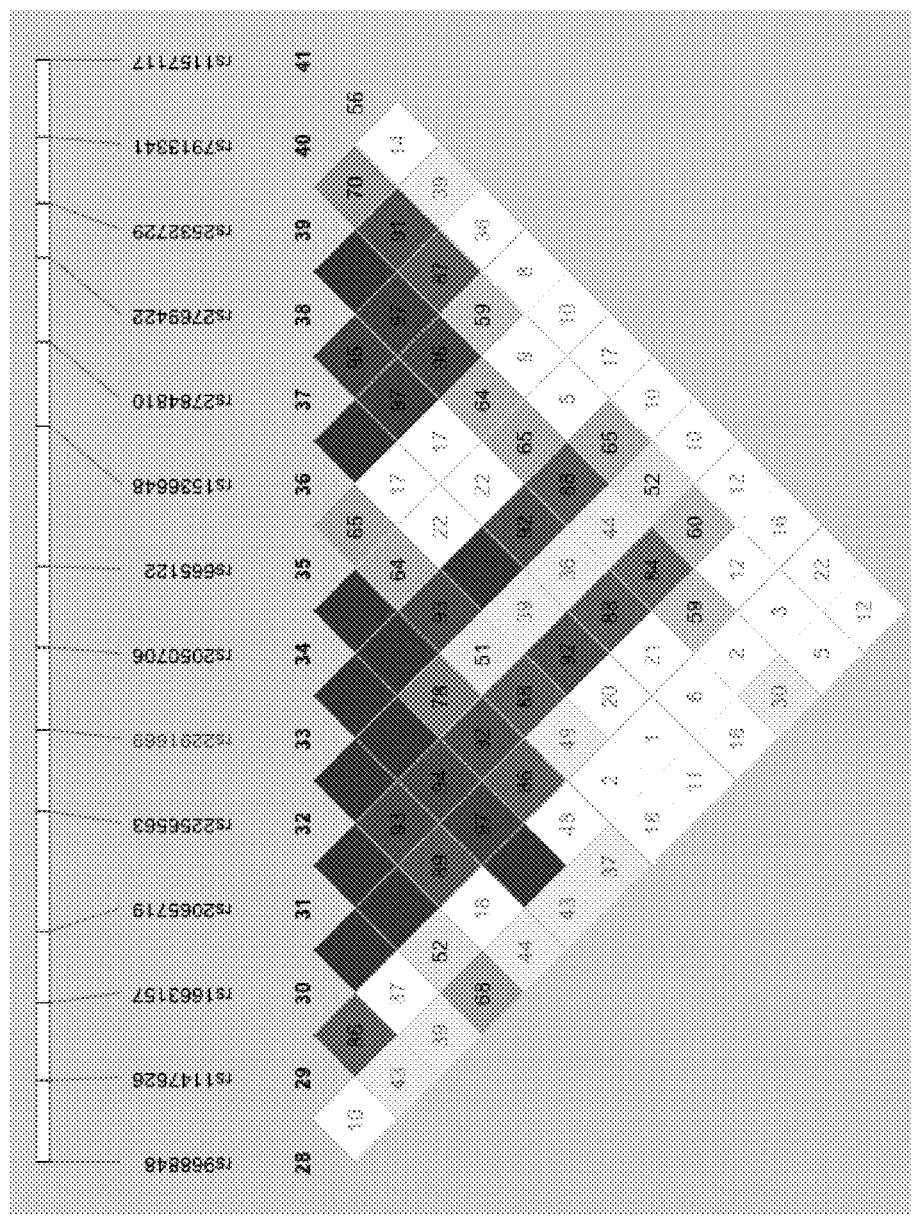
FIGS. 3A-3D: Linkage disequilibrium patterns on chromosome 10 based on 196 CIDR SNPs and 179 unrelated controls.
Figure 3B:
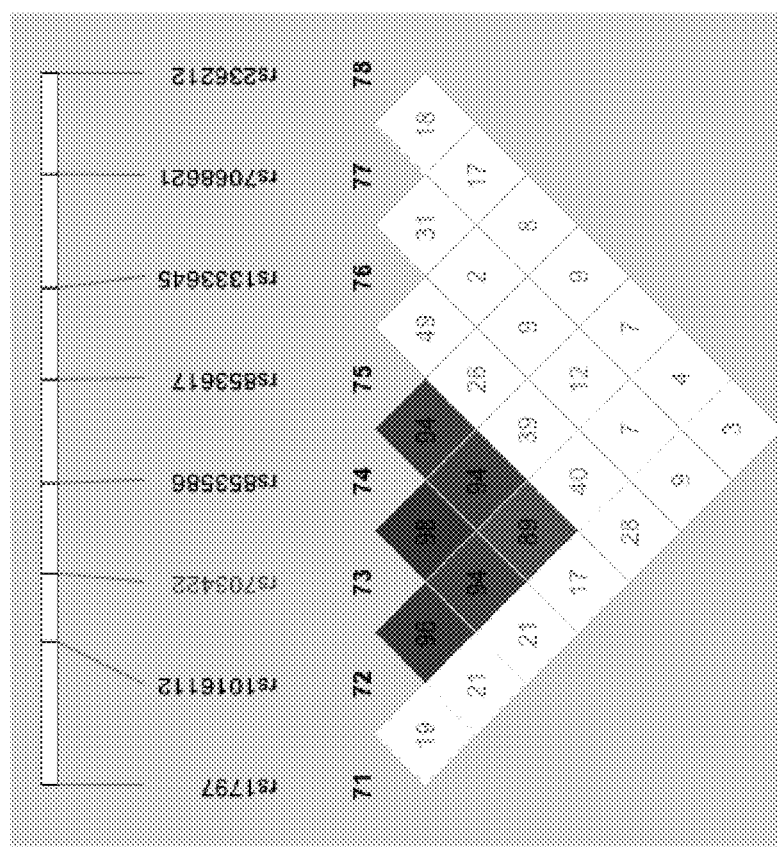
Figure 3C:
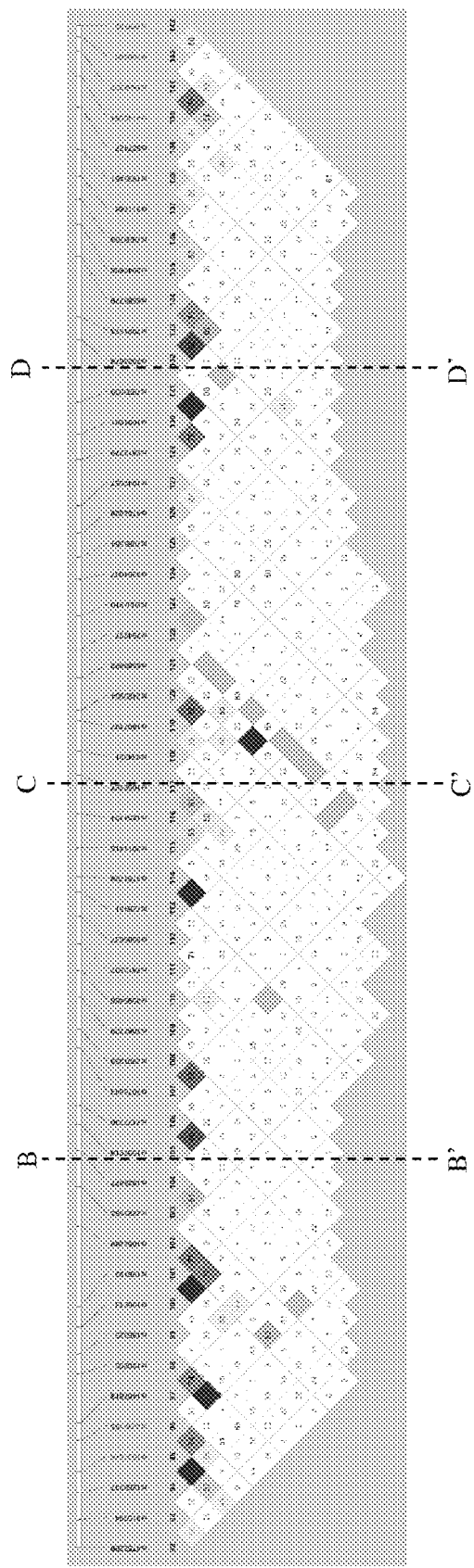
Figures 1, 3D:
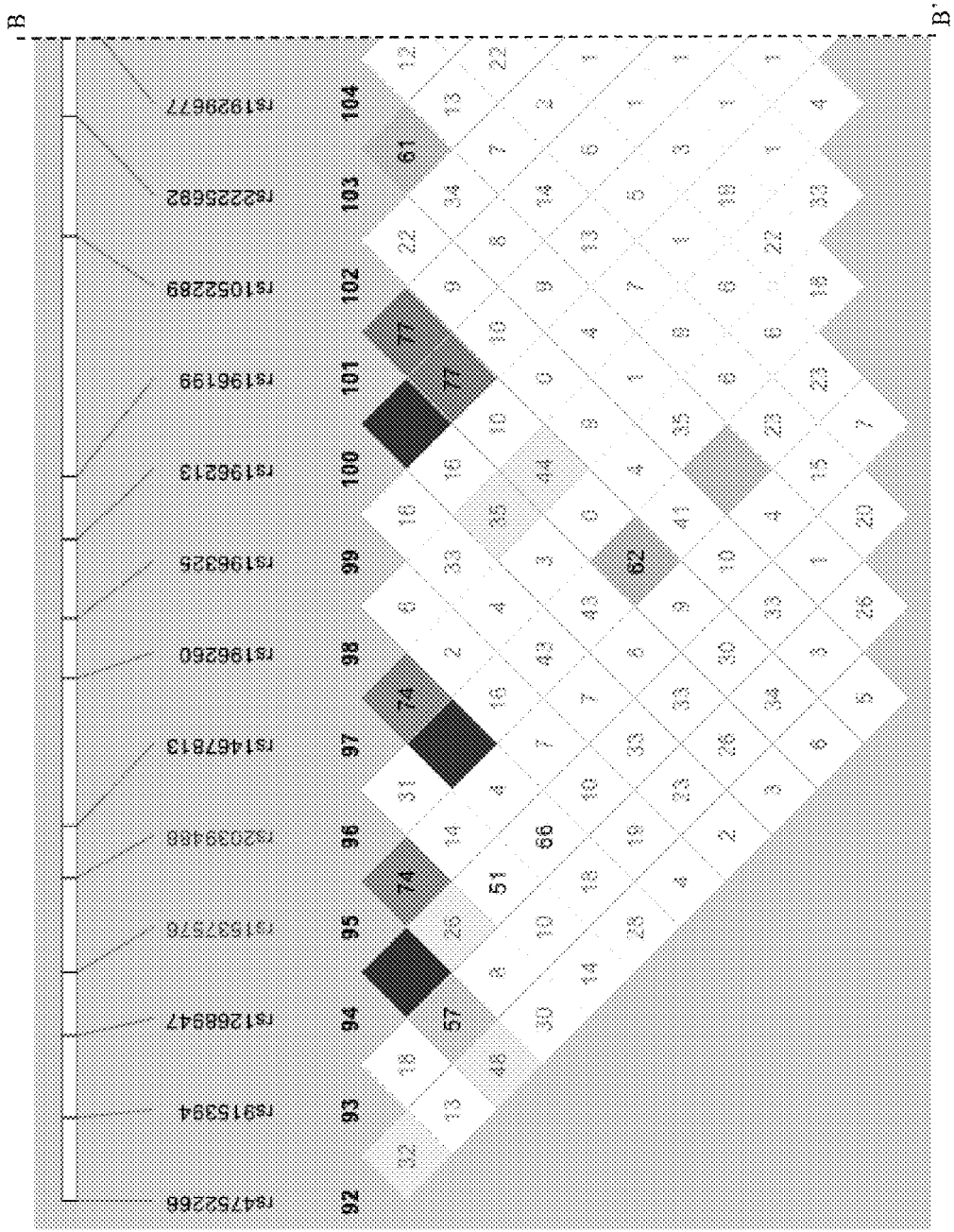
Figures 2, 3D:
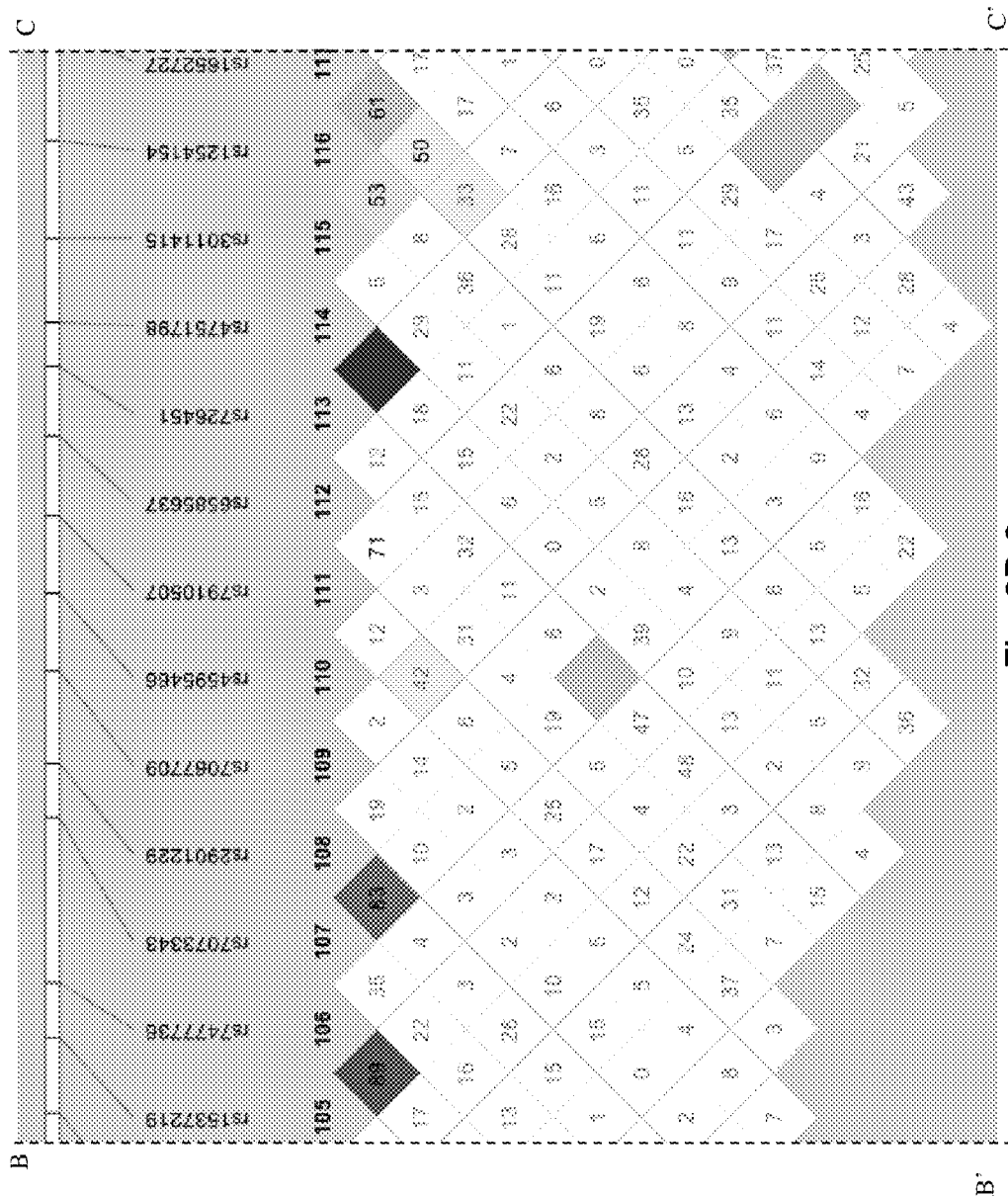
Figures 3, 3D:
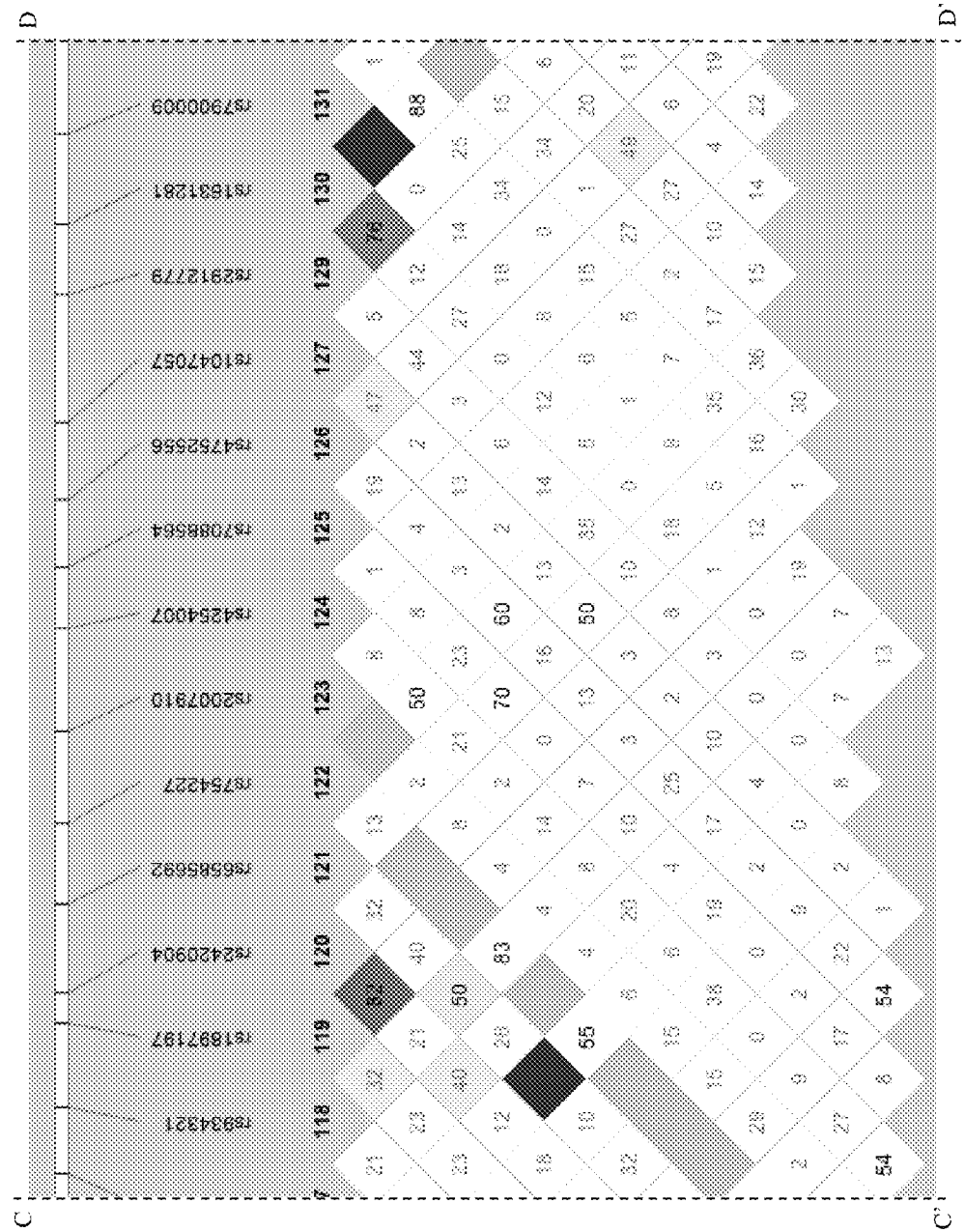

| PART | Analysis | Set of SNPs and sample used | Results |
|---|---|---|---|
| I | htSNP selection | CIDR SNPs on 179 controls | |
| | SNP-SNP LD | CIDR SNPs on 179 controls | FIGS. 3A-3D and 5A-5C |
| | Linkage | CIDR SNPs and htSNPs on 594 ARM families | FIGS. 2, 3 |
| | Allele frequencies | Mendel 5 on 594 ARM families Counting on 179 controls | Table 5 |
| | CCREL | CIDR SNPs on 594 ARM families and 179 controls | Table 5 |
| | GIST | 594 ARM families broken down to 734 typed nuclear families | Table 5 |
| II | Allele frequencies | All SNPs (CIDR and local) Mendel 5 on 323 ARM families Counting 117 controls | Table 6 |
| | CCREL | CIDR SNPs and local SNPs within genes, 323 families and 117 controls | Table 6 |
| | GIST | 323 ARM families broken down to 407 typed nuclear families | Table 6 |
| | SNP-SNP LD | CIDR and local SNPs within genes on 117 unrelated controls | FIG. 6 |
| III | Interaction with GIST | See GIST in I and II above | Tables 5, 6 |
| | Logistic regression | CIDR SNPs, 577 cases and 179 controls | Table 7 |
| | OR and AR | CIDR SNPs, 577 cases and 179 controls Local SNPs, 517 cases (321 | Table 8 |

TABLE 2-continued

Summary of statistical analysis and sample sizes in each part.

| PART | Analysis | Set of SNPs and sample used | Results |
|---|---|---|---|
| | OR and AR of subtypes | from families, 196 sporadic) and 117 controls | Table 9 |
| | CIDR SNPs | CNV: 407 cases and 179 controls<br>GA: 184 cases and 179 controls | |
| | Local SNPs | CNV: 366 cases and 117 controls<br>GA: 159 and 117 controls | |

Part I: Analysis of CIDR SNPs
CIDR SNP Genotyping

To identify the responsible gene on Chromosome 10q26, the Center for Inherited Disease Research (CIDR) carried out high-density custom SNP genotyping of 612 AMD families and 184 unrelated controls with 199 SNPs spanning 13.4 Mbp (26.7 cM) spanning our region of interest. For analysis 196 SNPs were used: three were skipped due to lack of polymorphism in the controls (when this was checked within the family data, the missing allele was extremely rare and only present in heterozygotes). 684 SNPs spanning 45.7 Mbp (47.1 cM) on Chromosome 1q31 were also genotyped; five SNPs were skipped due to lack of polymorphism in the controls—the missing allele was either not present or very rare and only present in heterozygotes in the family data. See Table 3 for the correspondence between allele labels provided herein and the actual alleles, and, for non-synonymous SNPs, the amino acid change.

TABLE 3

Allele labeling. For each marker investigated, allele labels, amino acid change of non-synonymous SNPs, allele frequency in CIDR controls (179) and allele frequency in local controls (117 overlap CIDR controls) and HWE p-value of the exact test.

| SNP | Allele | Label | Amino Acid | CIDR controls | Local controls | HWE P-value |
|---|---|---|---|---|---|---|
| rs6658788 | A | 1 | | 0.511 | 0.483 | 0.58 |
| | G | 2 | | 0.489 | 0.517 | |
| rs1538687 | A | 1 | | 0.693 | 0.658 | 0.41 |
| | G | 2 | | 0.307 | 0.342 | |
| rs1416962 | T | 1 | | 0.648 | 0.607 | 0.44 |
| | C | 2 | | 0.352 | 0.393 | |
| rs946755 | T | 1 | | 0.656 | 0.620 | 0.70 |
| | C | 2 | | 0.344 | 0.380 | |
| rs6428352 | T | 1 | | 0.997 | 0.996 | 1.00 |
| | C | 2 | | 0.003 | 0.004 | |
| rs800292 | A | 1 = Ile | Ile62Val | 0.232 | 0.269 | 0.82 |
| | G | 2 = Val | | 0.768 | 0.731 | |
| rs1061170 | T | 1 = Tyr | Tyr402His | | 0.690 | 0.26 |
| | C | 2 = His | | | 0.310 | |
| rs10922093 | G | 1 | | | 0.295 | 0.66 |
| | A | 2 | | | 0.705 | |
| rs70620 | T | 1 | | 0.173 | 0.150 | 0.28 |
| | C | 2 | | 0.827 | 0.850 | |
| rs1853883 | G | 1 | | 0.511 | 0.568 | 0.45 |
| | C | 2 | | 0.489 | 0.432 | |
| rs1360558 | A | 1 | | 0.397 | 0.389 | 0.70 |
| | G | 2 | | 0.603 | 0.611 | |
| rs955927 | T | 1 | | 0.609 | 0.615 | 0.85 |
| | A | 2 | | 0.391 | 0.385 | |
| rs4350226 | A | 1 | | 0.905 | 0.897 | 0.34 |
| | G | 2 | | 0.095 | 0.103 | |
| rs4752266 | A | 1 | | 0.777 | 0.774 | 0.18 |
| | G | 2 | | 0.223 | 0.226 | |
| rs915394 | T | 1 | | 0.813 | 0.791 | 1.00 |
| | A | 2 | | 0.187 | 0.209 | |
| rs1268947 | G | 1 | | 0.883 | 0.885 | 0.65 |
| | C | 2 | | 0.117 | 0.115 | |
| rs1537576 | G | 1 | | 0.567 | 0.581 | 0.35 |
| | C | 2 | | 0.433 | 0.419 | |
| rs2039488 | T | 1 | | 0.885 | 0.885 | 0.01 |
| | C | 2 | | 0.115 | 0.115 | |
| rs1467813 | T | 1 | | 0.293 | 0.295 | 0.66 |
| | C | 2 | | 0.707 | 0.705 | |
| rs927427 | A | 1 | | 0.464 | 0.487 | 0.10 |
| | G | 2 | | 0.536 | 0.513 | |
| rs4146894 | A | 1 | | 0.466 | 0.474 | 1.00 |
| | G | 2 | | 0.534 | 0.526 | |
| rs12258692 | C | 1 = Pro | Pro233Arg | 1.000 | | — |
| | G | 2 = Arg | | 0.000 | | |
| rs4405249 | T | 1 | | | 0.158 | 1.00 |
| | C | 2 | | | 0.842 | |
| rs1045216 | G | 1 = Ala | Ala320Thr | | 0.573 | 0.46 |
| | A | 2 = Thr | | | 0.427 | |
| rs1882907 | A | 1 | | 0.813 | 0.816 | 0.76 |
| | G | 2 | | 0.187 | 0.184 | |
| rs10490923 | G | 1 = Arg | His3Arg | | 0.859 | 0.39 |
| | A | 2 = His | | | 0.141 | |

TABLE 3-continued

Allele labeling. For each marker investigated, allele labels, amino acid change of non-synonymous SNPs, allele frequency in CIDR controls (179) and allele frequency in local controls (117 overlap CIDR controls) and HWE p-value of the exact test.

| SNP | Allele | Label | Amino Acid | CIDR controls | Local controls | HWE P-value |
|---|---|---|---|---|---|---|
| rs2736911 | C | 1 = Arg | Arg38Ter | | 0.881 | 1.00 |
| | T | 2 = Ter | | | 0.119 | |
| rs10490924 | G | 1 = Ala | Ser69Ala | | 0.807 | 0.21 |
| | T | 2 = Ser | | | 0.193 | |
| rs11538141 | A | 1 = Glu | Gly54Glu | | 0.995 | 1.00 |
| | G | 2 = Gly | | | 0.005 | |
| rs760336 | T | 1 | | 0.520 | 0.526 | 0.58 |
| | C | 2 | | 0.480 | 0.474 | |
| rs763720 | A | 1 | | 0.212 | 0.226 | 0.79 |
| | G | 2 | | 0.788 | 0.774 | |
| rs1803403 | T | 1 = Cys | Cys384Gly | | 0.030 | 1.00 |
| | G | 2 = Gly | | | 0.970 | |

Part II: Analysis of Locally Genotyped SNPs

Local SNP Genotyping—Eight additional SNPs on Chromosome 10 overlying three susceptibility genes, PLEKHA1 (rs12258692, rs4405249 and rs1045216), LOC387715 (rs10490923, rs2736911, rs10490924) and PRSS11 (rs11538141, rs1803403) were genotyped. This genotyping effort included all of the non-synonymous SNPs that have been reported for these genes in the NCBI databases (see FIGS. 1-1 and 1-2). As part of another study (Conley et al. 2005 Candidate gene analysis suggests a role for fatty acid biosynthesis and regulation of the complement system in the etiology of age-related maculopathy), two CFH variants (rs10922093 and rs1061170) were genotyped, which, used here as well. Genotyping of additional SNPs under the GRK5/RGS10 locus is in process. Genotype data for rs12258692, rs1803403 and the newly characterized SNP, rs4405249, one base 3' to rs12258692, was collected by sequencing (Rexagen Corporation, Seattle, Wash.) and analyzed using Sequencher software (Gene Codes Corporation, Ann Arbor, Mich.). Genotype data for rs11538141, rs2736911, rs10490923 and rs10490924 was collected using RFLP. The primers, amplification conditions and restriction endonucleases, where appropriate, can be found in Table 4 for SNPs that were genotyped by sequencing or RFLP.

Genotype data for rs1045216 was collected using a 5' exonuclease Assay-on-Demand TaqMan assay (Applied Biosystems Incorporated, La Jolla, Calif.). Amplification and genotype assignments were conducted using the ABI7000 and SDS 2.0 software (Applied Biosystems). Two unrelated CEPH samples were genotyped for each variant and included on each gel and in each TaqMan tray to assure internal consistency in genotype calls. Additionally, double-masked genotyping assignments were made for each variant, compared, and each discrepancy addressed using raw data or re-genotyping. See Table 3 for the correspondence between allele labels provided herein and the actual alleles, and, for non-synonymous SNPs, the amino acid change.

Part III: Interaction and Odds Ratio (OR) Analysis

Unrelated cases—No unrelated cases were genotyped by CIDR, but 196 unrelated cases were genotyped locally for additional SNPs. For computation of odds ratios and for interaction analyses (see below), a set of unrelated cases were generated by drawing one "Type A" affected person from each family. 321 locally-genotyped families had at least one "Type A" affected person. If a family had more than one "A" affected person, the person that was genotyped the most in rs800292 (CFH), rs1061170 (CFH), rs1537576 (GRK5) and rs4146894 (PLEKHA1) was chosen; if the number of geno-

TABLE 4

Primers, annealing conditions and restriction endonucleases used for genotype data collection for those genotyped via sequencing or RFLP. NA = not applicable

| Variant | Primer Sequences | SEQ ID NO: | Annealing Temp (° C.) | Restriction Enzyme |
|---|---|---|---|---|
| rs11538141 | CAG AGT CGC CAT GCA GAT CC (F) | 1 | 58 | MnlI |
| | CCC GAA GGG CAC CAC GCA CT (R) | 2 | | |
| rs2736911 | GCA CCT TTG TCA CCA CAT TA (F) | 3 | 54 | DraIII |
| | GCC TGA TCA TCT GCA TTT CT (R) | 4 | | |
| rs10490923 | GCA CCT TTG TCA CCA CAT TA (F) | 5 | 54 | HhaI |
| | GCC TGA TCA TCT GCA TTT CT (R) | 6 | | |
| rs10490924 | GCA CCT TTG TCA CCA CAT TA (F) | 7 | 54 | PvuII |
| | GCC TGA TCA TCT GCA TTT CT (R) | 8 | | |
| rs1803403 | TGC TGT CCC TTT GTT GTC TC (F) | 9 | 55 | NA |
| | AGA CAC AGA CAC GCA TCC TG (R) | 10 | | |
| rs12258692 | GCC AGG AAA AGG AAC CTC (F) | 11 | 54 | NA |
| | GCC AGG CAT CAA GTC AGA (R) | 12 | | | typed SNPs did not distinguish between two persons, the person who developed the disease younger was chosen, and otherwise 'A' affected cases were drawn at random from the persons genotyped the most and with the earliest age of onset. 577 CIDR families had at least one "A" affected person, 321 of these families were also genotyped locally, and the 'A' affected person was chosen to be the same as for the local set. For the remaining 256 families, selection was based on the same criteria as above except only rs800292 (CFH), rs1537576 (GRK5), and rs4146894 (PLEKHA1) were used to find the person with the most complete genotyping.

Analysis of Interaction with CFH

Possible interaction between CFH on Chromosome 1 and the genes on Chromosome 10 were investigated by testing with the GIST if SNPs in CFH contributed to the linkage signal on Chromosome 10 and SNPs on Chromosome 10 contributed to the linkage signal on Chromosome 1. This was done by using weights from SNPs on one chromosome and family-based NPLs from the other.

Logistic regression also was used to evaluate different interaction models and test for interaction following the approach described by North et al. (2005) Application of logistic regression to case-control association studies involving two causative loci. Hum Hered 59:79-87. In this approach, many different possible models of the interactions, allowing simultaneously for additive and dominant effects at both of the loci are fit, and relative likelihoods of the different models are compared in order to draw inferences about the most likely and parsimonious model. As previously described (North et al. 2005), the models fit include a MEAN model in which only the mean term is estimated, ADD1, ADD2 and ADD models which assume an additive effect at one or other or both loci, DOM1, DOM2 and DOM models which additionally incorporate dominance effects and two further models, ADDINT and DOMINT, which allow for interactive effects (For more detail, please see North et al. (2005)). Since some pairs of these models are not nested, they were compared using the Akaike information criteria (AIC); in this approach, the model with the lowest AIC is considered the best fitting and the most parsimonious. For these analyses, the program provided by North and his colleagues was used. After some bugs that we discovered had been fixed; the results were double-checked with our own R program. To maximize the sample size, CIDR SNPs in high LD with a highly significant non-synonymous SNP within each gene were chosen. The CIDR SNP rs800292 was chosen to represent rs10611710 (Y402H variant of CFH), and the CIDR SNP rs4146894 represents rs1045216 in PLEKHA1. Similarly, a representative CIDR SNP in GRK5, RGS10, and PRSS11 was selected.

Magnitude of Association

Crude odds ratios was calculated and attributable risk for SNPs was estimated in each gene. The allele that was least frequent in the controls was considered to be the risk allele. Attributable risk was estimated using the formula $AF=100*P*(OR-1)/(1+P*(OR-1)$, where OR is the odds ratio and P is the frequency of the risk allele in the population, as estimated from the controls. This was done using 'Type A' affecteds compared to controls, subjects with CNV compared to controls and subjects with GA compared to controls. To use maximum possible sample size different, but overlapping, samples for CIDR and locally typed SNPs were used. 577 cases drawn from the families and 179 unrelated cases were used for calculating OR and AR of CIDR SNPs but 517 cases (of whom 321 are within the 577 CIDR SNP cases) and 117 controls (all within the 179 CIDR SNP controls) for calculating the OR and AR on the locally genotyped SNPs.

Multiple Testing Issues

In view of very strong evidence from previous studies that there is an ARM-susceptibility locus in the Chromosome 10q26 region, the analyses performed here are aimed at estimating the location of the susceptibility gene, rather than hypothesis testing. Multiple testing issues are most crucial and relevant in the context of hypothesis testing. In estimation, the focus of these studies is simply where the signal is the strongest. In any event, any correction for multiple testing would not alter the rank order of the results. A Bonferroni correction, which does not account for any correlation between tests due to LD, for 196 tests at the 0.05 level would lead to a significance threshold of 0.05/196=0.00026; correlations due to LD would lead to a larger threshold.

Results

Analyses were carried out in three sequential steps. First, the set of data that had been genotyped at CIDR was analyzed. Second, after locally genotyping 8 additional SNPs in the PLEKHA1/LOC387715/PRSS11 region on Chromosome 10, we then analyzed the locally-genotyped data set was analyzed. Allele frequency estimation, testing for Hardy-Weinberg equilibrium (Table 3), CCREL association testing, and GIST testing was carried out on both of these (overlapping) data sets as described above. Third, interaction between the Chromosome 1 and Chromosome 10 regions was analyzed and whether or not the risk differed as a function of the presence of either geographic atrophy or choroidal neovascular membranes was examined.

Part I: Analysis of CIDR SNPs

CIDR Linkage Results

Using the CIDR SNPs and applying the same linkage analysis approaches as in our previous studies (Weeks et al. 2004), the peak of the Sall multipoint curve on Chromosome 10 implicates the GRK5 region ('G' in FIG. 2; rs1537576 in GRK5 had single-point Sall of 1.87 while the maximum single-point Sall of 3.86 occurred at rs555938, 206 kb centromeric of GRK5), but several elevated two-point non-parametric Sall LOD scores and our highest heterogeneity LOD score (HLOD) that draw attention to the PLEKHA1/LOC387715/PRSS11 region ("P" in FIG. 2). In this region, SNP rs4146894 in PLEKHA1 had a two-point Sall of 3.34 and the highest two-point HLOD of 2.66, while SNPs rs760336 and rs763720 in PRSS11 had two-point Sall's of 2.69 and 2.23 respectively. However, the support interval is large (10.06 cM, FIG. 2), and so localization from the linkage analyses alone is rather imprecise.

The effect of failing to take SNP-SNP LD into account was explored by comparing the multipoint scores with all SNPs (FIG. 2-1) to those computed with only the htSNPs (FIG. 2-2). Two of the peaks almost vanish completely (referred to as false peaks, "F"s, in FIG. 2, left panel) when only using H-clust SNPs; interestingly these two peaks lie within haplotype blocks (FIGS. 3A and 3B) while the LD around the highest multi- and two-point LOD scores is low (FIGS. 3C, 3D-1, 3D-2, 3D-3 and 3D-4]), indicating the importance of taking LD into account when performing linkage analysis.

Figures 3, 3D, 4:
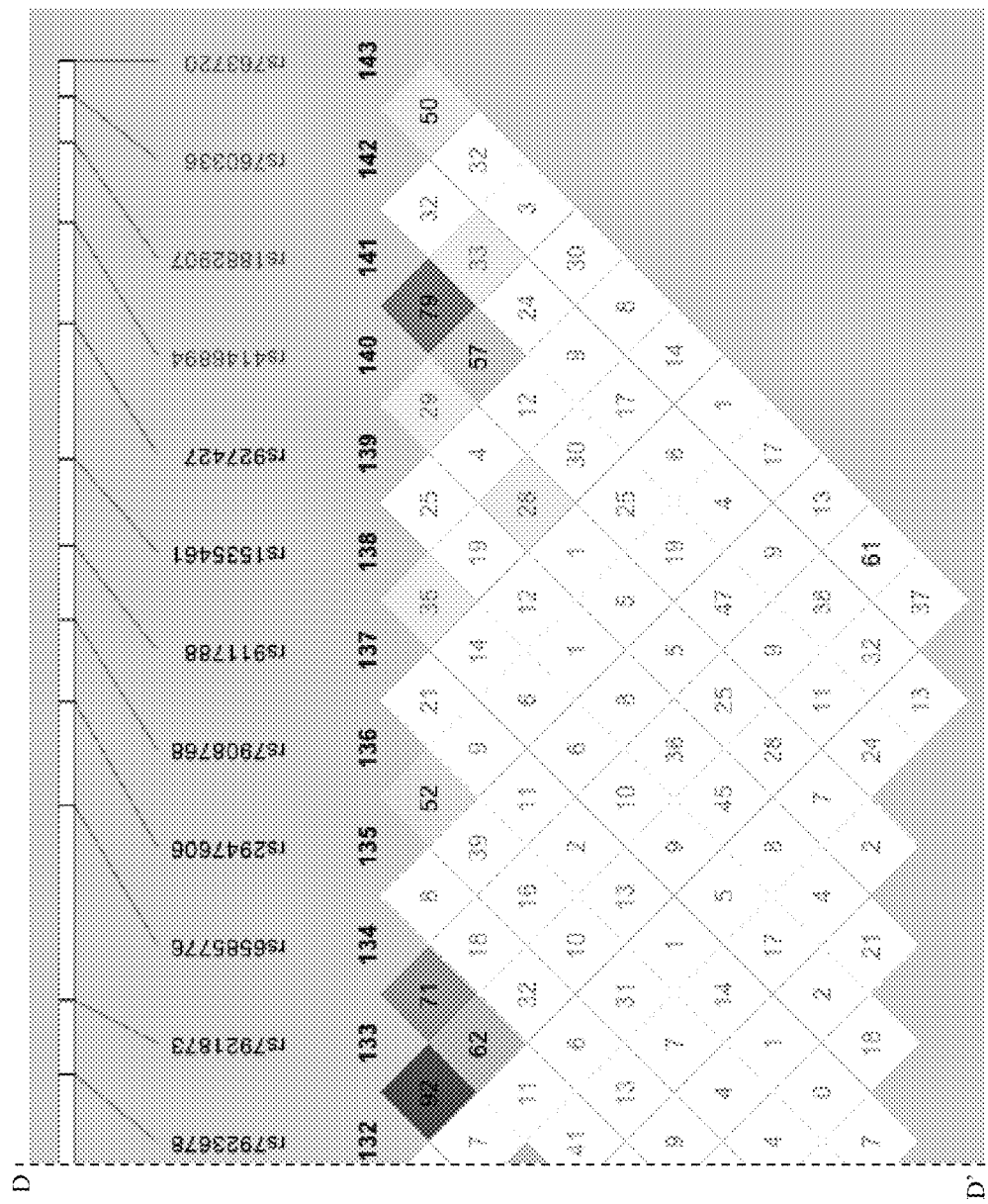
Figures 1, 4:
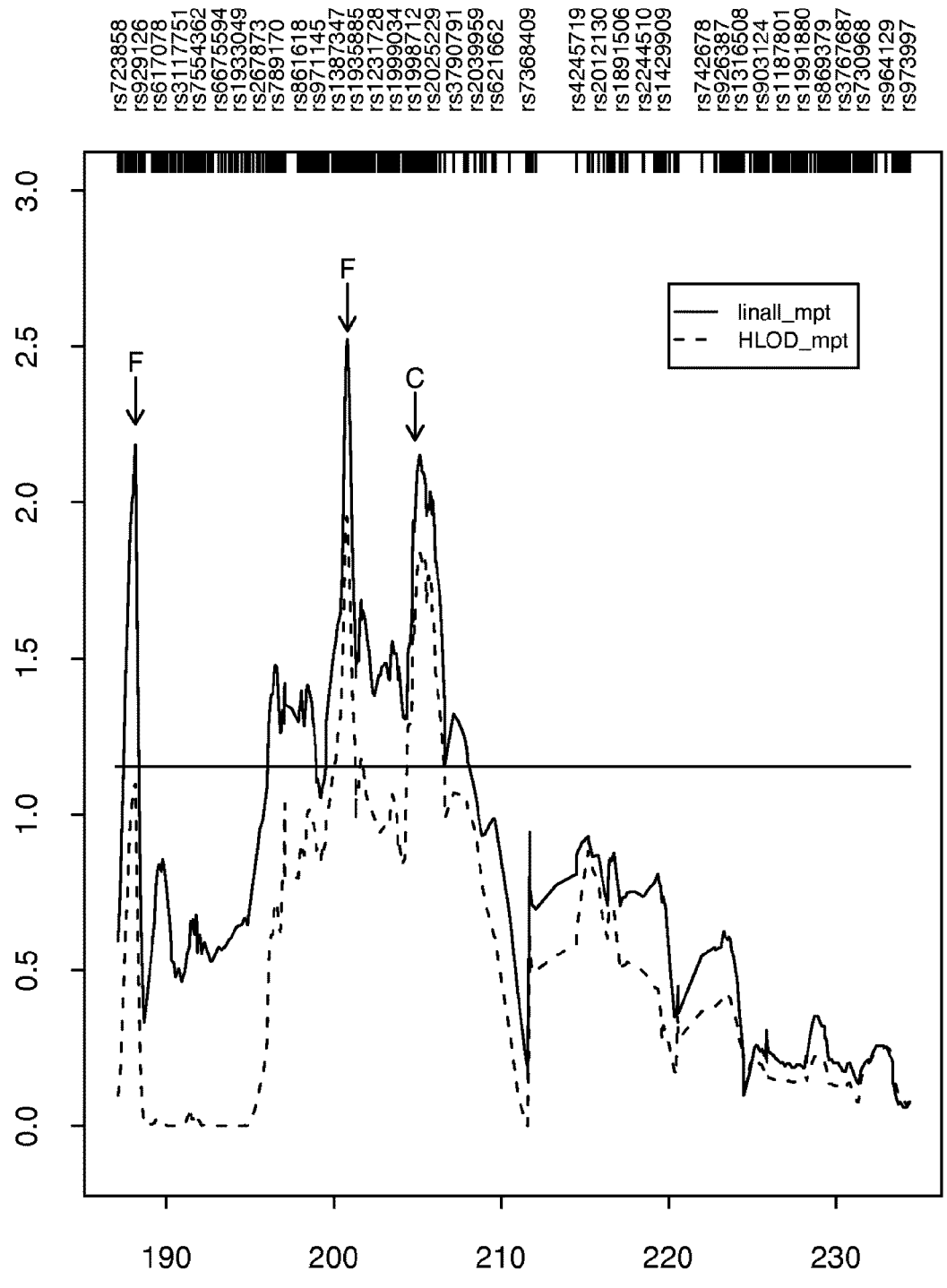
Figures 2, 4:
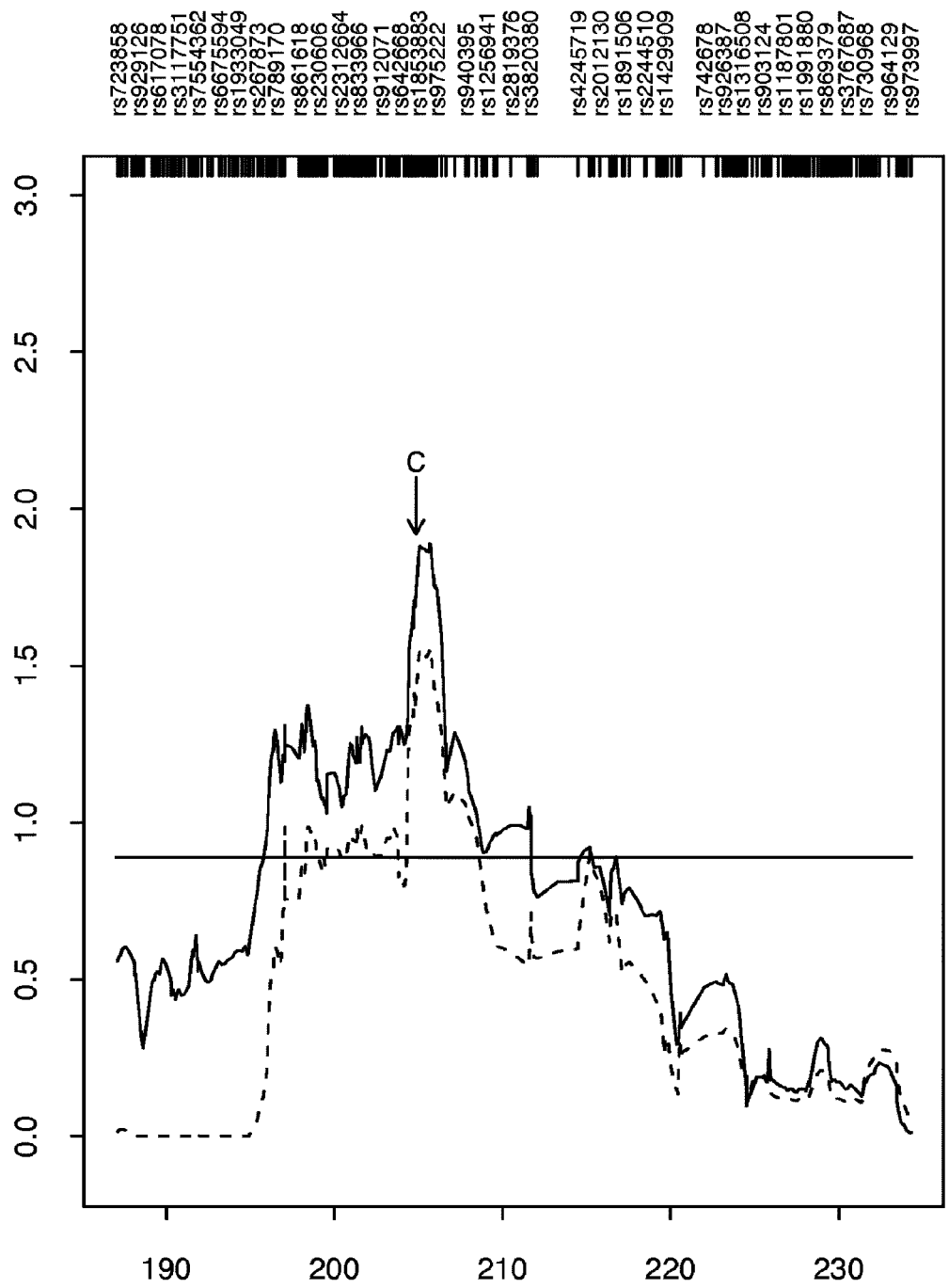

Linkage results on Chromosome 1 gave three peaks with Sall greater than 2, only one of those peaks was observed when analysis was restricted to htSNPs (FIG. 4). This remaining peak overlies the complement factor H (CFH) gene and includes two SNPs with very high two-point Sall and HLOD scores; rs800292, a non-synonymous SNP in CFH, had a Sall of 1.53 and a HLOD of 2.11, while SNP rs1853883, 165 kb telomeric of CFH, had a Sall of 4.06 and a HLOD of 3.49.

Figure 5A:
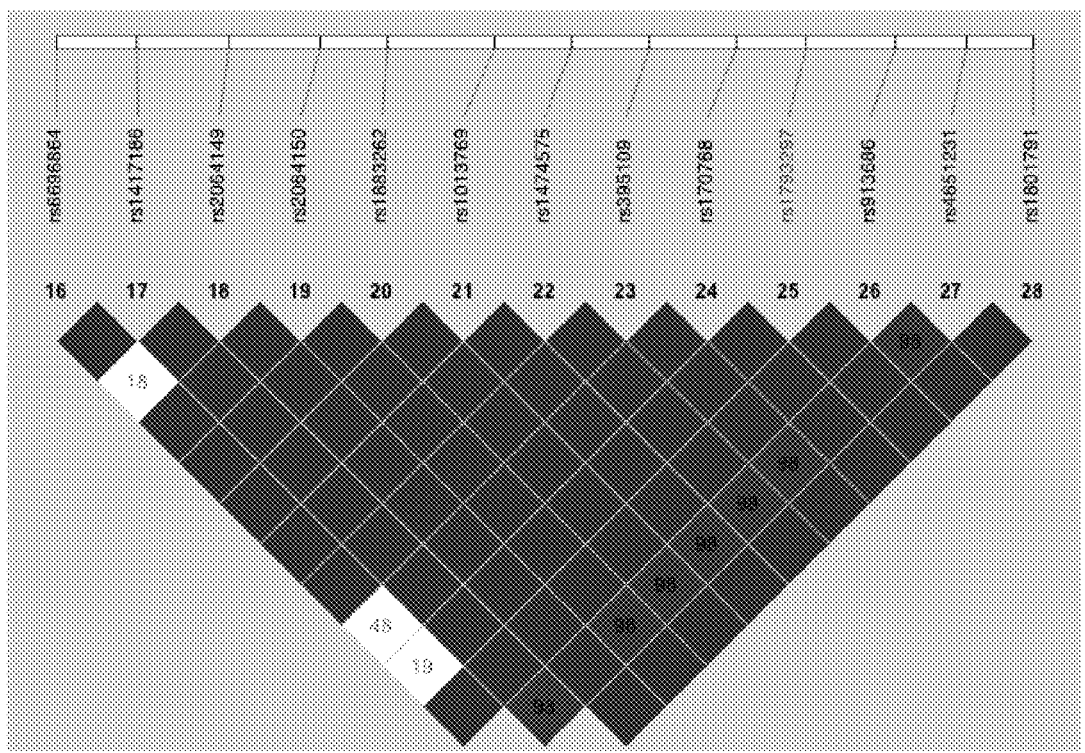
FIGS. 5A-5C provide: linkage disequilibrium patterns on chromosome 1 based on 679 CIDR SNPs and 179 unrelated controls.
Figure 5B:
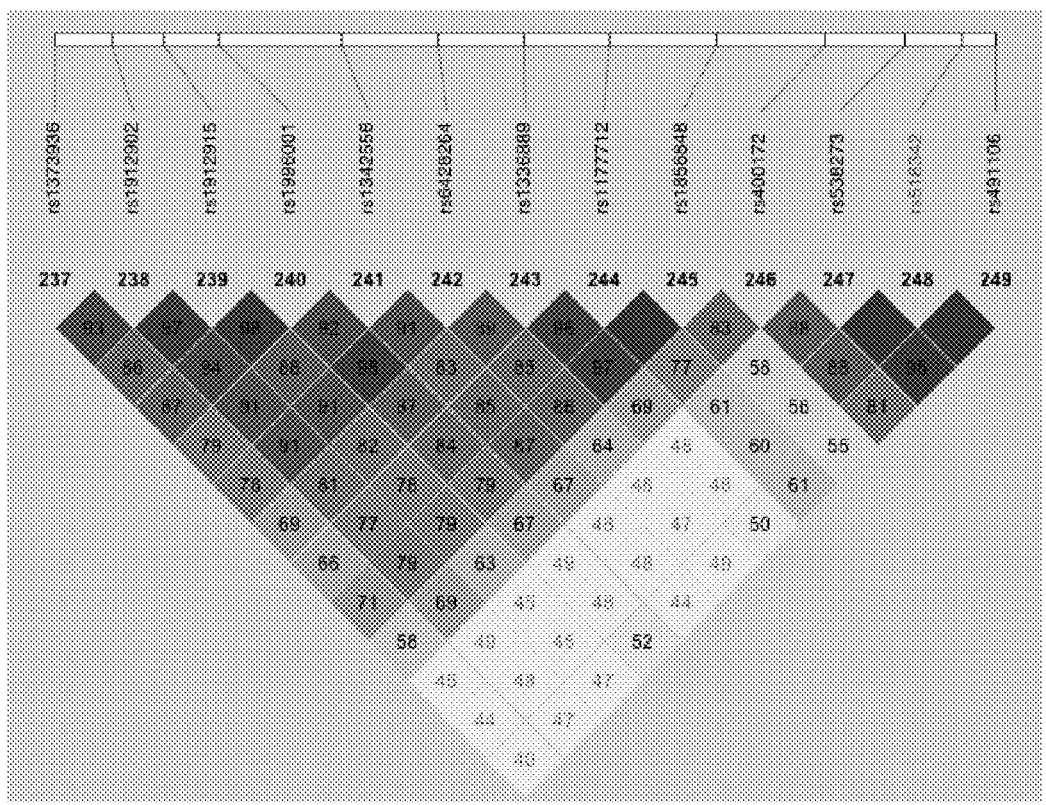
Figure 5C:
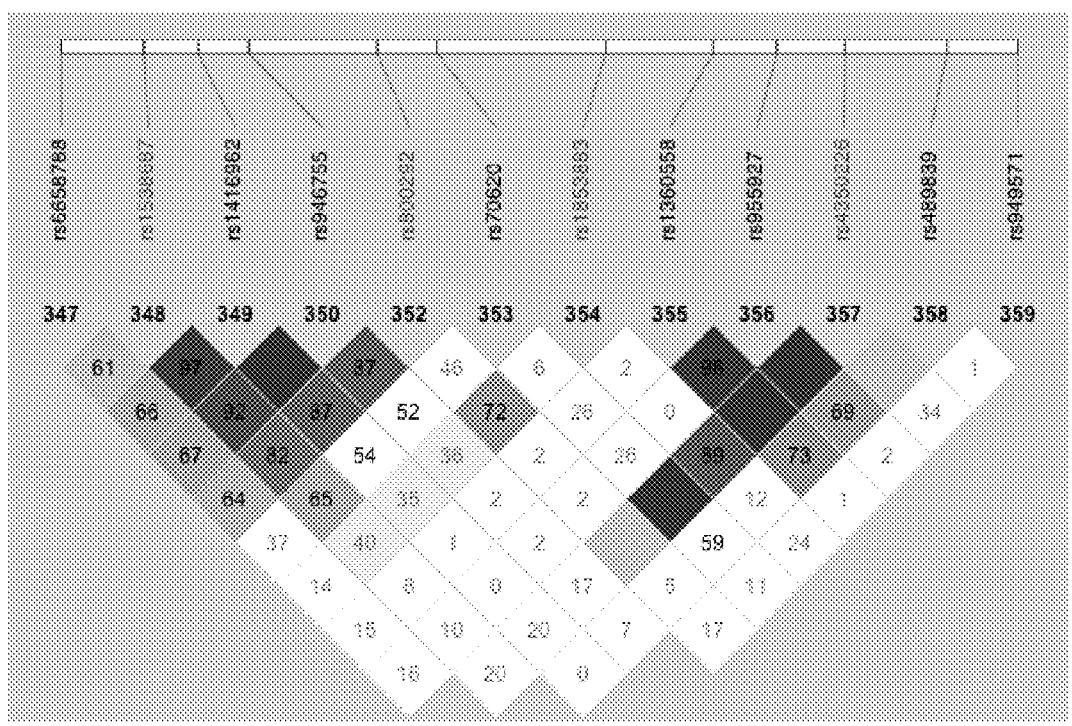
Figure 6A:
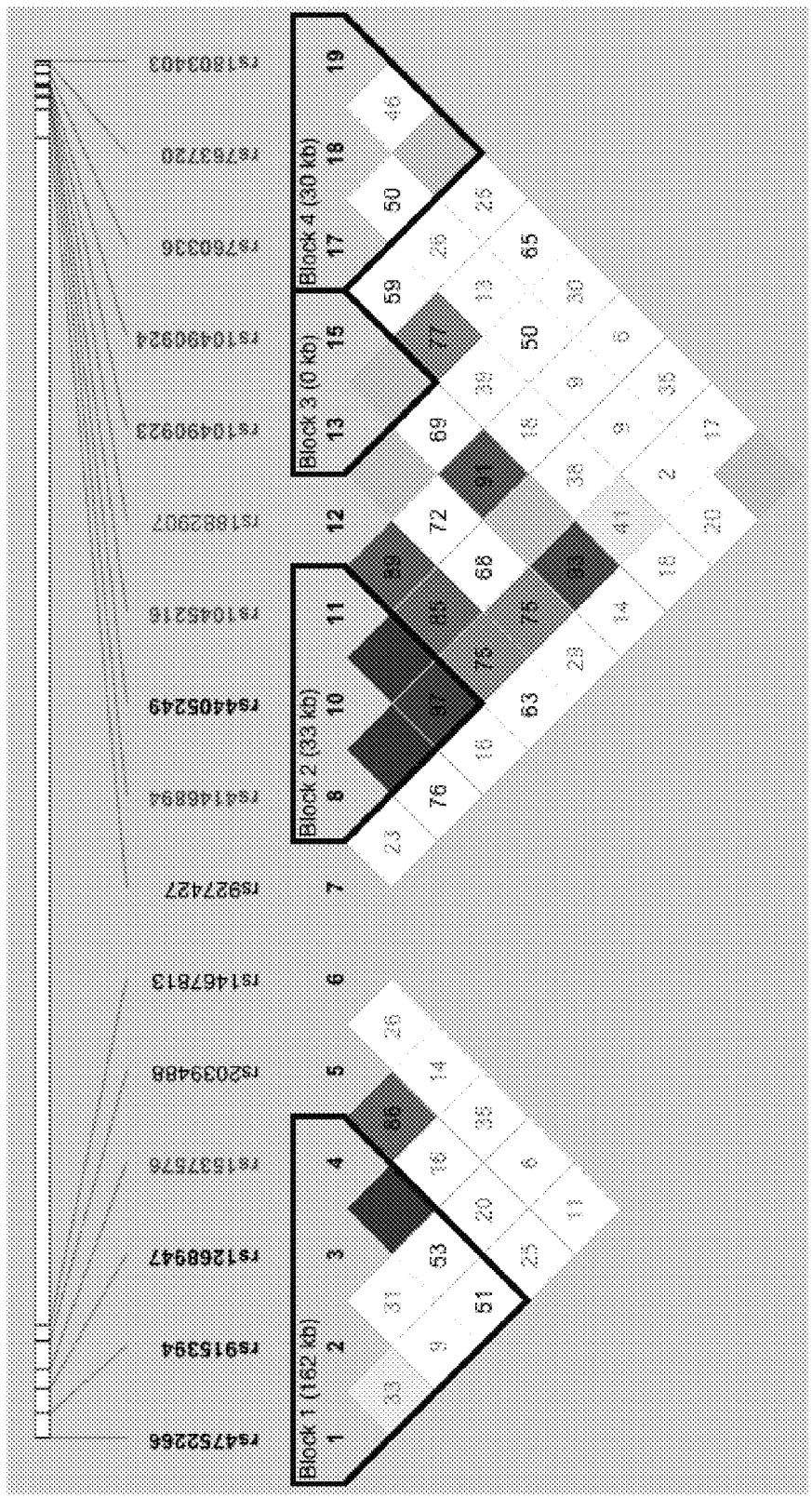
FIGS. 6A and 6B.
Figure 6B:
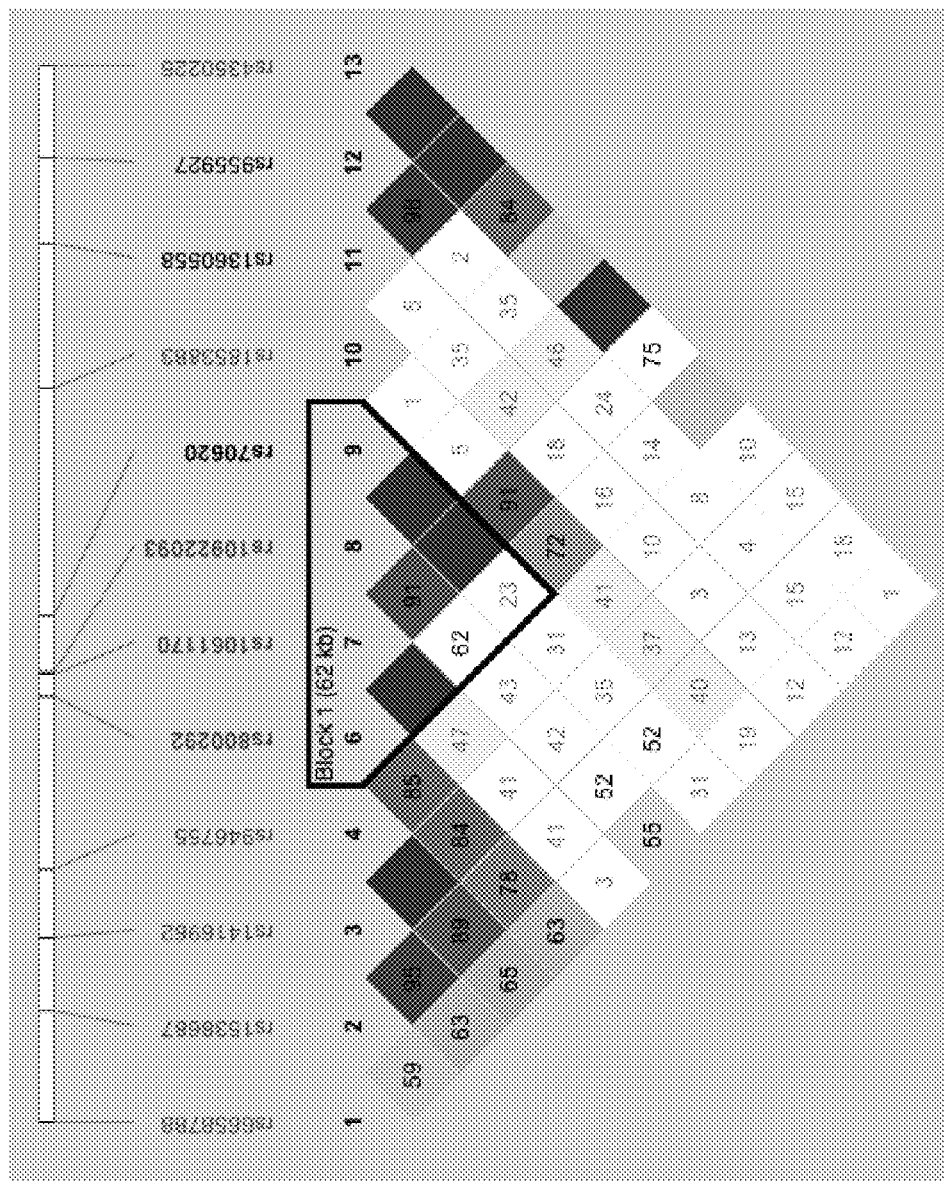

These results strongly support earlier findings of CFH's involvement in ARM (Conley et al. 2005; Edwards et al. 2005; Hageman et al. 2005b A common haplotype in the complement regulatory gene factor H (HF1/CFH) predisposes individuals to age-related macular degeneration. Proc Natl Acad Sci USA.; Haines et al. 2005; Klein et al. 2005; Zareparsi et al. 2005a). The vanishing peaks ('F's in FIG. 4-1) we saw when using all of our SNPs in the linkage analysis are located within strong haplotype blocks (FIGS. 5A and 5B), while the LD under the CFH peak is relatively low (FIG. 5C).

CIDR Association Results

For finer localization than can be obtained by linkage, association analyses was employed (which were very successful in discovering CFH on Chromosome 1). Here, association analyses was performed using the CCREL approach, which permits one to simultaneously use our unrelated controls and all of our related familial cases by appropriately adjusting for the relatedness of the cases. In the CIDR sample on chromosome 10, within our linkage peak, we found a cluster of four adjacent SNPs was identified having very small p-values (rs4146894, rs1882907, rs760336 and rs763720) that overlies three genes: PLEKHA1, LOC387715 and PRSS11. The strongest CCREL results on chromosome 10 were in PLEKHA1 with SNP rs4146894 (Table 5). The moving window haplotype analyses using three SNPs at a time ("haplo3") results in very small p-values across the whole PLEKHA1 to PRSS11 region (Table 5). The association testing also generates some moderately small p-values in the GRK5 region, which is where the highest evidence of linkage occurs.

The CCREL was performed on 56 SNPs spanning the linkage peak on Chromosome 1 and found two highly significant SNPs (rs800292 and rs1853883) that overlie CFH (Table 5). The moving window haplotype analysis using two ("haplo2") and three ("haplo3") SNPs at a time results in extremely low p-values across the whole CFH gene (Table 5) and again supporting earlier findings of strong association of CFH with ARM.

CIDR GIST Results

When GIST testing is carried out on the CIDR data set, the two smallest p-values (0.006, 0.004) in Chromosome 10q26 occur in the GRK5/RGS10 region, while the third smallest p-value (0.008) occurs in PLEKHA1 (Table 5). All four SNPs in the GRK5 gene have small GIST p-values. The GIST results suggest that both GRK5 and PLEKHA1 contribute significantly to the linkage signal on Chromosome 10, and CFH to the linkage signal on Chromosome 1. Neither of the two SNPs in PRSS11 contributes significantly to the linkage signal on Chromosome 10. There was no evidence that these two genes on Chromosome 10 were related to the linkage signal seen on Chromosome 1.

Part II: Analysis of Locally Genotyped SNPs

Local Association Results

After typing additional SNPs locally, the allele and genotype test generate extremely small p-values in each of the three genes PLEKHA1/LOC387715/PRSS11 (Table 6). The moving window haplotype analyses using three SNPs at a time ("haplo3") results in very small p-values across the whole PLEKHA1/LOC387715/PRSS11 region (Table 6). Thus, while association implicates the PLEKHA1/LOC387715/PRSS11 region, it does not distinguish among these genes.

TABLE 5

CCREL, GIST, and allele frequency estimation on families (594) and controls (179) typed at CIDR.

| GENE | SNP | families | controls | allele_test | haplo2 | haplo3 | geno_test | GIST (NPL 10) | GIST (NPL 1) |
|---|---|---|---|---|---|---|---|---|---|
| | rs6658788 | 0.460 | 0.489 | 0.28475 | 0.01470 | 0.00775 | 0.35658 | 0.106 | 0.055 |
| | rs1538687 | 0.234 | 0.307 | 0.00141 | 0.00204 | 0.00675 | 0.00424 | 0.781 | 0.129 |
| | rs1416962 | 0.321 | 0.352 | 0.13492 | 0.34246 | 0.36032 | 0.32841 | 0.566 | 0.019 |
| | rs946755 | 0.317 | 0.344 | 0.16812 | 0.16876 | <u>≤0.0001</u> | 0.32938 | 0.513 | 0.012 |
| | rs6428352 | 0.001 | 0.003 | 1.00000 | <u>≤0.00001</u> | <u>≤0.00001</u> | 1.00000 | | |
| CFH | rs800292 | 0.132 | 0.232 | <u>≤0.00001</u> | <u>≤0.00001</u> | <u>≤0.00001</u> | <u>≤0.00001</u> | 0.437 | <u>0.001</u> |
| CFH | rs70620 | 0.147 | 0.173 | 0.19864 | <u>≤0.00001</u> | <u>≤0.00001</u> | 0.42335 | 0.893 | 0.333 |
| | rs1853883 | 0.630 | 0.489 | <u>≤0.00001</u> | <u>≤0.00001</u> | <u>≤0.00001</u> | <u>≤0.00001</u> | 0.521 | <u>≤0.001</u> |
| | rs1360558 | 0.425 | 0.397 | 0.42543 | 0.67049 | 0.01558 | 0.71496 | 0.183 | 0.296 |
| | rs955927 | 0.416 | 0.391 | 0.43909 | 0.01146 | 0.03400 | 0.73224 | 0.065 | 0.145 |
| | rs4350226 | 0.055 | 0.095 | 0.00250 | 0.00988 | 0.00964 | 0.00266 | 0.171 | 0.242 |
| GRK5 | rs4752266 | 0.220 | 0.223 | 0.78366 | 0.26028 | 0.29913 | 0.04848 | 0.088 | 0.475 |
| GRK5 | rs915394 | 0.214 | 0.187 | 0.12637 | 0.17970 | 0.00350 | 0.31197 | 0.028 | 0.643 |
| GRK5 | rs1268947 | 0.112 | 0.117 | 0.89140 | 0.01174 | 0.01398 | 0.96369 | 0.052 | 0.345 |
| GRK5 | rs1537576 | 0.507 | 0.433 | 0.02286 | 0.01822 | 0.02755 | 0.04309 | 0.006 | 0.251 |
| | rs2039488 | 0.078 | 0.115 | 0.01603 | 0.09338 | 0.12306 | 0.06163 | 0.004 | 0.609 |
| RGS10 | rs1467813 | 0.286 | 0.293 | 0.73004 | 0.77610 | 0.89538 | 0.81737 | 0.539 | 0.582 |
| | rs927427 | 0.514 | 0.464 | 0.05480 | 0.00002 | 0.00001 | 0.05244 | 0.198 | 0.577 |
| PLEKHA1 | rs4146894 | 0.598 | 0.466 | <u>≤0.00001</u> | <u>≤0.00001</u> | <u>≤0.00001</u> | <u>≤0.00001</u> | 0.008 | 0.802 |
| | rs1882907 | 0.127 | 0.187 | 0.00264 | 0.00009 | 0.00004 | 0.00513 | 0.169 | 0.172 |
| PRSS11 | rs760336 | 0.395 | 0.480 | 0.00280 | <u>0.00075</u> | 0.00089 | 0.01281 | 0.232 | 0.581 |
| PRSS11 | rs763720 | 0.295 | 0.212 | <u>0.00043</u> | 0.00059 | 0.00337 | 0.00248 | 0.198 | 0.021 |

Frequency of minor allele in the controls is reported for both controls (estimated by counting) and families (estimated by Mendel version 5), the allele frequency is bolded if the allele frequency differs between controls and families by more than 0.1.
P-values for allele test, haplotype 2 SNP moving window test, haplotype 3 SNP moving window test and genotype test from the CCREL are bolded if ≤0.05 and bolded and underlined if ≤0.001.
GIST P-values using NPL scores from Chromosome 1 and 10 are reported and bolded if less than 0.05, and bolded and underlined if ≤0.001.

TABLE 6

CCREL, GIST, and allele frequency estimation on locally-typed families (323) and controls (117).

| GENE | SNP | families | controls | allele_test | haplo2 | haplo3 | geno_test | GIST (NPL 10) | GIST (NPL 1) |
|---|---|---|---|---|---|---|---|---|---|
|  | rs6658788 | 0.563 | 0.483 | 0.02200 | 0.00052 | 0.00162 | 0.04920 | 0.319 | 0.244 |
|  | rs1538687 | 0.213 | 0.342 | 0.00004 | 0.00043 | 0.00066 | 0.00014 | 0.652 | 0.302 |
|  | rs1416962 | 0.299 | 0.393 | 0.00597 | 0.02623 | 0.02051 | 0.01819 | 0.442 | 0.041 |
|  | rs946755 | 0.295 | 0.380 | 0.01234 | 0.01243 | ≤0.00001 | 0.04531 | 0.409 | 0.040 |
|  | rs6428352 | 0.001 | 0.004 | 1.00000 | ≤0.00001 | ≤0.00001 | 1.00000 |  |  |
| CFH | rs800292 | 0.120 | 0.269 | ≤0.00001 | ≤0.00001 | ≤0.00001 | ≤0.00001 | 0.315 | 0.014 |
| CFH | *rs1061170* | 0.609 | 0.310 | ≤0.00001 | ≤0.00001 | ≤0.00001 | ≤0.00001 | 0.895 | 0.132 |
| CFH | *rs10922093* | 0.210 | 0.295 | 0.00693 | 0.00175 | ≤0.00001 | 0.01723 | 0.360 | 0.327 |
| CFH | rs70620 | 0.148 | 0.150 | 0.91163 | ≤0.00001 | ≤0.00001 | 0.56770 | 0.737 | 0.356 |
|  | rs1853883 | 0.633 | 0.432 | ≤0.00001 | ≤0.00001 | ≤0.00001 | ≤0.00001 | 0.776 | 0.011 |
|  | rs1360558 | 0.437 | 0.389 | 0.18014 | 0.43576 | 0.02079 | 0.37993 | 0.975 | 0.488 |
|  | rs955927 | 0.433 | 0.385 | 0.15343 | 0.01037 | — | 0.36087 | 0.017 | 0.585 |
|  | rs4350226 | 0.050 | 0.103 | 0.00312 | — | — | 0.00373 | 0.228 | 0.174 |
| GRK5 | rs4752266 | 0.223 | 0.226 | 0.81772 | 0.27748 | 0.64917 | 0.08279 | 0.107 | 0.453 |
| GRK5 | rs915394 | 0.228 | 0.209 | 0.34489 | 0.83219 | 0.05560 | 0.62183 | 0.049 | 0.320 |
| GRK5 | rs1268947 | 0.117 | 0.115 | 0.81975 | 0.02748 | 0.02192 | 0.78965 | 0.049 | 0.689 |
| GRK5 | rs1537576 | 0.497 | 0.419 | 0.02604 | 0.02232 | 0.05636 | 0.06334 | 0.012 | 0.023 |
|  | rs2039488 | 0.083 | 0.115 | 0.11177 | 0.42428 | — | 0.42399 | 0.025 | 0.358 |
| RGS10 | rs1467813 | 0.293 | 0.295 | 0.86608 | — | — | 0.85954 | 0.506 | 0.492 |
|  | rs927427 | 0.506 | 0.487 | 0.56710 | 0.00056 | 0.00083 | 0.42264 | 0.306 | 0.625 |
| PLEKHA1 | rs4146894 | 0.611 | 0.474 | 0.00004 | 0.00012 | 0.00053 | 0.00024 | 0.006 | 0.737 |
| PLEKHA1 | *rs12258692* | 0.008 | 0.000 | 1.00000 | 0.54750 | 0.00018 | 1.00000 |  |  |
| PLEKHA1 | *rs4405249* | 0.139 | 0.158 | 0.39378 | 0.00026 | 0.00280 | 0.33118 | 0.003 | 0.345 |
| PLEKHA1 | *rs1045216* | 0.289 | 0.427 | 0.00004 | 0.00036 | 0.00001 | 0.00026 | 0.068 | 0.825 |
|  | rs1882907 | 0.131 | 0.184 | 0.01761 | 0.00140 | 0.01099 | 0.04401 | 0.017 | 0.372 |
| LOC387715 | *rs10490923* | 0.089 | 0.141 | 0.02112 | 0.05024 | ≤0.00001 | 0.03415 | 0.086 | 0.251 |
| LOC387715 | *rs2736911* | 0.121 | 0.119 | 0.71668 | ≤0.00001 | ≤0.00001 | 0.64230 | 0.312 | 0.968 |
| LOC387715 | *rs10490924* | 0.475 | 0.193 | ≤0.00001 | ≤0.00001 | ≤0.00001 | ≤0.00001 | 0.018 | 0.327 |
| PRSS11 | *rs11538141* | 0.004 | 0.005 | 1.00000 | 0.00726 | 0.01676 | 1.00000 |  |  |
| PRSS11 | rs760336 | 0.373 | 0.474 | 0.00527 | 0.01386 | 0.00036 | 0.01396 | 0.479 | 0.683 |
| PRSS11 | rs763720 | 0.296 | 0.226 | 0.01645 | 0.00016 |  | 0.03899 | 0.305 | 0.451 |
| PRSS11 | rs1803403 | 0.118 | 0.030 | 0.00009 |  |  | 0.00022 | 0.714 | 0.778 |

The frequency of minor allele in the controls is reported for both controls (estimated by counting) and families (estimated by Mendel version 5), the allele frequency is bolded if the allele frequency differs between controls and families by more than 0.1.
P-values for allele test, haplotype 2 SNP moving window test, haplotype 3 SNP moving window test and genotype test from the CCREL are bolded if <= 0.05 and bolded and underlined if <= 0.001.
GIST P-values using NPL scores from chromosome 1 and 10 are reported and bolded if less than 0.05. SNPs in italics are the locally typed SNPs.

Local GIST Results

Of the three genes PLEKHA1/LOC387715/PRSS11, GIST most strongly implicates PLEKHA1 (Table 6). It also generates a small p-value in LOC387715 (rs10490924), but this SNP is in high LD with the PLEKHA1 SNPs (see FIG. 6A). When the locally-typed data set is used, GIST does not generate any significant results in PRSS11, similar to the non-significant results observed above in the larger CIDR sample. This implies that PLEKHA1 (or a locus in strong LD with it) is the most likely to be involved in AMD, and therefore LOC387715 remains a possibility.

For a fair assessment of which SNP accounts for the linkage signal across the region, the NPLs were computed using only the locally-genotyped families. This permits comparison of the PLEKHA1/LOC387715/PRSS11 results in Table 6 directly to the GRK5/RGS10 results. On the locally-typed data set, the GRK5 GIST results are also interesting, with modestly smallish p-values of the same magnitude as the p-values obtained from applying GIST to CFH (Table 6). However, note that the p-values are not as small as those seen when the CIDR data set was analyzed. Since all of the SNPs in the GRK5 region are CIDR SNPs, this difference is solely a function of sample size, as the locally-typed data set is smaller than the CIDR data set (See Table 2).

Part III: Interaction and Odds Ratio (OR) Analyses
GIST Results

No strong evidence of an interaction between the Chromosome 1 and Chromosome 10 regions were seen with the GIST test. When using the CIDR data set, to test if SNPs on chromosome 10 contribute to the linkage signal on Chromosome 1 (Table 5 'GIST (NPL 1)'), only rs763720 in PRSS11 gives p-value less than 0.05, however rs763720 does not contribute significantly to the linkage signal on Chromosome 10, making this p-value less convincing. When the local data set only was used, one GRK5 variant (rs1537576), which was not significant in the larger CIDR data set, gives p-value less than 0.05. Similarly, no evidence was seen that SNPs within CFH contribute to the linkage signal on Chromosome 10, only one SNP (rs955927) gives p-value less than 0.05, this SNP is however not in CFH and not in strong LD (see FIG. 6B) with any SNPs in the CFH gene.

Logistic Regression Results

The logistic regression suggests that an additive model including both variants from CFH and PLEKHA1 is the best model for predicting case-control status; this indicates that both genes are important to the ARM phenotype. The AIC criteria also gives that an additive model including an additive interaction term is the next best model (Table 7), however the interaction term is not significant (p-value=0.71). Similar results were obtained for interaction between CFH and PRSS11, where additive model including both variants appears to be the best model. Within the GRK5/RGS10 region, a model with the CFH SNP alone is the best fitting model, suggesting that the prediction of case-control status with CFH genotype does not improve by adding either the GRK5 or RGS10 variant to the model.

TABLE 7

Results of fitting two-locus models by logistic regression.
Locus 1: rs800292 (CFH)

| Locus 2 | Model | AIC | AIC Diff |
|---|---|---|---|
| rs1537576 (GRK5) | MEAN | 822.5 | 23.65 |
| | ADD1 | 798.8 | 0 |
| | ADD2 | 821.2 | 22.35 |
| | ADD | 799.1 | 0.26 |
| | DOM1 | 799.7 | 0.91 |
| | DOM2 | 820.1 | 21.24 |
| | DOM | 799.2 | 0.37 |
| | ADDINT | 800.9 | 2.07 |
| | ADDDOM | 802.1 | 3.25 |
| | DOMINT | 803.9 | 5.07 |
| rs1467813 (RGS10) | MEAN | 821.9 | 23.53 |
| | ADD1 | 798.4 | 0 |
| | ADD2 | 823.6 | 25.25 |
| | ADD | 800.3 | 1.92 |
| | DOM1 | 799.3 | 0.91 |
| | DOM2 | 825.2 | 26.79 |
| | DOM | 802.6 | 4.23 |
| | ADDINT | 801.3 | 2.93 |
| | ADDDOM | 804.9 | 6.54 |
| | DOMINT | 805.2 | 6.83 |
| rs4146894 (PLEKHA1) | MEAN | 823.02 | 49.26 |
| | ADD1 | 799.24 | 25.49 |
| | ADD2 | 801.47 | 27.71 |
| | ADD | 773.76 | 0 |
| | DOM1 | 800.16 | 26.41 |
| | DOM2 | 803.44 | 29.68 |
| | DOM | 776.44 | 2.68 |
| | ADDINT | 775.62 | 1.87 |
| | ADDDOM | 779.85 | 6.09 |
| | DOMINT | 778.26 | 4.5 |
| rs760336 (PRSS11) | MEAN | 821.9 | 27.32 |
| | ADD1 | 798.4 | 3.78 |
| | ADD2 | 817.1 | 22.54 |
| | ADD | 794.6 | 0 |
| | DOM1 | 799.3 | 4.69 |
| | DOM2 | 819 | 24.37 |
| | DOM | 796.7 | 2.14 |
| | ADDINT | 796 | 1.43 |
| | ADDDOM | 802.1 | 7.46 |
| | DOMINT | 803.4 | 8.75 |

AIC of each model, and difference of the AIC from the best fitting model. Model definitions are in the text.

Odds Ratios and Attributable Risk

The magnitude of association was estimated by calculating odds ratio (OR) and attributable risk (AR); the observed significant associations (Table 8) were consistent with the results from the CCREL tests in parts I and II. The two most significant SNPs in the PLEKHA1/LOC387715 region occur at SNPs rs4146894 (PLEKHA1) and rs10490924 (LOC387715); these two tests are highly correlated since the LD between those SNPs is very high (D'=0.93) (see FIG. 6A). The third most significant SNP (rs1045216) in the Chromosome 10 region is a non-synonymous SNP in PLEKHA1 and in high LD with both rs4146894 (D'=97) and rs10490924 (D'=0.91).

TABLE 8

Odds ratios (OR), attributable risks (AR) and simulated p-values from a chi-squared test using 10000 replicates.

| GENE | SNP.allele | Dominant ((RR + RN) vs NN) | | | | | Heterozygotes (RN vs NN) | | Recessive (RR vs (RN + NN)) | | | | | Homozygotes (RN vs NN) | |
|---|---|---|---|---|---|---|---|---|---|---|---|---|---|---|---|
| | | OR | 95% CI | | AR | p-value | OR | AR | OR | 95% CI | | AR | p-value | OR | AR |
| | rs6658788.2 | 0.83 | 0.57 | 1.22 | −14.04 | 0.3909 | 1.09 | 2.69 | 1.01 | 0.68 | 1.5 | 0.21 | 1 | 0.88 | −5.92 |
| | rs1538687.2 | 0.68 | 0.49 | 0.95 | −19.38 | 0.023 | 0.5 | −11.74 | 0.42 | 0.23 | 0.78 | −6.52 | 0.0068 | 0.38 | −12.42 |
| | rs1416962.2 | 0.84 | 0.6 | 1.18 | −10.02 | 0.3418 | 0.89 | −2.57 | 0.82 | 0.49 | 1.38 | −2.31 | 0.5002 | 0.77 | −5.74 |
| | rs946755.2 | 0.8 | 0.57 | 1.13 | −12.52 | 0.232 | 1 | 0.04 | 0.9 | 0.53 | 1.52 | −1.24 | 0.7816 | 0.81 | −4.34 |
| | rs6428352.2 | — | | | — | | — | — | — | | | — | | — | — |
| CFH | rs800292.1 | 0.43 | 0.3 | 0.62 | −30.01 | <0.0001 | 0.48 | −23.85 | 0.15 | 0.05 | 0.45 | −4.98 | 0.0001 | 0.12 | −8.19 |
| CFH | *rs1061170.2* | 5.29 | 3.35 | 8.35 | 68.2 | <0.0001 | 2.66 | 28.55 | 4.57 | 2.48 | 8.42 | 30.06 | <0.0001 | 10.05 | 63.72 |
| CFH | *rs10922093.1* | 0.59 | 0.39 | 0.88 | −25.61 | 0.0111 | 0.63 | −19.65 | 0.5 | 0.24 | 1.04 | −4.98 | 0.0736 | 0.41 | −10.14 |
| CFH | rs70620.1 | 0.83 | 0.57 | 1.19 | −5.64 | 0.3366 | 0.85 | −4.29 | 0.67 | 0.27 | 1.68 | −1.3 | 0.4525 | 0.64 | −1.93 |
| | rs1853883.2 | 2.67 | 1.78 | 4.01 | 54.41 | <0.0001 | 1.65 | 19.21 | 2.08 | 1.43 | 3.02 | 22.06 | 0.0003 | 3.55 | 55.04 |
| | rs1360558.1 | 1.16 | 0.82 | 1.65 | 9.12 | 0.414 | 1.1 | 5.39 | 1.25 | 0.8 | 1.96 | 3.94 | 0.3774 | 1.32 | 9.01 |
| | rs955927.2 | 1.13 | 0.79 | 1.6 | 7.5 | 0.5303 | 1.28 | 6.35 | 1.31 | 0.83 | 2.08 | 4.53 | 0.2588 | 1.36 | 9.38 |
| | rs4350226.2 | 0.51 | 0.32 | 0.81 | −9.68 | 0.0038 | 0.27 | −4.76 | 0.16 | 0.01 | 1.74 | −0.95 | 0.142 | 0.14 | −1.16 |
| GRK5 | rs4752266.2 | 0.88 | 0.62 | 1.23 | −5.57 | 0.4325 | 3.27 | 10.68 | 2.81 | 0.98 | 8.04 | 3.89 | 0.0457 | 2.56 | 5.51 |
| GRK5 | rs915394.2 | 1.28 | 0.9 | 1.82 | 8.91 | 0.1543 | 1.35 | 2.73 | 1.56 | 0.58 | 4.14 | 1.53 | 0.3892 | 1.68 | 2.72 |
| GRK5 | rs1268947.2 | 1.05 | 0.7 | 1.57 | 1.06 | 0.841 | 1.24 | 1.82 | 1.27 | 0.35 | 4.55 | 0.45 | 0.7761 | 1.28 | 0.58 |
| GRK5 | rs1537576.2 | 1.59 | 1.11 | 2.29 | 27.95 | 0.0109 | 0.89 | −3.74 | 1.08 | 0.71 | 1.62 | 1.59 | 0.7579 | 1.47 | 15.14 |
| | rs2039488.2 | 0.7 | 0.45 | 1.07 | −6.5 | 0.1067 | 0.23 | −11.98 | 0.19 | 0.04 | 0.79 | −2.33 | 0.0242 | 0.18 | −2.85 |
| RGS10 | rs1467813.1 | 0.96 | 0.69 | 1.35 | −1.84 | 0.8645 | 1.01 | 0.42 | 0.77 | 0.42 | 1.38 | −2.27 | 0.4265 | 0.77 | −3.76 |
| | rs927427.1 | 1.09 | 0.74 | 1.62 | 6.57 | 0.6172 | 0.94 | −4.66 | 1.67 | 1.09 | 2.56 | 10.73 | 0.0201 | 1.6 | 19.91 |
| PLEKHA1 | rs4146894.1 | 2.22 | 1.49 | 3.31 | 46.78 | 0.0002 | 1.77 | 33.08 | 2.21 | 1.49 | 3.29 | 20.46 | <0.0001 | 3.31 | 49.88 |
| PLEKHA1 | *rs12258692.2* | — | | | — | | — | — | — | | | — | | — | — |
| PLEKHA1 | *rs4405249.1* | 0.62 | 0.33 | 1.15 | −12.96 | 0.1692 | 0.61 | −12.69 | 0.87 | 0.1 | 7.56 | −0.23 | 1 | 0.77 | −0.57 |
| PLEKHA1 | *rs1045216.2* | 0.48 | 0.32 | 0.74 | −51.23 | 0.0005 | 0.49 | −18.27 | 0.37 | 0.21 | 0.65 | −14.3 | 0.0003 | 0.28 | −35.68 |
| | rs1882907.2 | 0.58 | 0.4 | 0.84 | −16.73 | 0.0026 | 0.44 | −5.79 | 0.31 | 0.1 | 0.97 | −2.37 | 0.0438 | 0.27 | −3.65 |
| LOC387715 | *rs10490923.2* | 0.53 | 0.31 | 0.9 | −13.27 | 0.0239 | 0.34 | −9.01 | 0.22 | 0.04 | 1.09 | −2.51 | 0.0809 | 0.2 | −3.32 |
| LOC387715 | *rs2736911.2* | 0.72 | 0.42 | 1.21 | −6.92 | 0.2552 | 1.47 | 1.99 | 1.1 | 0.13 | 9.53 | 0.1 | 1 | 1.03 | 0.04 |
| LOC387715 | *rs10490924.2* | 5.03 | 3.2 | 7.91 | 57.11 | <0.0001 | 2.72 | 22.76 | 5.75 | 2.46 | 13.46 | 21.2 | <0.0001 | 10.57 | 42.71 |
| PRSS11 | *rs11538141.2* | — | | | — | | — | — | — | | | — | | — | — |
| PRSS11 | rs760336.2 | 0.64 | 0.44 | 0.93 | −35.37 | 0.013 | 0.8 | −6.95 | 0.69 | 0.46 | 1.03 | −7.95 | 0.0773 | 0.55 | −26.43 |

TABLE 8-continued

Odds ratios (OR), attributable risks (AR) and simulated p-values from a chi-squared test using 10000 replicates.

| GENE | SNP.allele | Dominant ((RR + RN) vs NN) | | | | | Heterozygotes (RN vs NN) | | Recessive (RR vs (RN + NN)) | | | | | Homozygotes (RN vs NN) | |
|---|---|---|---|---|---|---|---|---|---|---|---|---|---|---|---|
| | | OR | 95% CI | | AR | p-value | OR | AR | OR | 95% CI | | AR | p-value | OR | AR |
| PRSS11 | rs763720.1 | 1.69 | 1.2 | 2.38 | 21.24 | 0.0018 | 1.55 | 16.95 | 2.63 | 1.1 | 6.25 | 5.17 | 0.0277 | 3.16 | 10.14 |
| PRSS11 | *rs1803403.1* | 2.98 | 1.25 | 7.06 | 10.51 | 0.0093 | 2.98 | 10.51 | — | — | — | — | — | — | — |

"Type A" affecteds are compared to controls.
OR and AR values are bolded and underlined if corresponding p-values are less than 0.001 and bolded if less than 0.05.
SNP.allele denotes the SNP measured and the risk allele (minor allele in controls).
RR denotes homozygotes for the risk allele,
RN denotes heterozygotes for the risk allele and
NN denotes homozygotes for the normal allele.
SNPs in italics are the locally typed SNPs.

We obtained similar results and similar OR and AR values (Table 8) as others have reported for the CFH gene. The three most significant SNPs were rs1061170 (Y402H variant), rs800292 (in CFH) and rs1853883 (in strong LD with rs1061170, D'=91).

The magnitude of the association seen within PLEKHA1/LOC387715 is very similar to the level of association seen between CFH and ARM; both loci result in extremely low p-values (p-values<0.0001). The OR and AR values were also similar, within CFH the dominant OR was 5.29 (95% CI 3.35-8.35) and within PLEKHA1/LOC387715 it was 5.03 (95% CI 3.2-7.91), the dominant AR for CFH and PLEKHA1/LOC387715 was 68% and 57%, respectively.

Sub-Phenotype Analyses

We estimated odds ratios and attributable risk in cases with exudative disease vs. controls, and cases with geographic atrophy versus controls (Table 9). Odds ratios and corresponding p-values yield similar findings as the allele test of CCREL (Table 5 and 6). We found no major differences between the odds ratios for the presence of either geographic atrophy or choroidal neovascular membranes.

TABLE 9

OR and AR from analysis of ARM subtypes.

| GENE | SNP.allele | Subtype | Dominant ((RR + RN) vs NN) | | | | | Heterozygotes (RN vs NN) | |
|---|---|---|---|---|---|---|---|---|---|
| | | | OR | 95% CI | | AR | p-value | OR | AR |
| | rs6658788.2 | CNV | 0.84 | 0.56 | 1.25 | −13.41 | 0.36706 | 1.21 | 6.19 |
| | rs6658788.2 | GA | 0.88 | 0.55 | 1.4 | −9.92 | 0.63064 | 1.07 | 2.18 |
| | rs1538687.2 | CNV | 0.71 | 0.5 | 1.02 | −17.04 | 0.07499 | 0.54 | −10.68 |
| | rs1538687.2 | GA | 0.62 | 0.41 | 0.94 | −23.86 | 0.0317 | 0.56 | −10.14 |
| | rs1416962.2 | CNV | 0.88 | 0.61 | 1.25 | −7.7 | 0.41676 | 1.02 | 0.46 |
| | rs1416962.2 | GA | 0.77 | 0.51 | 1.17 | −15.12 | 0.24708 | 0.69 | −7.53 |
| | rs946755.2 | CNV | 0.84 | 0.59 | 1.2 | −9.81 | 0.37326 | 1.14 | 2.86 |
| | rs946755.2 | GA | 0.73 | 0.48 | 1.11 | −18.18 | 0.17258 | 0.79 | −4.46 |
| | rs6428352.2 | CNV | — | — | — | — | — | — | — |
| | rs6428352.2 | GA | — | — | — | — | — | — | — |
| CFH | rs800292.1 | CNV | 0.48 | 0.33 | 0.7 | −26.97 | 0.0002 | 0.53 | −21.4 |
| CFH | rs800292.1 | GA | 0.39 | 0.25 | 0.62 | −33.02 | 0.0002 | 0.44 | −26.29 |
| CFH | *rs1061170.2* | CNV | 5.25 | 3.22 | 8.55 | 68 | <0.0001 | 2.37 | 24.74 |
| CFH | *rs1061170.2* | GA | 5.76 | 3.17 | 10.47 | 70.42 | <0.0001 | 3.31 | 35.78 |
| CFH | *rs10922093.1* | CNV | 0.56 | 0.37 | 0.85 | −28.05 | 0.0083 | 0.61 | −20.84 |
| CFH | *rs10922093.1* | GA | 0.51 | 0.31 | 0.84 | −32.2 | 0.0089 | 0.58 | −23.06 |
| CFH | rs70620.1 | CNV | 0.77 | 0.52 | 1.14 | −7.45 | 0.23338 | 0.8 | −5.9 |
| CFH | rs70620.1 | GA | 0.72 | 0.45 | 1.15 | −9.48 | 0.18978 | 0.78 | −6.4 |
| | rs1853883.2 | CNV | 2.52 | 1.64 | 3.89 | 52.14 | 0.0002 | 1.5 | 15.44 |
| | rs1853883.2 | GA | 3.54 | 1.97 | 6.36 | 64.51 | <0.0001 | 1.95 | 25.93 |
| | rs1360558.1 | CNV | 1.1 | 0.76 | 1.59 | 5.96 | 0.64364 | 1.04 | 2.29 |
| | rs1360558.1 | GA | 1.16 | 0.75 | 1.79 | 9.09 | 0.57904 | 1.13 | 6.6 |
| | rs955927.2 | CNV | 1.12 | 0.78 | 1.63 | 7.31 | 0.51105 | 1.32 | 7.01 |
| | rs955927.2 | GA | 1.08 | 0.7 | 1.67 | 5 | 0.74163 | 1.18 | 4.02 |
| | rs4350226.2 | CNV | 0.55 | 0.34 | 0.91 | −8.65 | 0.0209 | — | — |
| | rs4350226.2 | GA | 0.52 | 0.28 | 0.96 | −9.46 | 0.0462 | — | — |
| GRK5 | rs4752266.2 | CNV | 0.93 | 0.65 | 1.34 | −2.87 | 0.71243 | 3.13 | 10.08 |
| GRK5 | rs4752266.2 | GA | 0.78 | 0.51 | 1.19 | −10.33 | 0.27667 | 3.67 | 12.31 |
| GRK5 | rs915394.2 | CNV | 1.39 | 0.96 | 2.01 | 11.91 | 0.08469 | 1.28 | 2.23 |
| GRK5 | rs915394.2 | GA | 1.09 | 0.7 | 1.67 | 2.88 | 0.74493 | 1.38 | 2.94 |
| GRK5 | rs1268947.2 | CNV | 1.15 | 0.75 | 1.75 | 3.15 | 0.52415 | 1.23 | 1.72 |
| GRK5 | rs1268947.2 | GA | 0.78 | 0.46 | 1.32 | −5 | 0.42146 | 1.24 | 1.82 |
| GRK5 | rs1537576.2 | CNV | 1.57 | 1.07 | 2.3 | 27.1 | 0.0211 | 0.88 | −4.02 |
| GRK5 | rs1537576.2 | GA | 1.84 | 1.15 | 2.94 | 35.48 | 0.0143 | 1.17 | 5.17 |
| | rs2039488.2 | CNV | 0.76 | 0.48 | 1.2 | −5.05 | 0.28877 | 0.2 | −12.5 |
| | rs2039488.2 | GA | 0.62 | 0.35 | 1.09 | −8.3 | 0.11599 | 0.27 | −11.29 |

TABLE 9-continued

OR and AR from analysis of ARM subtypes.

| | | | | | | | | |
|---|---|---|---|---|---|---|---|---|
| RGS10 | rs1467813.1 | CNV | 0.95 | 0.67 | 1.36 | −2.31 | 0.85551 | 0.98 | −0.68 |
| RGS10 | rs1467813.1 | GA | 0.85 | 0.56 | 1.29 | −7.69 | 0.52905 | 0.88 | −5.73 |
| | rs927427.1 | CNV | 1.08 | 0.72 | 1.63 | 5.82 | 0.75722 | 0.91 | −6.99 |
| | rs927427.1 | GA | 1.1 | 0.68 | 1.78 | 6.67 | 0.81152 | 0.98 | −1.63 |
| PLEKHA1 | rs4146894.1 | CNV | 2.53 | 1.64 | 3.91 | 52.45 | <0.0001 | 1.94 | 37.72 |
| PLEKHA1 | rs4146894.1 | GA | 2.09 | 1.24 | 3.51 | 44 | 0.0069 | 1.77 | 33.08 |
| PLEKHA1 | *rs12258692.2* | CNV | — | — | — | — | — | — | — |
| PLEKHA1 | *rs12258692.1* | GA | — | — | — | — | — | — | — |
| PLEKHA1 | *rs4405249.1* | CNV | 0.53 | 0.27 | 1.02 | −16.43 | 0.06989 | 0.51 | −16.36 |
| PLEKHA1 | *rs4405249.1* | GA | 0.63 | 0.3 | 1.33 | −12.27 | 0.17898 | 0.64 | −11.43 |
| PLEKHA1 | *rs1045216.2* | CNV | 0.5 | 0.32 | 0.78 | −48.35 | 0.0026 | 0.4 | −22.18 |
| PLEKHA1 | *rs1045216.2* | GA | 0.44 | 0.26 | 0.72 | −58.72 | 0.001 | 0.45 | −19.85 |
| | *rs1882907.2* | CNV | 0.52 | 0.35 | 0.77 | −19.38 | 0.0024 | 0.7 | −3.08 |
| | *rs1882907.2* | GA | 0.6 | 0.38 | 0.95 | −15.9 | 0.035 | 0.22 | −8.27 |
| LOC387715 | *rs10490923.2* | CNV | 0.48 | 0.28 | 0.85 | −14.84 | 0.0114 | 0.17 | −11.63 |
| LOC387715 | *rs10490923.2* | GA | 0.74 | 0.39 | 1.38 | −7.07 | 0.41496 | 0.58 | −5.49 |
| LOC387715 | *rs2736911.2* | CNV | 0.71 | 0.41 | 1.22 | −7.12 | 0.24548 | 1.22 | 0.96 |
| LOC387715 | *rs2736911.2* | GA | 0.62 | 0.32 | 1.19 | −9.43 | 0.13179 | 2.2 | 4.96 |
| LOC387715 | *rs10490924.2* | CNV | 5.64 | 3.52 | 9.06 | 60.52 | <0.0001 | 2.81 | 23.7 |
| LOC387715 | *rs10490924.2* | GA | 3.43 | 2.02 | 5.84 | 44.55 | <0.0001 | 2.63 | 21.83 |
| PRSS11 | *rs11538141.2* | CNV | — | — | — | — | — | — | — |
| PRSS11 | *rs11538141.2* | GA | — | — | — | — | — | — | — |
| PRSS11 | rs760336.2 | CNV | 0.63 | 0.43 | 0.92 | −37.33 | 0.0178 | 0.71 | −10.35 |
| PRSS11 | rs760336.2 | GA | 0.63 | 0.4 | 0.98 | −36.73 | 0.0322 | 0.84 | −5.52 |
| PRSS11 | rs763720.1 | CNV | 1.77 | 1.24 | 2.54 | 23.25 | 0.0031 | 1.69 | 20.43 |
| PRSS11 | rs763720.1 | GA | 1.74 | 1.14 | 2.65 | 22.5 | 0.0107 | 1.4 | 12.86 |
| PRSS11 | *rs1803403.1* | CNV | 3.33 | 1.39 | 8.02 | 12.17 | 0.0055 | 3.33 | 12.17 |
| PRSS11 | *rs1803403.1* | GA | 3.85 | 1.53 | 9.72 | 14.49 | 0.0039 | 3.85 | 14.49 |

| | | | Recessive (RR vs (RN + NN)) | | | | Homozygotes (RR vs NN) | |
|---|---|---|---|---|---|---|---|---|
| GENE | SNP.allele | Subtype | OR | 95% CI | | AR | p-value | OR | AR |
| | rs6658788.2 | CNV | 1.11 | 0.73 | 1.68 | 2.5 | 0.68123 | 0.95 | −2.26 |
| | rs6658788.2 | GA | 1.01 | 0.62 | 1.66 | 0.35 | 1 | 0.92 | −3.97 |
| | rs1538687.2 | CNV | 0.47 | 0.25 | 0.9 | −5.97 | 0.0202 | 0.42 | −11.38 |
| | rs1538687.2 | GA | 0.45 | 0.2 | 1.01 | −6.25 | 0.07239 | 0.38 | −12.32 |
| | rs1416962.2 | CNV | 0.95 | 0.56 | 1.62 | −0.62 | 0.89111 | 0.89 | −2.63 |
| | rs1416962.2 | GA | 0.62 | 0.31 | 1.24 | −5.07 | 0.22948 | 0.57 | −11.11 |
| | rs946755.2 | CNV | 1.03 | 0.6 | 1.78 | 0.37 | 1 | 0.94 | −1.39 |
| | rs946755.2 | GA | 0.69 | 0.34 | 1.38 | −3.8 | 0.37606 | 0.6 | −9.26 |
| | rs6428352.2 | CNV | — | — | — | — | — | — | — |
| | rs6428352.2 | GA | — | — | — | — | — | — | — |
| CFH | rs800292.1 | CNV | 0.21 | 0.07 | 0.64 | −4.59 | 0.0053 | 0.18 | −7.64 |
| CFH | rs800292.1 | GA | 0.09 | 0.01 | 0.75 | −5.33 | 0.0113 | 0.08 | −8.66 |
| CFH | *rs1061170.2* | CNV | 4.11 | 2.2 | 7.69 | 27.24 | <0.0001 | 9.35 | 61.82 |
| CFH | *rs1061170.2* | GA | 5.66 | 2.9 | 11.04 | 35.95 | <0.0001 | 12.26 | 68.61 |
| CFH | *rs10922093.1* | CNV | 0.4 | 0.18 | 0.91 | −5.96 | 0.0327 | 0.33 | −11.72 |
| CFH | *rs10922093.1* | GA | 0.26 | 0.08 | 0.85 | −7.43 | 0.032 | 0.21 | −14.08 |
| CFH | rs70620.1 | CNV | 0.63 | 0.24 | 1.69 | −1.46 | 0.42256 | 0.6 | −2.2 |
| CFH | rs70620.1 | GA | 0.28 | 0.06 | 1.36 | −2.9 | 0.17068 | 0.26 | −4.1 |
| | rs1853883.2 | CNV | 1.88 | 1.28 | 2.78 | 18.84 | 0.0014 | 3.2 | 51.28 |
| | rs1853883.2 | GA | 2.57 | 1.65 | 4 | 29.15 | 0.0003 | 5.12 | 66.42 |
| | rs1360558.1 | CNV | 1.24 | 0.78 | 1.98 | 3.75 | 0.41376 | 1.27 | 7.61 |
| | rs1360558.1 | GA | 1.17 | 0.68 | 2.02 | 2.67 | 0.67873 | 1.25 | 7.14 |
| | rs955927.2 | CNV | 1.34 | 0.83 | 2.17 | 4.9 | 0.20048 | 1.38 | 9.84 |
| | rs955927.2 | GA | 1.2 | 0.68 | 2.1 | 2.86 | 0.57564 | 1.22 | 6.06 |
| | rs4350226.2 | CNV | — | — | — | — | — | — | — |
| | rs4350226.2 | GA | — | — | — | — | — | — | — |
| GRK5 | rs4752266.2 | CNV | 2.82 | 0.96 | 8.24 | 3.9 | 0.06229 | 2.63 | 5.74 |
| GRK5 | rs4752266.2 | GA | 2.88 | 0.9 | 9.23 | 4.04 | 0.06909 | 2.51 | 5.33 |
| GRK5 | rs915394.2 | CNV | 1.56 | 0.57 | 4.3 | 1.54 | 0.48645 | 1.74 | 2.96 |
| GRK5 | rs915394.2 | GA | 1.42 | 0.44 | 4.58 | 1.17 | 0.57824 | 1.45 | 1.81 |
| GRK5 | rs1268947.2 | CNV | 1.35 | 0.36 | 5.05 | 0.58 | 0.76382 | 1.39 | 0.8 |
| GRK5 | rs1268947.2 | GA | 1 | 0.2 | 5.02 | 0 | 1 | 0.95 | −0.1 |
| GRK5 | rs1537576.2 | CNV | 1.06 | 0.69 | 1.63 | 1.3 | 0.83192 | 1.44 | 14.26 |
| GRK5 | rs1537576.2 | GA | 1.44 | 0.89 | 2.34 | 8.51 | 0.17778 | 2.04 | 28.32 |
| | rs2039488.2 | CNV | 0.18 | 0.03 | 0.91 | −2.36 | 0.0318 | 0.17 | −2.88 |
| | rs2039488.2 | GA | 0.2 | 0.02 | 1.7 | −2.3 | 0.21758 | 0.19 | −2.83 |
| RGS10 | rs1467813.1 | CNV | 0.83 | 0.45 | 1.54 | −1.61 | 0.63004 | 0.83 | −2.79 |
| RGS10 | rs1467813.1 | GA | 0.81 | 0.39 | 1.69 | −1.85 | 0.70453 | 0.76 | −3.85 |
| | rs927427.1 | CNV | 1.76 | 1.13 | 2.74 | 11.97 | 0.0107 | 1.65 | 21.15 |
| | rs927427.1 | GA | 1.5 | 0.9 | 2.5 | 8.16 | 0.15618 | 1.47 | 16.43 |
| PLEKHA1 | rs4146894.1 | CNV | 2.46 | 1.63 | 3.71 | 23.64 | <0.0001 | 3.95 | 56 |
| PLEKHA1 | rs4146894.1 | GA | 1.92 | 1.2 | 3.08 | 16.31 | 0.0084 | 2.87 | 44.63 |
| PLEKHA1 | *rs12258692.2* | CNV | — | — | — | — | — | — | — |
| PLEKHA1 | *rs12258692.1* | GA | — | — | — | — | — | — | — |

TABLE 9-continued

OR and AR from analysis of ARM subtypes.

| | | | | | | | | | |
|---|---|---|---|---|---|---|---|---|---|
| PLEKHA1 | *rs4405249.1* | CNV | 0.97 | 0.11 | 8.85 | −0.05 | 1 | 0.83 | −0.41 |
| PLEKHA1 | *rs4405249.1* | GA | 0.57 | 0.04 | 9.31 | −0.76 | 1 | 0.51 | −1.2 |
| PLEKHA1 | *rs1045216.2* | CNV | 0.31 | 0.17 | 0.58 | −15.72 | 0.0002 | 0.25 | −38.01 |
| PLEKHA1 | *rs1045216.2* | GA | 0.32 | 0.15 | 0.7 | −15.46 | 0.0017 | 0.24 | −38.67 |
| | rs1882907.2 | CNV | 0.44 | 0.14 | 1.38 | −1.91 | 0.20808 | 0.38 | −3.11 |
| | rs1882907.2 | GA | 0.16 | 0.02 | 1.37 | −2.89 | 0.12039 | 0.14 | −4.32 |
| LOC387715 | *rs10490923.2* | CNV | 0.1 | 0.01 | 0.98 | −2.89 | 0.0413 | 0.09 | −3.78 |
| LOC387715 | *rs10490923.2* | GA | 0.48 | 0.08 | 2.91 | −1.66 | 0.65244 | 0.45 | −2.24 |
| LOC387715 | *rs2736911.2* | CNV | 0.92 | 0.09 | 8.92 | −0.08 | 1 | 0.86 | −0.18 |
| LOC387715 | *rs2736911.2* | GA | 1.43 | 0.13 | 15.97 | 0.42 | 1 | 1.3 | 0.38 |
| LOC387715 | *rs10490924.2* | CNV | 6.18 | 2.62 | 14.59 | 22.67 | <0.0001 | 12.11 | 46.39 |
| LOC387715 | *rs10490924.2* | GA | 4.74 | 1.9 | 11.84 | 17.47 | 0.0003 | 7.05 | 32.05 |
| PRSS11 | *rs11538141.2* | CNV | — | — | — | — | — | — | — |
| PRSS11 | *rs11538141.2* | GA | — | — | — | — | — | — | — |
| PRSS11 | rs760336.2 | CNV | 0.61 | 0.39 | 0.95 | −10.03 | 0.0348 | 0.49 | −30.78 |
| PRSS11 | rs760336.2 | GA | 0.71 | 0.42 | 1.19 | −7.3 | 0.23778 | 0.56 | −25.69 |
| PRSS11 | rs763720.1 | CNV | 2.1 | 0.85 | 5.18 | 3.55 | 0.12829 | 2.64 | 7.87 |
| PRSS11 | rs763720.1 | GA | 4.71 | 1.88 | 11.79 | 11.06 | 0.0001 | 5.41 | 18.69 |
| PRSS11 | *rs1803403.1* | CNV | — | — | — | — | — | — | — |
| PRSS11 | *rs1803403.1* | GA | — | — | — | — | — | — | — |

OR and AR are bolded and underlined if corresponding p-values (chi-squared test, p-values simulated using 10000 replicates) are less than 0.001 and bolded if less than 0.05.
SNP.allele denotes the SNP measured and the risk allele (minor allele in controls).
RR denotes homozygotes for the risk allele,
RN denotes heterozygotes for the risk allele and
NN denotes homozygotes for the normal allele.
SNPs in italics are the locally typed SNPs.

Discussion

Our linkage studies of ARM families have consistently identified the Chromosome 1q31 and Chromosome 10q26 loci, in addition to several other loci. Multiple linkage studies have replicated this finding and thus a focused SNP analysis of both regions using ARM families as well as with unrelated affected individuals and controls was undertaken. On Chromosome 1q31, we have confirmed the strong association with CFH that has been reported by others (see also Conley et al. (2005)) and, for the first time, have shown that SNPs in CFH significantly account for the linkage signal. Interestingly, our smallest GIST p-value (<0.001) is with rs1853883, which has a high D' of 0.91 with the Y402H variant, and not with the presumed "disease-associated" Y402H variant itself. This raises the possibility that other possible ARM-related variants within the CFH gene may still have to be considered and that these may be in high LD with Y402H.

Our studies of Chromosome 10q26 have implicated two potential loci, a very strongly-implicated locus, inclusive of three tightly linked genes, PLEKHA1, LOC387715, and PRSS11, and a less strongly-implicated locus comprising two genes, GRK5 and RGS10 (FIGS. 1-1 and 1-2). The GIST analysis does not support PRSS11 as the ARM-related gene, but it does not completely exclude it as a potential candidate. PLEHKA1 has the lowest GIST-derived p-values while LOC387715 harbors the SNP with the strongest association signal and the highest odds ratios. With the high linkage disequilibrium between the SNPs in LOC387715 and PLEKHA1, one cannot clearly distinguish between these genes from statistical analyses alone. However, it is clear that the magnitude of the impact of the PLEKHA1/LOC387715 locus on ARM is comparable to that which has been observed for the CFH locus. Like the recent studies in Science (Edwards et al. 2005; Haines et al. 2005; Klein et al. 2005), we have found in our case-control population that the CFH allele (either heterozygous or homozygous) accounts for an odds ratio of 5.3 OR (CI: 3.4-8.4) and a significant population attributable risk of 68%. In the same fashion, the high-risk allele within the PLEKHA1/LOC387715 locus accounts for an odds ratio of 5.0 (CI: 3.2-7.9) and 57% population attributable risk when considering both heterozygous and homozygous individuals. As noted by Klein et al (2005), the odds ratios that are determined from a case control study will usually overestimate the equivalent relative risk that is required for determining the lifetime risk.

In the case of Complement factor H (CFH) on Chromosome 1, the association data were extremely compelling for a single gene, even though CFH is within a region of related genes. In addition to the association data found by multiple independent groups, there is additional biological data to implicate CFH, including localization of the protein within drusen deposits of ARM patients. Thus, we also must consider the biological relevance of the potential ARM-susceptibility genes identified by our studies of Chromosome 10q26.

As noted above, the GIST analysis most strongly implicates PLEKHA1, particularly when we included the additional non-synonymous SNPs that we added to the genotyping. PLEKHA1 (GenBank NM_001001974, NM_021622, NP_001001974 and NP_067635; MIM 607772; UniGene Hs.287830) encodes the protein, TAPP1, which is a 404 amino acid protein with a putative phosphatidylinositol 3,4,5-trisphosphate-binding motif (PPBM) as well as two pleckstrin homology (PH) domains. The last 3 C-terminal amino acids have been predicted to interact with one or more of the 13 PDZ domains of MUPP1 (similar to the PDZ domain within PRSS11). Dowler and colleagues (Dowler et al. 2000 Identification of pleckstrin-homology-domain-containing proteins with novel phosphoinositide-binding specificities. Biochem J 351:19-31.) have shown that the entire TAPP1 protein as well as the C-terminal PH domain interact specifically with phosphatidylinositol 3,4-bisphosphate (PtdIns(3,4)P2), but not with any other phosphoinositides. TAPP1, which has 58% identity with the first 300 amino acids of TAPP2, shows a 5-fold higher affinity for PtdIns(3,4)P2 than TAPP2 and this binding is nearly eliminated by mutation of the conserved arg212 to leucine within the PPBM region (which is part of the second PH domain). The most well-defined role for TAPP1 (and its relatives, Bam32 and TAPP2) has been as an activator of lymphocytes. PtdIns(3,4)P2 is preferentially recruited to cell membranes when lipid phosphatase (SHIP) is activated along with PI3Ks (phosphatidyl inositol 3-kinase). SHIP is responsible for the dephosphorylation of PIP3 to PtdIns(3,4)P2. SHIP is a negative regulator of lymphocyte activation and thus TAPP1 (and TAPP2) may be crucial negative regulators of mitogenic signaling and of the PI3K signaling pathway. Thus, one can envision a role of PLEKHA1 and its protein TAPP1 in the eye by modifying local lymphocyte activation, consistent with the hypothesis that ARM is closely linked to an inflammatory process.

However, we need to still consider the biological plausibility of the other two candidate genes, LOC387715 and PRSS11, within this locus. Little is known regarding the biology of LOC387715 (Genbank XM 373477 and XP 373477; UniGene Hs.120359), except that its expression appears to be limited to the placenta. Our own reverse transcription experiments with human retinal RNA have confirmed the expression of PLEKHA1 and PRSS11, but we have not detected LOC387715 transcripts in the retina under standard conditions, even though we confirmed its expression with placental RNA (data not shown). However, we cannot exclude the possibility that LOC387715 is expressed in very low levels in the retina or retinal pigment epithelium or that its expression in non-ocular tissues, such as dendritic cells or migrating macrophages, could be a factor in the pathogenesis of ARM.

PRSS11 (GenBank NM 002775 and NP 002766; MIM 602194 and UniGene Hs.501280) is one of the genes of the mammalian HtrA (high temperature requirement A) serine protease family, which has a highly conserved C-terminal PDZ domain (Oka et al. 2004 HtrA1 serine protease inhibits signaling mediated by TGFbeta family proteins. Development 131:1041-1053). These secretory proteases were initially identified because of their homologies to bacterial forms that are required for survival at high temperatures and molecular chaperone activity at low temperatures. The ATP-independent serine protease activity is thought to degrade misfolded proteins at high temperature. The mammalian form, HtrA1, has been shown to be selectively stimulated by type III collagen alpha 1 C propeptide, in contrast to HtrA2. (Murwantoko et al. 2004 Binding of proteins to the PDZ domain regulates proteolytic activity of HtrA1 serine protease. Biochem J 381:895-904) Type III collagen is a major constituent (35-39% of the total collagen) in Bruch membrane and is also present in small amount in the retinal microvascular basement membranes. Developmental studies have reported ubiquitous expression of HtrA1 but with temporal and spatial specificities that coincide with those regions in which TGF-beta proteins play a regulatory role. (De Luca et al. 2004 Pattern of expression of HtrA1 during mouse development. J Histochem Cytochem 52:1609-1617.) Oka and colleagues (Oka et al. 2004 HtrA1 serine protease inhibits signaling mediated by Tgfbeta family proteins. Development 131:1041-1053.) have shown that HtrA1 is capable of inhibiting signaling of a number of TGF-beta family proteins, including Bmp4, Bmp2 and TGF-beta1, presumably by preventing receptor activation with a requirement for protease activity of the HtrA1 molecule. One clue as to the potential importance of these relationships for ARM comes from the studies of Hollborn et al (2004) Contrary effects of cytokines on mRNAs of cell cycle- and ECM-related proteins in hRPE cells in vitro. Curr Eye Res 28:215-223 who found that human RPE cells in vitro experienced reduced proliferation in the presence of TGF-beta1 and TGF-beta2 and an increase in levels of collagen III and collagen IV transcripts. Normally, a rise in collagen III would activate HtrA1 and lead to secondary inhibition of the effects of TGF-beta1. However, if the serine protease is less effective (either due to reduced synthesis or a nonfunctional mutation), then this regulatory pathway would be disrupted, leading to an overall reduction of proliferation potential of the RPE cells, perhaps contributing to RPE atrophy or further changes that could lead to the development of ARM. The gradual reduction in solubility of type III collagen in Bruch's membrane that has been observed with aging could also, in part, account for a general reduction in HtrA1 activity as an individual ages.

Both PRSS11 and PLEKHA1 are expressed in the retina, and a SAGE analysis of central and peripheral retina (GEO Expression data), indicates higher levels of transcripts of both genes in the central macula (more so for PLEKHA1 than PRSS11). Multiple studies (reported in GEO profiles) have shown that PLEKHA1 expression is significantly induced in a variety of cell types in response to exposure to specific inflammatory cytokines. PRSS11 has also been investigated as part of a microarray expression analysis of dermal fibroblasts that have been oxidatively challenged in a comparison between normal and ARM patients. In that study, half of the ARM samples (9/18) had lower Htra1 expression levels than any of the normal samples. The lower levels of Htra1 in non-ocular tissues of ARM patients would suggest that this is an intrinsic difference in the biology of these patients as compared to normal individuals, and not a consequence of degenerative changes in the eye.

The GRK5/RGS10 locus is supported by several lines of evidence. The peak of our $S_{all}$ multipoint curve is directly over GRK5 and our largest single-point $S_{all}$=3.86 (rs555938) is only 206 kb centromeric to GRK5. The p-values for the GIST analysis of the GRK5/RGS10 CIDR data were 0.004 and 0.006, which are even smaller than the p-value for the SNP within PLEKHA1 (0.008). Using our locally-genotyped sample, the GIST p-value for the GRK5 locus was 0.012, which is comparable to the p-value that we found for the Y402H variant in CFH (p=0.011). However, the CCREL analyses were not very significant for the GRK5 SNPs and the odds ratios were mostly non-significant.

Based on biological evidence, GRK5 (GenBank NM 005308 and NP 005299; UniGene Hs.524625; MIM 600870; and PharmGKB PA180) is reasonable ARM candidate gene, given its role in modulating neutrophil responsiveness to chemoattractants and its interactions with the Toll 4 receptor (Haribabu and Snyderman 1993 Identification of additional members of human G-protein-coupled receptor kinase multigene family. Proc Natl Acad Sci USA 90:9398-9402; Fan and Malik 2003 Toll-like receptor-4 (TLR4) signaling augments chemokine-induced neutrophil migration by modulating cell surface expression of chemokine receptors. Nat Med 9:315-321.), which has also been implicated in ARM (Zareparsi et al. 2005b Toll-like receptor 4 variant D299G is associated with susceptibility to age-related macular degeneration. Hum Mol Genet 12:1449-55). The retinal or RPE expression of GRK5 is not especially relevant to the argument of causality because it would be the expression and function of GRK5 in migrating lymphocytes and macrophages that would be crucial to its role in the immune/inflammatory pathways that may be pathogenic in ARM. The strongest GIST results occur at rs2039488, which is actually located between GRK5 and RGS10, 3' to the ends of both genes. Several other SNPs within the GRK5 gene also have small GIST p-values, while the RGS10 SNP has a non-significant GIST p-value. However, we cannot completely exclude the possibility that there is a SNP within RGS10 that is in strong linkage disequilibrium with rs2039488.

RGS10 (GenBank NM 001005339, NM 002925, NP 001005339 and NP 002916; UniGene Hs.501200; and MIM 602856) is one of a family of G protein coupled receptors that has been implicated in chemokine-induced lymphocyte migration (Moratz et al. 2004 Regulation of chemokine-induced lymphocyte migration by RGS proteins. Methods Enzymol 389:15-32.) and whose expression in dendritic cells (which have been identified in ARM-related drusen deposits) is modified by the Toll-like signaling pathway (Shi et al. 2004 Toll-like receptor signaling alters the expression of regulator of G protein signaling proteins in dendritic cells: implications for G protein-coupled receptor signaling. J Immunol 172: 5175-5184). RGS10 and GRK5 expression in the same microarray study of oxidatively-stressed dermal fibroblasts in AMD and control subjects showed minor fluctuations among the samples, but no clear differences between the control and affected cases. This does not necessarily lower the potential for these genes being involved in ARM, since the dermal fibroblasts are lacking the cell populations that would be expected to have modulation of RGS10- and/or GRK5-related proteins.

We have attempted to look at potential interactions between the high-risk alleles within the PLEKHA1/LOC387715 and GRK5/RGS10 loci with respect to CFH on Chromosome 1. This is perhaps the first report to use GIST to examine these interactions and we found no evidence that the NPL data on Chromosome 1 could be accounted for by the SNP data on Chromosome 10. Conversely, we found no such associations between the NPL data on Chromosome 10 and the SNP data from the CFH alleles. Logistic regression analysis also failed to identify an interaction, and it appears that a simple additive risk model is the most parsimonious. We have performed some initial logistic analyses that include exposure to smoking. These analyses were initiated because of the previous suggestion of an interaction of smoking with the biology of complement factor H (Esparza-Gordillo et al. 2004 Genetic and environmental factors influencing the human factor H plasma levels. Immunogenetics 56:77-82.) and our prior studies which found an interaction of smoking and the locus on Chromosome 10q26 (Weeks et al. 2004). To date, we have found no strong interaction of smoking with either the CFH or PLEKHA1/LOC387715 loci, but we are still exploring a possible interaction with the GRK5/RGS10 locus and different modeling strategies. We also examined the associations of ARM subphenotype with the SNPs on both Chromosomes 1 and 10 (Table 9). We found no major differences in the odds ratios for the presence of either geographic atrophy or choroidal neovascular membranes, suggesting that these ARM loci contribute to a common pathogenic pathway that can give rise to either end stage form of the disease. This does not exclude the possibility that there are other, as yet undescribed, genetic loci that may confer specific risk to geographic atrophy or CNV development separately.

In summary, these SNP-based linkage and association studies illustrate both the power and limitation of such methods to identify causative alleles and genes underlying ARM susceptibility. These genetic approaches allow us to consider genes and their variants that may contribute to a disease, whether or not there is tissue-specific expression. Through high density SNP genotyping, we have narrowed the list of candidate genes within the linkage peak found on Chromosome 10q26, from hundreds to primarily GRK5 and PLEKHA1, but we cannot completely exclude the possible roles of RGS10 and/or PRSS11 and LOC387715. Additional genotyping of non-synonymous 3' SNPs within the GRK5 gene may help to further discriminate between GRK5 and RGS10, but it may not establish a definitive assignment of causality. Replication by other studies (such as in the case of CFH) may allow one to focus on a single gene, but there is also the distinct possibility that we will be unable to achieve further resolution with association studies or clearly establish if there are more than two genes that are responsible for ARM susceptibility on Chromosome 10q26. However, molecular biologists can now investigate the potential role of each of these candidate genes in mouse models of ARM and address the issue of a causal role in disease pathogenesis.

Example 2

Follow-Up to Example 1

This Example provides additional data supporting and confirming the conclusions and discoveries provided in Example 1, in which allelic variations in PLEKHA1 and hypothetical LOC387715 genes were identified as risk factors for Age-related maculopathy.

The etiology of ARM is complex, with environmental as well as genetic susceptibility playing a role. Association-based analyses are generally more sensitive to small genetic effects than linkage-based analyses and are extremely valuable for fine mapping of disease-related genes Cordell et al (2005) Genetic association studies Lancet. 366, 1121-1131. Case-control association studies with the use of unrelated individuals may have advantages over family-based studies, especially when a multilocus genetic model is anticipated (Howson et al. (2005) Comparison of population- and family-based methods for genetic association analysis in the presense of interacting loci. Genet Epidemiol. 29, 51-67. Risch et al. (2001) Implications of multilocus inheritance for gene-disease association studies. Theor Popul Biol. 60, 215-220.), however such studies are potentially sensitive to the ascertainment scheme for the case and control cohorts. For this reason, there is value in assessing candidate genes in populations with different ascertainment schemes. This Example investigates the complement factor H (CFH) gene, the elongation of very long chain fatty acid-like 4 (ELOVL4) gene, the PLEKHA1 gene, and the hypothetical LOC387715 gene in two distinct cohorts.

The association of the CFH gene with ARM susceptibility has been established in samples of European American descent (Edwards et al. (2005), Haines et al. (2005), Klein et al. (2005), Hageman et al. (2005), Conley et al. (2005), Zareparsi et al. (2005) as well as in samples from the United Kingdom—Sepp, T. et al (2006) Complement factor H variant Y402H is a major risk detriment for geographic atrophy and choroidal neovascularization in smokers and nonsmokers. Invest Ophthalmol *Vis Sci.* 47, 536-540, Germany—Rivera et al (2005) Hypothetical LOC387715 is a second major susceptibility gene for age-related macular degeneration, contributing independently of complement factor H to disease risk. Hum Mol Genet. 14, 3227-3236, France—Souied et al (2005) Y402H complement factor H polymorphism associated with exudative age-related macular degeneration in the French population. Mol Vis. 11, 1135-1140, Iceland—Magnusson et al (2006) CFH Y402H confers similar risk of soft drusen and both forms of advanced AMD. PLoS Med. 3, e5. and Japan—Okamoto et al (2006) Complement factor H polymorphisms in Japanese population with age-related macular degeneration. Mo Vis. 12, 156-158.

Three studies support the PLEKHA1/LOC387715 locus on chromosome 10q26 (Rivera et al (2005), Jakobsdottir Jr. et al (2005) and Schmidt et al (2006) Cigarette smoking strongly modifies the association of LOC387715 and age-related macular degeneration Am J Hum Genet. 78, 852-864. The study by Jakobsdottir et al. (2005) Susceptibility genes for age-related maculopathy on chromosome 10q26. Am J Hum Genet. 77, 389-407 reported that the PLEKHA1/

LOC387715 locus was significantly associated with ARM status, however strong linkage disequilibrium between PLEKHA1 and LOC387715 in the independent family-based and case-control populations utilized for the study meant that a role for one gene over the other could not be determined (Jakobsdottir, et al. (2005)). Since publication of Jakobsdottir et al., evidence that the hypothetical LOC387715 gene was more likely to be the gene accounting for susceptibility to ARM has been published in a study by Rivera et al. (2005) that utilized two independent case-control samples (Rivera et al. (2005)) and a study by Schmidt et al. that utilized both family based and case-control studies Schmidt et al. All three studies indicated that the association of this region on chromosome 10q26 with ARM status was independent of the association with CFH that had been previously reported in all three populations (Haines et al. (2005, Conley et al. (2005), Rivera et al. (2005)). Additionally, based on the Schmidt et al. study, the effect of the LOC387715 locus appears to be modified by smoking history Schmidt et al. (2006).

Two studies have evaluated a potential role for ELOVL4 in ARM in humans. Ayyagari et al. (2001) Evaluation of the ELOVL4 gene in patients with age-related macular degeneration. Opthalmic Genet. 22, 233-239 evaluated the gene and found no significant association with ARM status in their sporadic case-control analysis. However, Conley et al. found a significant association of ELOVL4 and ARM status in our familial and sporadic case-control analyses Conley et al. (2005). The difference in findings between these studies may be related to the proportion of cases with exudative ARM in each population, since Conley et al. found that ELOVL4 was especially associated with the exudative subphenotype. These results indicate that additional studies are needed to establish or refute a relationship between ELOVL4 and ARM.

The two cohorts utilized for this study were the Cardiovascular Health Study (CHS), a population-based cohort of individuals 65 years and older at baseline for which ARM status was not a factor for ascertainment Fried et al. (1991) The Cardiovascular Health Study: design and rationale. Ann Epidemiol. 1, 263-276 and the Age-Related Eye Disease Study (AREDS), a cohort of individuals aged 55 to 80 years participating in a randomized controlled clinical trial of anti-oxidant and zinc intervention for which ARM status was a factor for ascertainment Age-Related Eye Disease Study Research Group (1999) the Age-Related Eye Disease Study (AREDS): design implications. AREDS report no. 1. Control Clin Trials. 20, 573-600. These cohorts have been previously described (Klein, R., et al. (2003) Early age-related maculopathy in the cardiovascular health study. Ophthalmology. 110, 25-33 and Age-Related Eye Disease Study Research Group (2000) Risk factors associated with age-related macular degeneration. A case-control study in the age-related eye disease study: Age-Related Eye Disease Study Report Number 3. Ophthalmology. 107, 2224-2232)

This study was designed to evaluate the CFH, ELOVL4, PLEKHA1, and LOC387715 genes in two independent cohorts with very different ascertainment schemes in relation to ARM status and then to incorporate the findings into meta-analyses. Association of a gene with susceptibility to ARM regardless of ascertainment scheme would further increase the evidence that the association is real and would enhance the likelihood that evaluation of the gene(s) would accurately identify at risk individuals.

Abbreviations: ARM=Age-related maculopathy; GA=Geographic atrophy; CNV=Choroidal neovascular membranes; OR=Odds ratio; PAR=Population attributable risk; $OR_{dom}$=Odds ratio for dominance effects; $OR_{rec}$=Odds ratio for recessive effects; $OR_{het}$=Odds ratio for subjects heterozygote for risk allele; and $OR_{hom}$=Odds ratio for subjects homozygote for risk allele.

Material and Methods

Cardiovascular Health Study (CHS) Participants—Sampling and Phenotyping

CHS is a population-based, longitudinal study primarily designed to identify factors related to cardiovascular disease in those aged 65 and older. Retinal assessments were performed at the 8 year follow up visit and surviving members of this cohort have just completed their 18 year follow up evaluation. Community-based recruitment took place in Forsyth County, N.C.; Sacramento County, Calif.; Washington County, Md.; and Pittsburgh, Pa. Medicare eligibility lists of the Health Care Financing Administration were utilized to identify individuals who were aged 65 and older. Individuals aged 65 years and older living in the households of list members were also eligible. Inclusion criteria were minimal and included being non-institutionalized, expected to remain in the area for at least three years, able to give informed consent, not wheelchair-bound, not receiving hospice care, and not receiving radiation or chemotherapy for cancer. Fried et al. (1991). DNA samples from the CHS were used for this research.

CHS subjects usually had the retina of one randomly selected eye photographed and the photographs were graded by Dr. Gorin using the same classification model that was described in prior publications Weeks et al. (2004) Age-related maculopathy: a genomewide scan with continued evidence of susceptibility loci within the 1q31, 10q26, and $17_s25$ regions. Am J Jum Genet. 75, 174-189. Only Caucasian individuals are included in the analysis, as the sample size of other groups with ARM is too small for reasonable results: there were 182 black controls but only 3 cases, and 5 controls of other races. All CHS cases (n=126) used for analyses are "Type A", which falls into our most stringent model for clinical classification Weeks et al. (2004). Individuals in this category are clearly affected with ARM based on extensive and/or coalescent drusen, pigmentary changes (including pigment epithelial detachments), and/or the presence of end-stage disease [geographic atrophy (GA) and/or choroidal neovascular (CNV) membranes]. Very few CHS cases had end stage ARM, GA or CNV (Table 10); therefore analyses of specific subtypes of ARM were not conducted. All CHS controls (n=1,051) were of AREDS grade 1. A few potential controls (n=22) had unclear signs of GA or CNV and were excluded from analyses.

TABLE 10

Characteristics of the study populations.

| | | Clinical subtypes | | | | |
|---|---|---|---|---|---|---|
| | Mean (SD) age | Neither | GA only | CNV only | Both | Total | No. (%) males |
| AREDS data | | | | | | | |
| Controls (1) | 76.53 (4.44) | 175 | — | — | — | 175 | 86 (49) |
| Cases (3-4-5) | 79.46 (5.23) | 123 | 147 | 278 | 153 | 701 | 293 (42) |
| Cases (4-5) | 79.54 (5.23) | 27 | 147 | 278 | 153 | 605 | 253 (42) |

TABLE 10-continued

Characteristics of the study populations.

| | Mean (SD) age | Clinical subtypes | | | | Total | No. (%) males |
| | | Neither | GA only | CNV only | Both | | |
|---|---|---|---|---|---|---|---|
| Cases (3) | 78.93 (5.22) | 96 | 0 | 0 | 0 | 96 | 40 (42) |
| Cases (4) | 78.83 (5.23) | 24 | 59 | 149 | 34 | 266 | 124 (47) |
| Cases (5) | 80.10 (5.17) | 3 | 88 | 129 | 119 | 339 | 129 (38) |
| CHS data | | | | | | | |
| Controls | 70.27 (3.92) | 1051 | — | — | — | 1051 | 455 (43) |
| Cases | 73.22 (4.84) | 100 | 15 | 9 | 2 | 126 | 55 (44) |

In the AREDS cohort mean age and phenotypic classification is based on age at last fundus photography.
The number in the parentheses denotes the disease severity according the AREDS grading method.
In the CHS cohort mean age is based on age at baseline visit, but retinal evaluation was done at 8-year follow-up visit.

Age-Related Eye Disease Study (AREDS) Participants—Sampling and Phenotyping

AREDS is a prospective, multicenter study of the natural history of ARM and age-related cataract with a clinical trial of high dose vitamin and mineral supplementation embedded within the study. Individuals recruited into the AREDS study were men and women aged 55 to 80 years at enrollment; these individuals were required to be free of any condition or illness that would hinder long-term follow-up. Inclusion criteria were minimal and included having ocular media clear enough to allow for fundus photography and either no evidence of ARM in either eye or having ARM in one eye while the other maintained good vision (20/30 or better) (The Age-Related Eye Disease Study Research Group 1999). DNA samples from the NEI-AREDS Genetic Repository were used for this research.

ARM status was assigned using the AREDS age-related maculopathy grading system and based on phenotypes assigned at the most recent follow-up visit. Again, only Caucasian individuals are included in the analysis, as the sample size of other groups is too small for reasonable results: there are only 15 African American, 2 Hispanic and 3 individuals of other races. AREDS cases (n=701) consisted of grade 3, 4 and 5. AREDS subjects of grade 3 (n=96) have ARM but do not suffer from end-stage ARM, subjects of grade 4 (n=266) have end-stage ARM in one eye and subjects of grade 5 (n=339) have end-stage ARM in both eyes. AREDS controls (n=175) have AREDS grade 1 (grade 2 individuals were excluded prior to analyses).

Genotyping

The M299V variant in ELOVL4 (rs3812153), the Y402H variant in CFH (rs 1061170) and the S69A variant in LOC387715 (rs10490924) were genotyped using RFLP techniques. The primers, annealing temperatures and restriction endonuclease for each assay were: 5'-AGATGCCGATGT-TGTTAAAAG-3' (F, SEQ ID NO: 13), 5'-CATCTGGG-TATGGTATTAAC-3' (R, SEQ ID NO: 14), 50° C. and BspHI for ELOVL4; 5'-TCTTTTTGTGCAAACCTTTGTTAG-3' (F, SEQ ID NO: 15), 5'-CCATTGGTAAAACAAGGT-GACA-3' (R, SEQ ID NO: 16), 52° C. and NlaIII for CFH; 5'-GCACCTTTGTCACCACATTA-3' (F, SEQ ID NO: 17), 5'-GCCTGATCATCTGCATTTCT-3' (R, SEQ ID NO: 18), 54° C. and PvuII for LOC387715.

The A320T variant in PLEKHA1 (rs1045216) was genotyped using 5' exonuclease Assay-on-Demand TaqMan assays (Applied Biosystems Incorporated). Amplification and genotype assignments were conducted using the ABI7000 and SDS 2.0 software (Applied Biosystems Incorporated). For all genotyping conducted for this research, double-masked genotyping assignments were made for each variant, compared and each discrepancy addressed using raw data or by re-genotyping.

Association Analyses

SNP-disease association was measured with allele- and genotype chi-squared tests, and P-values were simulated using 100,000 replicates; in cases with one or more expected cell numbers less then five, the Fisher's exact test was used. The strength of the association was estimated by crude odds ratios (OR) and population attributable risks (PAR). A general formula was used to calculate the PAR: $PAR=P_r(OR-1)/(1+P_r(OR-1))$, where $P_1$ is the prevalence of the risk factor in the general population. Estimates of $P_r$ were derived from the CHS controls; this is reasonable, because the CHS subjects were not selected on the basis of ARM disease status, and the number of CHS controls is large (n=1,051). For comparison purposes, odds ratios adjusted ($OR_{adj}$) for age and gender were estimated. Logistic regression models were used to calculate both crude and adjusted odds ratios, using R (38). The less frequent allele in the control group was considered the risk allele, and the OR and $OR_{adj}$ were calculated by comparing those homozygote for the risk allele (RR) to the baseline group (those homozygote for the normal allele [NN]) and comparing those heterozygote for the risk allele (RN) to the baseline group. The contrasts for dominance (RR and RN versus NN) and recessive (RR versus RN and NN) effects were also evaluated.

Distinguishing Between PLEKHA1 and LOC387715

We employed the haplotype method (Valdes, A. M. and Thomson, G. (1997) Detecting disease-predisposing variants: the haplotype method. Am J Hum Genet. 60, 703-716) to identify which one of the two loci, A320T in PLEKHA1 or S69A in LOC387715, is more likely the actual disease predisposing variant in the 10q26 region. The basis of the haplotype method is simple and elegant (for a mathematical proof, see Valdes and Thomson (1997)). If all predisposing variants are included on a haplotype, then the neutral variants are expected to be in the same ratio in cases and controls on a particular disease-predisposing haplotype, although the actual frequencies may differ. On the other hand, if not all predisposing variants have been identified, equality in the ratios of haplotype frequencies of non-predisposing variants is not expected.

The expected ratios for the A320T-S69A haplotypes are formulated below, assuming one variant is ARM-predisposing and the other is a neutral variant. We assume that A320T and S69A are all the ARM-predisposing variants in the PLEKHA1-LOC387715 haplotype block on chromosome 10q26.

Four possible A320T-S69A haplotypes exist: G-G, A-G, G-T, and A-T. If A320T is the causal locus and S69A the neutral locus, we expect:

$$\left[\frac{f(G-G)}{f(G-T)}\right]_{controls} = \left[\frac{f(G-G)}{f(G-T)}\right]_{cases} \quad (1a)$$

$$\left[\frac{f(A-G)}{f(A-T)}\right]_{controls} = \left[\frac{f(A-G)}{f(A-T)}\right]_{cases} \quad (1b)$$

but, if S69A is the causal locus and A320T the neutral locus, we expect:

$$\left[\frac{f(G-G)}{f(A-G)}\right]_{controls} = \left[\frac{f(G-G)}{f(A-G)}\right]_{cases} \quad (2a)$$

$$\left[\frac{f(G-T)}{f(A-T)}\right]_{controls} = \left[\frac{f(G-T)}{f(A-T)}\right]_{cases} \quad (2b)$$

where f denotes frequencies of a particular haplotype in controls or cases.

The hypotheses of interest are:
$H_{O_P}$: The A329T variant in PLEKHA1 fully accounts for the ARM predisposition to the PLEKHA1-LOC387715 haplotype block.
$H_{O_L}$: The S69A variant in LOC387715 fully accounts for the ARM predisposition to the PLEKHA1-LOC387715 haplotype block.

Rejecting either of these hypotheses means that the tested variant is not sufficient to account for the ARM predisposition to the PLEKHA1-LOC387715 haplotype block, alone. Four 2×2 contingency tables can be derived from Formulas 1a, 1b, 2a, and 2b:

TABLE 1a

|  | Unexposed | Exposed |
|---|---|---|
| Controls | f(G-G) | f(G-T) |
| Cases | f(G-G) | f(G-T) |

TABLE 1b

|  | Unexposed | Exposed |
|---|---|---|
| Controls | f(A-G) | f(A-T) |
| Cases | f(A-G) | f(A-T) |

TABLE 2a

|  | Unexposed | Exposed |
|---|---|---|
| Controls | f(G-G) | f(A-G) |
| Cases | f(G-G) | f(A-G) |

TABLE 2b

|  | Unexposed | Exposed |
|---|---|---|
| Controls | f(G-T) | f(A-T) |
| Cases | f(G-T) | f(A-T) |

Under $H_{O_P}$ we expect homogeneity in contingency tables 1a and 1b, and under $H_{O_L}$ we expect homogeneity in contingency tables 2c and 2d. Regular chi-squared statistic may be calculated from each contingency table to generate a combined statistic. For $H_{O_L}$ the statistic is the maximum chi-squared from Formulas 1a and 1b, and for $H_{O_L}$ the statistic is the maximum chi-squared from Formulas 2a and 2b. However, due to dependency of the statistics derived from each set of contingency tables, the distribution of the combined statistics is not clear. The lack of independence arises from (1) combining measurements corresponding to various alleles at predisposing loci, and (2) linkage disequilibrium between predisposing and non-predisposing loci. Both of these conditions are inevitable, (1) because variant always has more than one allele, and (2) because, if the variants are in complete linkage equilibrium, there is no need to distinguish between their independent association signals.

As a result of the dependency in the data a permutation testing needs to be done conditionally on the allele at the predisposing locus (under the null hypotheses). We start by grouping the haplotypes (two for each person) according to the allele at the predisposing locus. Then the case-control labels are permuted within each group and a combined statistic is calculated for each pair of replicate. This permutation procedure is similar to the procedure proposed by Li H. (2001) (A permutation procedure for the haplotype method for identification of disease-predisposing variants. Ann Hum Genet. 65:189-196). Phased genotype data were not available and haplotypes had to be imputed from the unphased genotypes. Haplotype frequencies were estimated separately in controls and cases. The program SNPHAP (39) was used to estimate the haplotype frequencies and phased haplotypes at each subject. SNPHAP uses the EM algorithm to calculate a maximum likelihood estimate of haplotype frequencies given the unphased genotype data. The posterior probabilities of individual haplotype assignments exceed 94% for every individual typed at both A320T and S69A. The estimated haplotype frequencies are given in Table 11.

TABLE 11

Haplotype frequencies of A320T in PLEKHA1 and S69A in LOC387715 (estimated with the program SNPHAP).

| A320T-S69A | AREDS | | CHS | |
|---|---|---|---|---|
| haplotype | Controls | Cases | Controls | Cases |
| G-G | 0.3928 | 0.2802 | 0.3909 | 0.3188 |
| G-T | 0.1790 | 0.4149 | 0.1924 | 0.3294 |
| A-G | 0.4186 | 0.2792 | 0.3894 | 0.3337 |
| A-T | 0.0096 | 0.0257 | 0.0272 | 0.0180 |

Estimates derived from both the AREDS and CHS cohorts is given.

Interaction Analyses

The analyses of interaction were threefold: first, we tested for interacting genetic effects of Y402H in CFH and S69A in LOC387715 in both CHS and AREDS samples, then we tested for interaction of both Y402H and S69A with smoking history in both CHS and AREDS samples, and finally we calculated joint ORs of the three risk factors.

We followed a modeling strategy proposed by North et al. (North, B. V., Curtis, D. and Sham, P. C. (2005) Application of logistic regression to case-control association studies involving two causative loci. Hum Hered. 59, 79-87). Series of logistic regression models are fitted to the AREDS and CHS data sets in order to find the model that best describes the joint effects of CFH and LOC387715. For each genotype, models allowing for additive effects (ADD1, ADD2 and ADD-BOTH), and models which incorporate dominance effects (DOM1, DOM2 and DOM-BOTH) are fitted. The ADD1 model includes only the term $x_1$ for additive effects of CFH, coded as −1 for genotype TT at Y402H, as 0 for genotype CT, and as 1 for genotype CC. The ADD2 includes only model term $x_2$ for additive effects of LOC387715, coded as −1 for genotype GG at S69A, as 0 for genotype GT, and as 1 for genotype TT. The ADD-BOTH models the joint additive effects of CFH and LOC387715. The DOM1 incorporates dominance effects to ADD1, and includes $x_1$ and $z_1$, coded as 0.5 for genotype CT and −0.5 for genotypes TT and CC at Y402H. The DOM2 model similarly incorporates dominance effects to ADD2, and includes $x_2$ and $z_2$, coded as 0.5 for genotype GT and −0.5 for genotypes GG and TT at S69A. DOM-BOTH models the joint dominance effects of CFH and LOC387715. Three further models, that model the interaction between CFH and LOC387715, are fitted: ADD-INT includes the product term $x_1*x_2$, ADD-DOM includes $x_1*x_2$, $x_1*z_2$, and $z_1*x_2$, and DOM-INT includes $x_1*x_2$, $x_1*z_2$, $z_1*x_2$, and $z_1*z_2$.

The above modeling strategy was modified to investigate the joint effects of CFH and smoking, and the joint effects of LOC387715 and smoking. The modified approach is the same as used by Schmidt et al. (2006) to test for interaction between LOC387715 and smoking. The coding scheme is the same, as above, except that smoking is coded as 0 for never smokers and 1 for ever smokers. The models fitted for the effects of CFH and smoking are: ADD 1, SMOKE, ADD1-SMOKE, DOM1, ADD1-SMOKE-INT, and DOM1-SMOKE-INT, and the models fitted for the effects of LOC387715 and smoking are: ADD2, SMOKE, ADD2-SMOKE, DOM2, ADD2-SMOKE-INT, and DOM2-SMOKE-INT.

All models were compared by the Akaike's information criterion (AIC). Models for which the AIC differed by <2 are considered indistinguishable (North, B. V., Curtis, D. and Sham, P. C. (2005) Application of logistic regression to case-control association studies involving two causative loci. Hum Hered. 59, 79-87), and the model with fewer parameters was chosen as the most parsimonious model. Since adjusting for age and gender did not affect the estimates of ORs for Y2402H nor S69A (Tables 12 and 13), and to keep number of parameters as small as possible, no adjustment was made for these covariates when modeling interaction. Based on the results of the above interaction analyses, joint ORs were calculated.

TABLE 12

Estimated crude ORs, corresponding 95% CIs, and PARs, unadjusted for age and gender

| | Dominant (RR + RN vs. NN) | | | Recessive (RR vs. RN + NN) | | | Heterozygotes (RN vs. NN) | | | Homozygotes (RR vs. NN) | | |
|---|---|---|---|---|---|---|---|---|---|---|---|---|
| | OR | 95% CI | PAR | OR | 95% CI | PAR | OR | 95% CI | PAR | OR | 95% CI | PAR |
| CFH (Y402H) | | | | | | | | | | | | |
| 1 vs. 345 | 3.73 | 2.60  5.34 | 0.60 | 3.69 | 2.37  5.75 | 0.22 | 2.66 | 1.81  3.92 | 0.43 | 6.69 | 4.08  10.98 | 0.37 |
| 1 vs. 45 | 3.94 | 2.72  5.71 | 0.62 | 3.74 | 2.39  5.85 | 0.22 | 2.82 | 1.89  4.19 | 0.45 | 7.06 | 4.27  11.70 | 0.38 |
| 1 vs. 3 | 2.73 | 1.55  4.83 | 0.49 | 3.39 | 1.89  6.10 | 0.20 | 1.93 | 1.04  3.60 | 0.30 | 4.95 | 2.46  9.95 | 0.29 |
| 1 vs. 4 | 3.64 | 2.35  5.64 | 0.59 | 3.48 | 2.14  5.66 | 0.20 | 2.67 | 1.67  4.27 | 0.43 | 6.33 | 3.60  11.16 | 0.35 |
| 1 vs. 5 | 4.21 | 2.76  6.42 | 0.64 | 3.95 | 2.47  6.32 | 0.23 | 2.94 | 1.87  4.63 | 0.47 | 7.71 | 4.46  13.34 | 0.41 |
| 1 vs. 45 (GA) | 3.73 | 2.21  6.31 | 0.60 | 4.01 | 2.36  6.82 | 0.24 | 2.54 | 1.44  4.48 | 0.41 | 7.04 | 3.69  13.41 | 0.38 |
| 1 vs. 4 (GA) | 2.71 | 1.36  5.37 | 0.49 | 4.16 | 2.14  8.07 | 0.24 | 1.68 | 0.78  3.61 | 0.23 | 5.55 | 2.48  12.41 | 0.32 |
| 1 vs. 5 (GA) | 4.85 | 2.46  9.56 | 0.68 | 3.91 | 2.16  7.10 | 0.23 | 3.47 | 1.69  7.14 | 0.53 | 8.65 | 3.92  19.09 | 0.44 |
| 1 vs. 45 (NV) | 3.31 | 2.16  5.07 | 0.56 | 3.24 | 2.00  5.26 | 0.19 | 2.48 | 1.57  3.93 | 0.40 | 5.60 | 3.21  9.78 | 0.32 |
| 1 vs. 4 (NV) | 3.43 | 2.05  5.74 | 0.57 | 2.80 | 1.63  4.80 | 0.16 | 2.78 | 1.61  4.80 | 0.44 | 5.24 | 2.74  10.01 | 0.30 |
| 1 vs. 5 (NV) | 3.18 | 1.87  5.41 | 0.55 | 3.82 | 2.21  6.59 | 0.22 | 2.17 | 1.22  3.86 | 0.34 | 6.00 | 3.12  11.53 | 0.34 |
| CHS | 2.26 | 1.45  3.53 | 0.41 | 2.99 | 1.85  4.83 | 0.17 | 1.82 | 1.13  2.92 | 0.27 | 4.22 | 2.39  7.42 | 0.25 |
| ELOVL4 | | | | | | | | | | | | |
| 1 vs. 345 | 0.69 | 0.47  1.01 | −0.07 | 0.78 | 0.28  2.16 | −0.01 | 0.69 | 0.46  1.02 | −0.06 | 0.72 | 0.26  1.99 | −0.01 |
| 1 vs. 45 | 0.71 | 0.48  1.04 | −0.06 | 0.85 | 0.30  2.38 | 0.00 | 0.70 | 0.46  1.04 | −0.06 | 0.78 | 0.28  2.19 | −0.01 |
| 1 vs. 3 | 0.59 | 0.32  1.09 | −0.09 | 0.35 | 0.04  3.04 | −0.02 | 0.62 | 0.33  1.17 | −0.07 | 0.31 | 0.04  2.75 | −0.02 |
| 1 vs. 4 | 0.67 | 0.43  1.06 | −0.07 | 0.76 | 0.23  2.53 | −0.01 | 0.67 | 0.42  1.07 | −0.06 | 0.69 | 0.21  2.32 | −0.01 |
| 1 vs. 5 | 0.73 | 0.48  1.12 | −0.06 | 0.92 | 0.30  2.80 | 0.00 | 0.72 | 0.46  1.12 | −0.05 | 0.85 | 0.28  2.60 | 0.00 |
| 1 vs. 45 (GA) | 0.59 | 0.35  1.00 | −0.09 | 0.91 | 0.24  3.47 | 0.00 | 0.56 | 0.32  0.99 | −0.08 | 0.81 | 0.21  3.08 | 0.00 |
| 1 vs. 4 (GA) | 0.63 | 0.31  1.29 | −0.08 | 1.13 | 0.21  5.99 | 0.00 | 0.58 | 0.27  1.26 | −0.09 | 1.00 | 0.19  5.36 | 0.00 |
| 1 vs. 5 (GA) | 0.56 | 0.30  1.06 | −0.10 | 0.77 | 0.15  4.04 | −0.01 | 0.55 | 0.28  1.07 | −0.09 | 0.67 | 0.13  3.57 | −0.01 |
| 1 vs. 45 (NV) | 0.65 | 0.42  1.01 | −0.07 | 0.36 | 0.09  1.55 | −0.02 | 0.69 | 0.43  1.09 | −0.06 | 0.33 | 0.08  1.42 | −0.02 |
| 1 vs. 4 (NV) | 0.71 | 0.42  1.18 | −0.06 | 0.67 | 0.16  2.84 | −0.01 | 0.72 | 0.42  1.22 | −0.05 | 0.62 | 0.14  2.64 | −0.01 |
| 1 vs. 5 (NV) | 0.58 | 0.33  1.03 | −0.09 | — | — — | — | 0.65 | 0.37  1.15 | −0.06 | — | — — | — |
| CHS | 1.41 | 0.92  2.17 | 0.07 | 0.33 | 0.04  2.43 | −0.02 | 1.55 | 1.00  2.41 | 0.09 | 0.36 | 0.05  2.68 | −0.02 |
| PLEKHA1 (A320T) | | | | | | | | | | | | |
| 1 vs. 345 | 0.57 | 0.40  0.81 | −0.39 | 0.37 | 0.23  0.60 | −0.13 | 0.68 | 0.47  0.99 | −0.18 | 0.31 | 0.18  0.51 | −0.14 |
| 1 vs. 45 | 0.56 | 0.39  0.81 | −0.40 | 0.39 | 0.24  0.63 | −0.12 | 0.67 | 0.46  0.98 | −0.19 | 0.31 | 0.19  0.53 | −0.14 |
| 1 vs. 3 | 0.62 | 0.37  1.05 | −0.33 | 0.28 | 0.11  0.70 | −0.15 | 0.78 | 0.46  1.35 | −0.12 | 0.25 | 0.09  0.64 | −0.16 |
| 1 vs. 4 | 0.68 | 0.46  1.02 | −0.26 | 0.62 | 0.37  1.04 | −0.07 | 0.75 | 0.49  1.15 | −0.13 | 0.53 | 0.30  0.94 | −0.09 |
| 1 vs. 5 | 0.48 | 0.33  0.71 | −0.51 | 0.22 | 0.12  0.42 | −0.16 | 0.61 | 0.41  0.92 | −0.23 | 0.17 | 0.09  0.34 | −0.17 |
| 1 vs. 45 (GA) | 0.70 | 0.44  1.12 | −0.24 | 0.42 | 0.21  0.83 | −0.12 | 0.84 | 0.52  1.37 | −0.08 | 0.38 | 0.18  0.80 | −0.12 |
| 1 vs. 4 (GA) | 0.66 | 0.36  1.21 | −0.29 | 0.57 | 0.24  1.38 | −0.08 | 0.73 | 0.38  1.40 | −0.15 | 0.48 | 0.19  1.24 | −0.10 |
| 1 vs. 5 (GA) | 0.74 | 0.43  1.27 | −0.20 | 0.32 | 0.13  0.79 | −0.14 | 0.92 | 0.53  1.63 | −0.04 | 0.30 | 0.12  0.80 | −0.14 |
| 1 vs. 45 (NV) | 0.50 | 0.33  0.74 | −0.49 | 0.45 | 0.26  0.78 | −0.11 | 0.57 | 0.37  0.87 | −0.26 | 0.34 | 0.19  0.61 | −0.13 |
| 1 vs. 4 (NV) | 0.65 | 0.41  1.02 | −0.30 | 0.68 | 0.37  1.24 | −0.06 | 0.69 | 0.42  1.12 | −0.18 | 0.56 | 0.29  1.07 | −0.09 |
| 1 vs. 5 (NV) | 0.37 | 0.23  0.59 | −0.71 | 0.21 | 0.08  0.51 | −0.16 | 0.46 | 0.28  0.76 | −0.35 | 0.14 | 0.06  0.36 | −0.18 |
| CHS | 0.76 | 0.52  1.11 | −0.19 | 0.68 | 0.39  1.18 | −0.06 | 0.81 | 0.54  1.21 | −0.10 | 0.61 | 0.34  1.10 | −0.07 |

TABLE 12-continued

Estimated crude ORs, corresponding 95% CIs, and PARs, unadjusted for age and gender

| | Dominant (RR + RN vs. NN) | | | Recessive (RR vs. RN + NN) | | | Heterozygotes (RN vs. NN) | | | Homozygotes (RR vs. NN) | | |
|---|---|---|---|---|---|---|---|---|---|---|---|---|
| | OR | 95% CI | PAR | OR | 95% CI | PAR | OR | 95% CI | PAR | OR | 95% CI | PAR |
| LOC387715 (S69A) | | | | | | | | | | | | |
| 1 vs. 345 | 3.99 | 2.81 5.67 | 0.54 | 10.16 | 3.70 27.88 | 0.28 | 3.06 | 2.13 4.39 | 0.42 | 17.26 | 6.22 47.89 | 0.41 |
| 1 vs. 45 | 4.17 | 2.92 5.96 | 0.56 | 10.52 | 3.83 28.93 | 0.29 | 3.18 | 2.20 4.60 | 0.43 | 18.30 | 6.57 50.93 | 0.43 |
| 1 vs. 3 | 3.07 | 1.82 5.17 | 0.45 | 7.97 | 2.56 24.81 | 0.23 | 2.45 | 1.42 4.23 | 0.34 | 11.89 | 3.70 38.19 | 0.32 |
| 1 vs. 4 | 2.72 | 1.83 4.05 | 0.41 | 5.64 | 1.95 16.27 | 0.17 | 2.34 | 1.55 3.53 | 0.32 | 8.19 | 2.80 24.00 | 0.24 |
| 1 vs. 5 | 6.14 | 4.11 9.19 | 0.67 | 15.07 | 5.43 41.82 | 0.38 | 4.32 | 2.85 6.57 | 0.54 | 32.07 | 11.30 91.01 | 0.57 |
| 1 vs. 45 (GA) | 3.29 | 2.07 5.21 | 0.48 | 6.28 | 2.09 18.93 | 0.19 | 2.81 | 1.74 4.52 | 0.39 | 10.14 | 3.28 31.31 | 0.28 |
| 1 vs. 4 (GA) | 3.06 | 1.66 5.65 | 0.45 | 4.75 | 1.29 17.49 | 0.14 | 2.74 | 1.46 5.17 | 0.38 | 7.57 | 1.97 29.06 | 0.22 |
| 1 vs. 5 (GA) | 3.46 | 2.01 5.94 | 0.49 | 7.38 | 2.33 23.38 | 0.22 | 2.86 | 1.63 5.02 | 0.40 | 12.02 | 3.65 39.57 | 0.32 |
| 1 vs. 45 (NV) | 4.09 | 2.73 6.12 | 0.55 | 8.62 | 3.05 24.39 | 0.25 | 3.30 | 2.17 5.01 | 0.45 | 15.34 | 5.32 44.25 | 0.38 |
| 1 vs. 4 (NV) | 2.71 | 1.72 4.27 | 0.40 | 4.42 | 1.42 13.74 | 0.13 | 2.44 | 1.53 3.90 | 0.34 | 6.58 | 2.07 20.90 | 0.19 |
| 1 vs. 5 (NV) | 7.21 | 4.24 12.27 | 0.71 | 14.44 | 4.96 41.99 | 0.37 | 5.24 | 3.02 9.10 | 0.60 | 35.22 | 11.47 108.17 | 0.60 |
| CHS | 1.93 | 1.32 2.83 | 0.27 | 3.91 | 2.17 7.03 | 0.11 | 1.58 | 1.05 2.39 | 0.17 | 4.75 | 2.56 8.80 | 0.14 |

NOTE

N denotes the normal allele and R denotes the risk allele. The risk allele is defined as the least frequent allele in controls.

The OR for dominance effects compares those who carry one risk allele (RN and RR genotypes) to individuals homozygote for the normal allele (NN), the OR for recessice effects compares individuals with RR genotype to those who carry one normal allele (NN and RN genotypes).

Hetero- and homozygote ORs compare individuals with one (RN) and two (RR) risk alleles to individuals with NN genotype, respectively.

GA = geographic atrophy.

CNV = choroidal neovascular membranes.

TABLE 13

Estimated ORs, corresponding 95% CIs, and PARs, adjusted for age and gender

| | Dominant (RR + RN vs. NN) | | | Recessive (RR vs. RN + NN) | | | Heterozygotes (RN vs. NN) | | | Homozygotes (RR vs. NN) | | |
|---|---|---|---|---|---|---|---|---|---|---|---|---|
| | OR | 95% CI | PAR | OR | 95% CI | PAR | OR | 95% CI | PAR | OR | 95% CI | PAR |
| CFH (Y402H) | | | | | | | | | | | | |
| 1 vs. 345 | 3.52 | 2.43 5.10 | 0.58 | 3.78 | 2.40 5.95 | 0.22 | 2.47 | 1.66 3.68 | 0.40 | 6.43 | 3.88 10.64 | 0.36 |
| 1 vs. 45 | 3.69 | 2.51 5.41 | 0.60 | 3.79 | 2.40 6.00 | 0.22 | 2.60 | 1.72 3.93 | 0.42 | 6.71 | 4.01 11.23 | 0.37 |
| 1 vs. 3 | 2.73 | 1.52 4.91 | 0.49 | 3.73 | 2.01 6.91 | 0.22 | 1.88 | 0.99 3.59 | 0.28 | 5.23 | 2.53 10.83 | 0.30 |
| 1 vs. 4 | 3.41 | 2.18 5.32 | 0.57 | 3.73 | 2.26 6.14 | 0.22 | 2.41 | 1.48 3.90 | 0.39 | 6.20 | 3.50 10.97 | 0.35 |
| 1 vs. 5 | 4.17 | 2.66 6.53 | 0.64 | 3.85 | 2.35 6.32 | 0.23 | 2.95 | 1.83 4.78 | 0.47 | 7.69 | 4.25 13.90 | 0.41 |
| 1 vs. 45 (GA) | 3.54 | 2.07 6.07 | 0.58 | 3.87 | 2.24 6.69 | 0.23 | 2.44 | 1.37 4.36 | 0.39 | 6.60 | 3.43 12.71 | 0.36 |
| 1 vs. 4 (GA) | 2.62 | 1.31 5.24 | 0.47 | 4.12 | 2.10 8.11 | 0.24 | 1.63 | 0.75 3.54 | 0.22 | 5.46 | 2.43 12.25 | 0.31 |
| 1 vs. 5 (GA) | 4.86 | 2.41 9.82 | 0.68 | 3.71 | 1.98 6.94 | 0.22 | 3.55 | 1.69 7.47 | 0.53 | 8.51 | 3.68 19.68 | 0.43 |
| 1 vs. 45 (NV) | 3.16 | 2.02 4.95 | 0.54 | 3.42 | 2.06 5.67 | 0.20 | 2.33 | 1.44 3.76 | 0.37 | 5.47 | 3.07 9.75 | 0.31 |
| 1 vs. 4 (NV) | 3.30 | 1.95 5.59 | 0.56 | 3.11 | 1.77 5.44 | 0.18 | 2.57 | 1.46 4.53 | 0.41 | 5.27 | 2.73 10.16 | 0.30 |
| 1 vs. 5 (NV) | 3.10 | 1.74 5.52 | 0.54 | 3.90 | 2.14 7.10 | 0.23 | 2.11 | 1.13 3.94 | 0.33 | 6.04 | 2.93 12.49 | 0.34 |
| CHS | 2.10 | 1.34 3.31 | 0.38 | 3.12 | 1.90 5.15 | 0.18 | 1.65 | 1.02 2.67 | 0.23 | 4.19 | 2.34 7.52 | 0.25 |
| ELOVL4 | | | | | | | | | | | | |
| 1 vs. 345 | 0.68 | 0.46 1.01 | −0.07 | 0.68 | 0.24 1.95 | −0.01 | 0.69 | 0.46 1.04 | −0.06 | 0.64 | 0.22 1.83 | −0.01 |
| 1 vs. 45 | 0.70 | 0.47 1.05 | −0.06 | 0.76 | 0.26 2.19 | −0.01 | 0.70 | 0.46 1.07 | −0.05 | 0.71 | 0.24 2.05 | −0.01 |
| 1 vs. 3 | 0.62 | 0.33 1.17 | −0.08 | 0.31 | 0.03 2.76 | −0.02 | 0.66 | 0.35 1.27 | −0.06 | 0.28 | 0.03 2.56 | −0.02 |
| 1 vs. 4 | 0.68 | 0.43 1.07 | −0.07 | 0.72 | 0.21 2.48 | −0.01 | 0.68 | 0.42 1.10 | −0.06 | 0.68 | 0.20 2.33 | −0.01 |
| 1 vs. 5 | 0.73 | 0.46 1.16 | −0.06 | 0.76 | 0.24 2.46 | −0.01 | 0.74 | 0.46 1.19 | −0.05 | 0.71 | 0.22 2.29 | −0.01 |
| 1 vs. 45 (GA) | 0.59 | 0.34 1.03 | −0.09 | 0.68 | 0.17 2.70 | −0.01 | 0.59 | 0.33 1.06 | −0.08 | 0.61 | 0.15 2.45 | −0.01 |
| 1 vs. 4 (GA) | 0.64 | 0.31 1.33 | −0.08 | 0.92 | 0.17 5.05 | 0.00 | 0.61 | 0.28 1.33 | −0.07 | 0.84 | 0.15 4.61 | 0.00 |
| 1 vs. 5 (GA) | 0.55 | 0.28 1.08 | −0.10 | 0.57 | 0.10 3.23 | −0.01 | 0.56 | 0.28 1.14 | −0.08 | 0.52 | 0.09 2.93 | −0.01 |
| 1 vs. 45 (NV) | 0.68 | 0.43 1.08 | −0.07 | 0.37 | 0.08 1.68 | −0.02 | 0.72 | 0.44 1.16 | −0.05 | 0.35 | 0.08 1.57 | −0.01 |
| 1 vs. 4 (NV) | 0.68 | 0.40 1.16 | −0.07 | 0.66 | 0.15 2.91 | −0.01 | 0.69 | 0.40 1.20 | −0.06 | 0.61 | 0.14 2.69 | −0.01 |
| 1 vs. 5 (NV) | 0.71 | 0.38 1.30 | −0.06 | — | — — | — | 0.80 | 0.43 1.50 | −0.04 | — | — — | — |
| CHS | 1.35 | 0.87 2.11 | 0.07 | 0.27 | 0.03 2.15 | −0.02 | 1.51 | 0.96 2.37 | 0.08 | 0.29 | 0.04 2.33 | −0.02 |
| PLEKHA1 (A320T) | | | | | | | | | | | | |
| 1 vs. 345 | 0.61 | 0.43 0.88 | −0.34 | 0.40 | 0.25 0.65 | −0.12 | 0.73 | 0.50 1.08 | −0.15 | 0.34 | 0.20 0.57 | −0.13 |
| 1 vs. 45 | 0.61 | 0.42 0.88 | −0.35 | 0.41 | 0.25 0.68 | −0.12 | 0.72 | 0.48 1.06 | −0.16 | 0.35 | 0.20 0.59 | −0.13 |
| 1 vs. 3 | 0.70 | 0.41 1.19 | −0.25 | 0.30 | 0.12 0.76 | −0.14 | 0.87 | 0.50 1.52 | −0.07 | 0.27 | 0.10 0.72 | −0.15 |
| 1 vs. 4 | 0.71 | 0.47 1.08 | −0.23 | 0.69 | 0.40 1.18 | −0.06 | 0.76 | 0.49 1.18 | −0.13 | 0.57 | 0.32 1.02 | −0.08 |
| 1 vs. 5 | 0.55 | 0.36 0.82 | −0.42 | 0.19 | 0.10 0.38 | −0.17 | 0.71 | 0.46 1.09 | −0.16 | 0.16 | 0.08 0.33 | −0.18 |
| 1 vs. 45 (GA) | 0.75 | 0.47 1.21 | −0.19 | 0.44 | 0.22 0.88 | −0.11 | 0.90 | 0.54 1.48 | −0.05 | 0.41 | 0.19 0.88 | −0.12 |
| 1 vs. 4 (GA) | 0.68 | 0.37 1.27 | −0.26 | 0.59 | 0.24 1.44 | −0.08 | 0.77 | 0.40 1.50 | −0.12 | 0.47 | 0.18 1.23 | −0.10 |

TABLE 13-continued

Estimated ORs, corresponding 95% CIs, and PARs, adjusted for age and gender

| | Dominant (RR + RN vs. NN) | | | | Recessive (RR vs. RN + NN) | | | | Heterozygotes (RN vs. NN) | | | | Homozygotes (RR vs. NN) | | | |
|---|---|---|---|---|---|---|---|---|---|---|---|---|---|---|---|---|
| | OR | 95% CI | | PAR | OR | 95% CI | | PAR | OR | 95% CI | | PAR | OR | 95% CI | | PAR |
| 1 vs. 5 (GA) | 0.84 | 0.47 | 1.48 | −0.12 | 0.31 | 0.12 | 0.80 | −0.14 | 1.04 | 0.58 | 1.89 | 0.02 | 0.32 | 0.12 | 0.89 | −0.14 |
| 1 vs. 45 (NV) | 0.55 | 0.36 | 0.83 | −0.42 | 0.48 | 0.27 | 0.86 | −0.10 | 0.62 | 0.40 | 0.97 | −0.22 | 0.38 | 0.20 | 0.70 | −0.12 |
| 1 vs. 4 (NV) | 0.68 | 0.42 | 1.08 | −0.27 | 0.75 | 0.41 | 1.39 | −0.05 | 0.70 | 0.42 | 1.16 | −0.17 | 0.60 | 0.31 | 1.16 | −0.08 |
| 1 vs. 5 (NV) | 0.46 | 0.27 | 0.76 | −0.55 | 0.18 | 0.07 | 0.48 | −0.17 | 0.59 | 0.35 | 1.02 | −0.24 | 0.14 | 0.05 | 0.39 | −0.18 |
| CHS | 0.72 | 0.49 | 1.07 | −0.22 | 0.68 | 0.39 | 1.19 | −0.06 | 0.77 | 0.51 | 1.17 | −0.12 | 0.58 | 0.32 | 1.07 | −0.08 |
| LOC387715 (S69A) | | | | | | | | | | | | | | | | |
| 1 vs. 345 | 3.91 | 2.72 | 5.62 | 0.54 | 11.02 | 3.97 | 30.56 | 0.30 | 2.94 | 2.03 | 4.27 | 0.41 | 19.51 | 6.91 | 55.09 | 0.44 |
| 1 vs. 45 | 4.03 | 2.78 | 5.83 | 0.55 | 11.52 | 4.13 | 32.08 | 0.31 | 3.00 | 2.05 | 4.39 | 0.41 | 21.25 | 7.46 | 60.54 | 0.47 |
| 1 vs. 3 | 3.19 | 1.85 | 5.49 | 0.46 | 8.35 | 2.55 | 27.38 | 0.24 | 2.59 | 1.46 | 4.60 | 0.36 | 13.61 | 3.86 | 47.97 | 0.35 |
| 1 vs. 4 | 2.67 | 1.78 | 4.02 | 0.40 | 6.29 | 2.13 | 18.52 | 0.19 | 2.26 | 1.48 | 3.45 | 0.31 | 9.50 | 3.14 | 28.69 | 0.27 |
| 1 vs. 5 | 5.88 | 3.83 | 9.03 | 0.66 | 18.13 | 6.31 | 52.08 | 0.43 | 4.00 | 2.56 | 6.25 | 0.51 | 44.22 | 14.47 | 135.13 | 0.65 |
| 1 vs. 45 (GA) | 3.05 | 1.90 | 4.89 | 0.45 | 7.41 | 2.35 | 23.39 | 0.22 | 2.53 | 1.55 | 4.14 | 0.35 | 12.30 | 3.76 | 40.22 | 0.33 |
| 1 vs. 4 (GA) | 2.91 | 1.56 | 5.41 | 0.43 | 6.12 | 1.56 | 24.05 | 0.18 | 2.55 | 1.34 | 4.84 | 0.35 | 11.81 | 2.71 | 51.45 | 0.32 |
| 1 vs. 5 (GA) | 3.14 | 1.79 | 5.51 | 0.46 | 8.83 | 2.56 | 30.43 | 0.25 | 2.52 | 1.40 | 4.54 | 0.35 | 14.26 | 3.91 | 52.00 | 0.36 |
| 1 vs. 45 (NV) | 3.90 | 2.56 | 5.94 | 0.53 | 8.85 | 3.05 | 25.70 | 0.25 | 3.13 | 2.03 | 4.85 | 0.43 | 16.84 | 5.58 | 50.84 | 0.41 |
| 1 vs. 4 (NV) | 2.64 | 1.65 | 4.21 | 0.39 | 5.13 | 1.59 | 16.54 | 0.15 | 2.34 | 1.44 | 3.80 | 0.32 | 7.72 | 2.30 | 25.96 | 0.23 |
| 1 vs. 5 (NV) | 6.61 | 3.73 | 11.72 | 0.69 | 14.65 | 4.69 | 45.82 | 0.37 | 4.85 | 2.67 | 8.80 | 0.58 | 48.87 | 13.23 | 180.53 | 0.67 |
| CHS | 1.86 | 1.26 | 2.76 | 0.25 | 4.17 | 2.25 | 7.74 | 0.12 | 1.51 | 0.99 | 2.30 | 0.15 | 5.10 | 2.66 | 9.78 | 0.15 |

NOTE
N denotes the normal allele and R denotes the risk allele. The risk allele is defined as the least frequent allele in controls.
The OR for dominance effects compares those who carry one risk allele (RN and RR genotypes) to individuals homozygote for the normal allele (NN), the OR for recessive effects compares individuals with RR genotype to those who carry one normal allele (NN and RN genotypes).
Hetero- and homozygote ORs compare individuals with one (RN) and two (RR) risk alleles to individuals with NN genotype, respectively.
GA = geographic atrophy.
CNV = choroidal neovascular membranes.

APOE Analyses

Previous studies have reported possible protective and harmful effects of the apolipoprotein E (APOE) gene in ARM. The $\epsilon 4$ allele may have protective effects (Klaver, C. C., et al. (1998) Genetic association of apolipoprotein E with age-related macular degeneration. Am J Hum Genet. 63, 200-206; Schmidt, S., et al. (2000) Association of the apolipoprotein E gene with age-related macular degeneration: possible effect modification by family history, age, and gender. Mol Vis. 6, 287-293; Schmidt, S., et al. (2002) A pooled case-control study of the apolipoprotein E (APOE) gene in age-related maculopathy. Ophthalmic Genet. 23, 209-223; Baird, P. N., et al. (2004) The epsilon2 and epsilon4 alleles of the apolipoprotein gene are associated with age-related macular degeneration. Invest Ophthalmol Vis Sci. 45, 1311-1315 and Zareparsi, S., et al. (2004) Association of apolipoprotein E alleles with susceptibility to age-related macular degeneration in a large cohort from a single center. Invest Ophthalmol Vis Sci. 45, 1306-1310), while the least frequent allele, 82, may increase the risk of ARM (Klaver, C. C., et al. (1998) and Zareparsi, S., et al. (2004). The APOE variant was genotype by CHS and its association with ARM was assessed in this study. Individuals were classified by APOE genotype into individuals with APOE-$\epsilon 3$/$\epsilon 3$ genotype, and APOE-22 and APOE-24 carriers (denoted APOE-$\epsilon 2$/*  and APOE-$\epsilon 4$/*, respectively); individuals with APOE-$\epsilon 2$/$\epsilon 4$ genotype were included in both the APOE-$\epsilon 2$/* and APOE-$\epsilon 4$/* groups. Chi-squared tests were used to test for differences in distributions of APOE-$\epsilon 3$/$\epsilon 3$ and APOE-2$\epsilon$*/, and APOE-3$\epsilon$/3$\epsilon$ and APOE-4$\epsilon$/*, genotypes in controls and cases.

Meta-Analyses

We undertook a meta-analysis approach to pool estimated OR from previously published reports on CFH and LOC387715 and the two reports presented here. Initially data were analyzed, assuming the between-study variation is due to chance, and fixed-effects model was employed. Under the fixed-effect model, the maximum likelihood estimator of the pooled OR is an average of individual estimates, weighted by the inverse of their variances, and the variance of the pooled OR is estimated by the inverse of the sum of individual weights. Meta-analyses under homogeneity were performed in R (RDevelopmentCoreTeam (2005) R: A language and environment for statistical computing. R Foundation for Statistical Computing, Vienna, Austria). The assumption of homogeneity was checked using a chi-squared test. However, tests of homogeneity tend to have low power, and therefore, for comparison, we also pooled the OR in a random effects setting. Meta-analyses under heterogeneity were performed using the method of restricted maximum likelihood (REML), as implemented in SAS Proc Mixed (SAS software release 8.2 [SAS Institute Inc., Cary, N.C., USA]). The pooled REML estimator is identical to the DerSimonian-Laird estimator (DerSimonian, R. and Laird, N. (1986) Meta-analysis in clinical trials. Control Clin Trials. 7, 177-188 and van Houwelingen, H. C., Arends, L. R. and Stijnen, T. (2002) Advanced methods in meta-analysis: multivariate approach and meta-regression. Stat Med. 21, 589-624). The SAS codes by van Houwelingen et al. 2002 were modified to perform the analyses under heterogeneity.

The Y402H variant within CFH has been found strongly associated with ARM in eleven studies (Edwards, A. O., et al. (2005) Complement factor H polymorphism and age-related macular degeneration. Science. 308, 421-424; Haines, J. L., et al. (2005) Complement factor H variant increases the risk of age-related macular degeneration. Science. 308, 419-421; Klein, R. J., et al. (2005) Complement factor H polymorphism in age-related macular degeneration. Science. 308, 385-389; Hageman, G. S., et al. (2005) A common haplotype in the complement regulatory gene factor H (HF1/CFH) predisposes individuals to age-related macular degeneration. Proc Natl Acad Sci USA; Conley, Y. P., et al. (2005) Candidate gene analysis suggests a role for fatty acid biosynthesis and regulation of the complement system in the etiology of age-related maculopathy. Hum Mol Genet. 14, 1991-2002; Zareparsi, S., et al. (2005) Strong association of the Y402H variant in complement factor H at 1q32 with susceptibility to age-related macular degeneration. Am J Hum Genet. 77, 149-153; Sepp, T., et al. (2006) Complement factor H variant Y402H is a major risk determinant for geographic atrophy and choroidal neovascularization in smokers and nonsmokers. Invest Ophthalmol Vis Sci. 47, 536-540; Rivera, A., et al. (2005) Hypothetical LOC387715 is a second major susceptibility gene for age-related macular degeneration, contributing independently of complement factor H to disease risk. Hum Mol Genet. 14, 3227-3236; Souied, E. H., et al. (2005) Y402H complement factor H polymorphism associated with exudative age-related macular degeneration in the French population. Mol Vis. 11, 1135-1140; Magnusson, K. P., et al. (2006) CFH Y402H confers similar risk of soft drusen and both forms of advanced AMD. PLoS Med. 3, e5 and Jakobsdottir, J., et al. (2005) Susceptibility genes for age-related maculopathy on chromosome 10q26. Am J Hum Genet. 77, 389-407); two of these eleven studies are ours, so only the results from our Jakobsdottir et al. (2005) paper, that evaluated all contrasts, were used in meta-analysis. The Klein et al. (2005) study used a small subset of the AREDS sample, and the Magnusson et al. (2006) paper only reported allele based ORs and no genotype counts. Therefore these two studies were not included. Results from the Haines et al. (2005) study were included in pooled estimates of ORs for hetero- and homozygotes; genotype counts were not available to evaluate contrasts for dominance and recessive effects. Three studies have reported highly associated variant, S69A, within the hypothetical LOC387715 (Rivera, A. et al. (2005); Jakobsdottir, et al. (2005); Schmidt et al. (2006) and Schmidt (2006) Cigarette smoking strongly modifies the association of LOC387715 and age-related macular degeneration. Am J Hum Genet. in press). All three reports on LOC387715 were included in the meta-analysis. Research participants in all studies of CFH and LOC387715 are non-Hispanic whites of European and European American descent. Tables 14 and 15 summarize the studies included in the meta-analyses of CFH and LOC387715, respectively.

TABLE 14

Characteristics of studies included in meta-analysis of Y402H in CFH

| Study and sample | Sample size[a] | Mean age (±SD)[b] | % Males | HWE[c] P-value | Frequency of the C allele |
|---|---|---|---|---|---|
| Edwards et al.[d] Discovery sample | | | | | |
| Controls | 131 | 67.6 (7.6) | 42 | 0.99 | 0.340 |
| Cases | 225 | 72.7 (10.1) | 58 | 0.42 | 0.553 |
| Replication sample | | | | | |
| Controls | 59 | 68.1 (9.0) | 35 | 0.28 | 0.390 |
| Cases | 170 | 78.2 (7.9) | 65 | 0.64 | 0.544 |
| Haines et al.[e] | | | | | |
| Controls | 185 | ≧55 | — | — | — |
| Cases | 495 | ≧55 | — | — | — |
| Zareparsi et al. | | | | | |
| Controls | 275 | ≧68 | — | 0.11 | 0.338 |
| Cases | 616 | — | — | 0.15 | 0.608 |

TABLE 14-continued

Characteristics of studies included in meta-analysis of Y402H in CFH

| Study and sample | Sample size[a] | Mean age (±SD)[b] | % Males | HWE[c] P-value | Frequency of the C allele |
|---|---|---|---|---|---|
| Hageman et al.[f] Columbia sample | | | | | |
| Controls | 272 | 68.8 (8.6) | — | 0.23 | 0.344 |
| Cases | 549 | 71.3 (8.9) | — | 0.86 | 0.538 |
| Iowa sample | | | | | |
| Controls | 131 | 78.4 (7.4) | — | 0.70 | 0.336 |
| Cases | 403 | 79.5 (7.8) | — | 0.22 | 0.589 |
| Jakobsdottir et al. | | | | | |
| Controls | 108 | 72.6 (8.9) | 47 | 0.26 | 0.310 |
| Cases | 434 | 68.9 (8.8) | 39 | 0.42 | 0.613 |
| Rivera et al.[g] Original sample | | | | | |
| Controls | 611 | 76.2 (5.3) | 38 | <0.01 | 0.382 |
| Cases | 793 | 76.3 (6.9) | 36 | 0.30 | 0.595 |
| Replication sample | | | | | |
| Controls | 335 | 68.3 (8.1) | 45 | 0.48 | 0.358 |
| Cases | 373 | 75.0 (7.5) | 35 | 0.13 | 0.617 |
| Souied et al. | | | | | |
| Controls | 91 | 74.6 (6.3) | 42 | 0.21 | 0.302 |
| Cases | 141 | 74.3 (8.0) | 38 | 0.30 | 0.564 |
| Sepp et al. | | | | | |
| Controls | 262 | 75.8 (7.8) | 42 | 0.14 | 0.363 |
| Cases | 443 | 80.3 (6.9) | 45 | 0.49 | 0.607 |
| AREDS (1 vs. 345) | | | | | |
| Controls | 173 | 76.5 (4.4) | 49 | 0.25 | 0.358 |
| Cases | 699 | 79.5 (5.2) | 42 | 0.03 | 0.612 |
| CHS | | | | | |
| Controls | 907 | 70.3 (3.9) | 43 | 0.55 | 0.327 |
| Cases | 110 | 73.2 (4.8) | 44 | 0.71 | 0.495 |

[a]Sample sizes based on total number of genotyped persons when genotype counts are available other wise on total sample size, not accounting for missing data.
[b]Mean age and corresponding standard deviation, or other summary statistic available from the orginal paper.
[c]When genotype counts are avaible P-value, derived from the exct test (implemented in R Genetics package), given.
[d]The two data sets of Edwards et al. paper are combined in the meta-analysis. HWE P-values for the combined controls and cases are 0.53 and 0.36, respectively.
[e]Results form Haines et al. paper are included in meta-analysis of ORs for hetero- and homozygote individuals. Sample sizes are based on total number of individuals, not accounting for missing genotype data at Y402H in CFH.
[f]The two data sets of Hageman et al. paper are not combined, following the orignial paper.
[g]The two data sets of Rivera et al. paper are combined in the meta-analysis. HWE P-values for the combined controls and cases are 0.03 and 0.09, respectively.

TABLE 15

Characteristics of studies included in meta-analysis of S69A in LOC387715

| Study and sample | Sample size[a] | Mean age (±SD)[b] | % Males | HWE[c] P-value | Frequency of the T allele |
|---|---|---|---|---|---|
| Jakobsdottir et al. | | | | | |
| Controls | 106 | 72.6 (8.9) | 47 | 0.21 | 0.193 |
| Cases | 456 | 68.9 (8.8) | 39 | 0.06 | 0.485 |
| Rivera et al.[d] Original sample | | | | | |
| Controls | 594 | 76.2 (5.3) | 38 | 0.30 | 0.196 |
| Cases | 759 | 76.3 (6.9) | 36 | 0.14 | 0.417 |

TABLE 15-continued

Characteristics of studies included in meta-analysis of S69A in LOC387715

| Study and sample | Sample size[a] | Mean age (±SD)[b] | % Males | HWE[c] P-value | Frequency of the T allele |
|---|---|---|---|---|---|
| Replication sample | | | | | |
| Controls | 328 | 68.3 (8.1) | 45 | 0.75 | 0.215 |
| Cases | 361 | 75.0 (7.5) | 35 | 0.01 | 0.460 |
| Schmidt et al.[e] | | | | | |
| Controls | 186 | 66.7 (8.1) | 43 | 0.55 | 0.247 |
| Cases | 758 | 76.8 (7.7) | 35 | <0.01 | 0.427 |
| AREDS (1 vs. 345) | | | | | |
| Controls | 172 | 76.5 (4.4) | 49 | 0.45 | 0.189 |
| Cases | 693 | 79.5 (5.2) | 42 | 0.99 | 0.441 |
| CHS | | | | | |
| Controls | 995 | 70.3 (3.9) | 43 | 0.41 | 0.220 |
| Cases | 120 | 73.2 (4.8) | 44 | 0.24 | 0.354 |

[a]Sample sizes based on total number of genotyped persons when genotype counts are available other wise on total sample size, not accounting for missing data.
[b]Mean age and corresponding standard deviation, or other summary statistic available from the orginal paper.
[c]When genotype counts are avaible P-value, derived from the exct test (implemented in R Genetics package), given.
[d]The two data sets of Rivera et al. paper are combined in the meta-analysis. HWE P-values for the combined controls and cases are 0.31 and 0.01, respectively.
[e]In the meta-analysis only grade 1 subjects are classified as controls (grade 2 subjects are dropped). The original study by Schmidt et al. classified grade 2 individudals as controls. The mean age and % males of controls is taken from the paper and based on both grade 1 and 2

Results

To further evaluate CFH, ELOVL4, PLEKHA1, and LOC387715 in ARM, we genotyped previously reported SNPs within all four genes in samples from the AREDS and CHS studies. Separate analyses were performed on each data set, using total of 701 non-Hispanic white ARM patients and 175 controls from the AREDS study, and total of 126 non-Hispanic white ARM patients and 1051 controls from the CHS study (see, Table 10 for sample sizes and other characteristics of the data, and Table 16 for genotype frequencies). The disease status of subjects at their last follow-up visit was the primary endpoint evaluated for AREDS subjects. The AREDS subjects include controls of grade 1 and cases (grades 3-5) with moderate ARM and advanced ARM in one or both eyes. The ARM disease status of CHS subjects was evaluated by a single expert, for consistency, using monocular, nonmydriatic fundus photographs taken at the 8-year follow-up visit. The majority of CHS cases had moderate ARM including multiple drusen with and without pigment epithelial changes (equivalent to AREDS grade 3) with a small number of cases having geographic atrophy (GA) or choroidal neovascular membranes (CNV) and the CHS controls are of AREDS grade 1 with the exclusion of those cases with significant extramacular drusen.

TABLE 16

Genotype distribution by ARM status in AREDS and CHS cohorts.

| Gene (Variant) and genotypes | Genotype frequencies in | | | | |
|---|---|---|---|---|---|
| | AREDS cases (n = 701) | CHS cases (n = 126) | AREDS controls (n = 175) | CHS controls (n = 1051) | HapMap (CEU) |
| CFH (Y402H) | | | | | |
| TT | 0.170 | 0.264 | 0.434 | 0.448 | — |
| CT | 0.435 | 0.482 | 0.416 | 0.450 | — |
| CC | 0.395 | 0.255 | 0.150 | 0.103 | — |
| ELOVL4 (M299V) | | | | | |
| AA | 0.781 | 0.742 | 0.711 | 0.802 | 0.717 |
| AG | 0.195 | 0.250 | 0.259 | 0.174 | 0.233 |
| GG | 0.024 | 0.008 | 0.030 | 0.024 | 0.050 |
| PLEKHA1 (A320T) | | | | | |
| GG | 0.474 | 0.411 | 0.339 | 0.346 | 0.317 |
| AG | 0.443 | 0.460 | 0.464 | 0.476 | 0.467 |
| AA | 0.084 | 0.129 | 0.196 | 0.178 | 0.217 |
| LOC387715 (S69A) | | | | | |
| GG | 0.313 | 0.442 | 0.645 | 0.604 | 0.583 |
| GT | 0.492 | 0.408 | 0.331 | 0.353 | 0.400 |
| TT | 0.195 | 0.150 | 0.023 | 0.043 | 0.017 |

For comparison estimates from derived from the CEU population (residence of Utah with ancestry from northern and western Europe) of the International HapMap project are shown.
AREDS cases are of grades 3-5 and AREDS controls of grade 1.
Genotype counts are available by each grade and subphenotype in Table 17.
Description of the HapMap CEU populations is provided herein.

TABLE 17

Genotype distributions in AREDS and CHS cohorts, by ARM Status

| | AREDS | | | | | | | | | CHS | |
|---|---|---|---|---|---|---|---|---|---|---|---|
| | Controls | | | Cases (n = 701) | | | | | | | |
| | | | | | Grade 4 (n = 266) | | | Grade 5 (n = 339) | | | |
| Gene (Variant) and Genotype | Grade 1 (n = 175) | Grade 2[a] (n = 63) | Grade 3 (n = 96) | All | GA only | CNV only | All | GA only | CNV only | Controls (n = 1051) | Cases (n = 126) |
| CFH (Y402H) | | | | | | | | | | | |
| TT | 75 | 19 | 21 | 46 | 13 | 27 | 52 | 12 | 25 | 406 | 29 |
| CT | 72 | 35 | 39 | 118 | 21 | 72 | 147 | 40 | 52 | 408 | 53 |
| CC | 26 | 9 | 36 | 101 | 25 | 49 | 139 | 36 | 52 | 93 | 28 |
| All | 173 | 63 | 96 | 265 | 59 | 148 | 338 | 88 | 129 | 907 | 110 |

TABLE 17-continued

Genotype distributions in AREDS and CHS cohorts, by ARM Status

| Gene (Variant) and Genotype | AREDS | | | | | | | | | CHS | |
|---|---|---|---|---|---|---|---|---|---|---|---|
| | Controls | | | Cases (n = 701) | | | | | | | |
| | | | | Grade 4 (n = 266) | | | Grade 5 (n = 339) | | | | |
| | Grade 1 (n = 175) | Grade 2[a] (n = 63) | Grade 3 (n = 96) | All | GA only | CNV only | All | GA only | CNV only | Controls (n = 1051) | Cases (n = 126) |
| ELOVL4 (M299V) | | | | | | | | | | | |
| AA | 118 | 55 | 75 | 204 | 47 | 115 | 249 | 70 | 97 | 826 | 92 |
| AG | 43 | 7 | 17 | 50 | 10 | 30 | 65 | 14 | 23 | 179 | 31 |
| GG | 5 | 0 | 1 | 6 | 2 | 3 | 9 | 2 | 0 | 25 | 1 |
| All | 166 | 62 | 93 | 260 | 59 | 148 | 323 | 86 | 120 | 1030 | 124 |
| PLEKHA1 (A320T) | | | | | | | | | | | |
| GG | 57 | 24 | 42 | 111 | 25 | 65 | 169 | 34 | 73 | 355 | 51 |
| AG | 78 | 31 | 45 | 114 | 25 | 61 | 142 | 43 | 46 | 489 | 57 |
| AA | 33 | 7 | 6 | 34 | 7 | 21 | 17 | 6 | 6 | 183 | 16 |
| All | 168 | 62 | 93 | 259 | 57 | 147 | 328 | 83 | 125 | 1027 | 124 |
| LOC387715 (S69A) | | | | | | | | | | | |
| GG | 111 | 40 | 35 | 105 | 22 | 59 | 77 | 30 | 26 | 601 | 53 |
| GT | 57 | 19 | 44 | 126 | 31 | 74 | 171 | 44 | 70 | 351 | 49 |
| TT | 4 | 3 | 15 | 31 | 6 | 14 | 89 | 13 | 33 | 43 | 18 |
| All | 172 | 62 | 94 | 262 | 59 | 147 | 337 | 87 | 129 | 995 | 120 |

NOTE
Genotypes are ordered: NN - RN - RR, where N is the normal allele and R is the risk allele. The risk allele is defined as the least frequent allele in controls.
GA = geographic atrophy.
CNV = choroidal neovascular membranes.
[a]Grade 2 AREDS subjects were not included in the analysis.

Association Analyses

For each gene, CFH, ELOVL4, PLEKHA1, and LOC387715, association with ARM was assessed by a chi-squared statistic. The magnitude of the effect of each gene was estimated by odds ratios (ORs) and population attributable risks (PARs). To evaluate whether the genes confer similarly to early and advanced ARM, ORs were calculated for each grade and subtype (GA and CNV) separately using the AREDS data.

Figure 7:
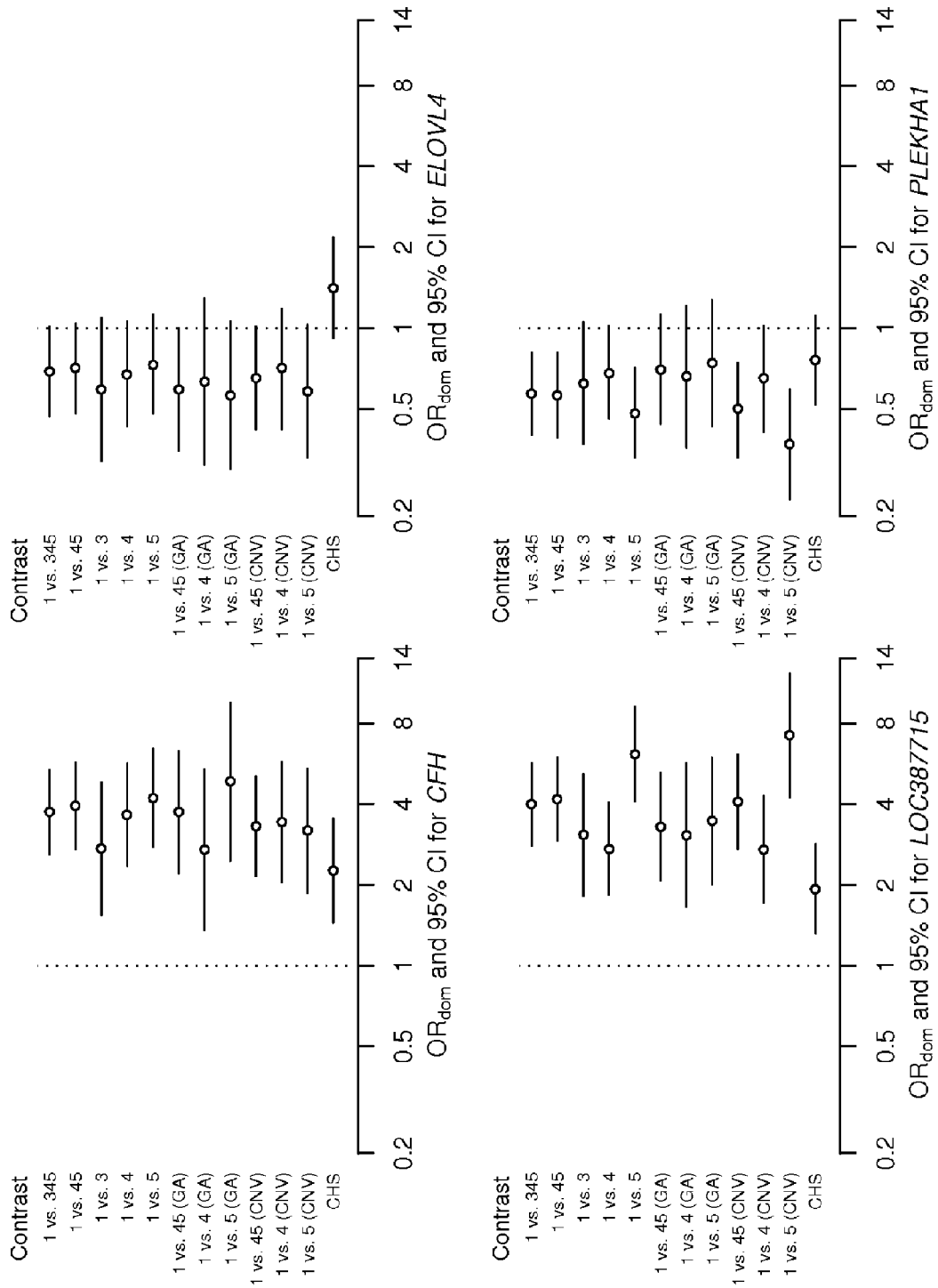
FIG. 7 shows estimated crude ORs and 95% CIs for CFH, ELOVL4, PLKEHA1, and LOC387715 genes. Carriers of one or two risk alleles (RR+RN) are compared to those subjects homozygote for the non-risk allele (NN). The solid lines denote the 95% CI corresponding to an OR (open circle). The dotted vertical line marks the null value of an OR of 1. The contrasts that were evaluated in AREDS and CHS cohorts are given on the vertical axis.

CFH: The association of the Y402H variant in CFH with ARM is significant ($P \leq 0.00001$) in both the AREDS and CHS cohorts (Table 18), confirming earlier findings by ourselves (Conley et al. (2005) and Jakobsdottir et al. (2005)) and others (Edwards et al. (2005; Haines et al. (2006); Klein et al. (2005) and Rivera et al. (2005)). The estimated ORs for Y402H in CFH suggest that the variant confers similar risk to all stages of ARM and both forms of advanced ARM, GA and CNV (FIG. 7 and Table 12).

TABLE 18

Results of allele- and genotype association tests.

| Gene (Variant) and Comparison in AREDS or CHS | CFH P-value for test | | ELOVL4 P-value for test | | PLEKHA1 P-value for test | | LOC387715 P-value for test | |
|---|---|---|---|---|---|---|---|---|
| | Allele | Genotype | Allele | Genotype[a] | Allele | Genotype | Allele | Genotype |
| AREDS | | | | | | | | |
| 1 vs. 345 | ≤0.00001 | ≤0.00001 | 0.06775 | 0.13963 | 0.00004 | 0.00004 | ≤0.00001 | ≤0.00001 |
| 1 vs. 5 | ≤0.00001 | ≤0.00001 | 0.20518 | 0.32438 | ≤0.00001 | ≤0.00001 | ≤0.00001 | ≤0.00001 |
| 1 vs. 5 (GA)[b] | ≤0.00001 | ≤0.00001 | 0.10465 | 0.21869 | 0.04131 | 0.03862 | ≤0.00001 | ≤0.00001 |
| 1 vs. 5 (CNV)[c] | ≤0.00001 | ≤0.00001 | 0.03445 | 0.04851 | ≤0.00001 | ≤0.00001 | ≤0.00001 | ≤0.00001 |
| CHS | ≤0.00001 | ≤0.00001 | 0.33832 | 0.07819 | 0.07626 | 0.22544 | ≤0.00001 | ≤0.00001 |

P-values <0.05 are bolded.
[a]2-sided P-values from Fisher's exact test.
[b]ARM cases have GA in both eyes.
[c]ARM cases have CNV in both eyes.

Figures 1, 8:
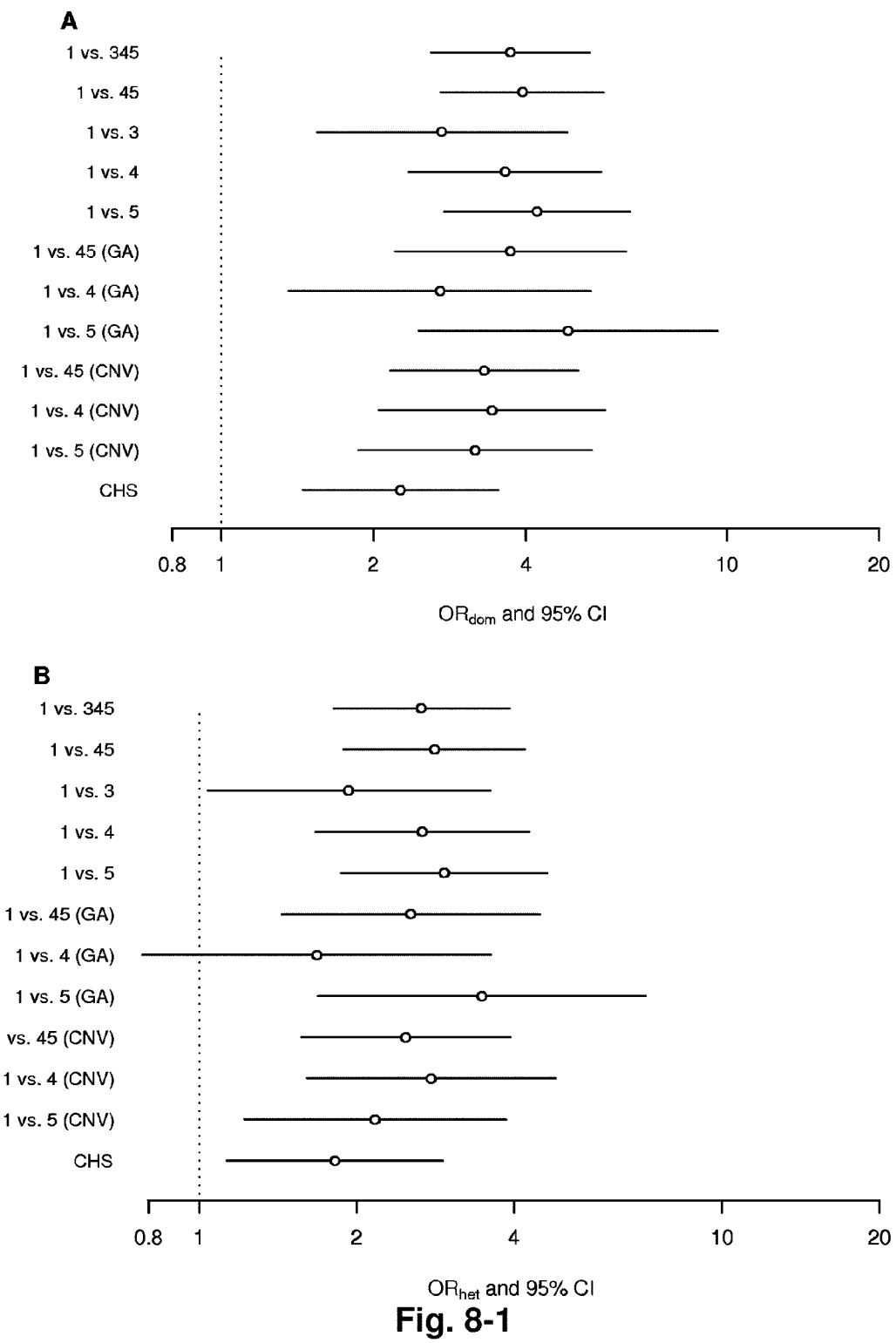
FIG. 8 shows estimated ORs and 95% CIs for CFH. A: $OR_{dom}$ for evaluation of dominance effects (CT+CC vs. TT). B: $OR_{het}$ for evaluation of the risk of heterozygotes (CT vs. TT). C: $OR_{rec}$ for evaluation of recessive effects (CC vs. CT+TT). D: $OR_{hom}$ for evaluation of the risk of homozygotes (CC vs. TT). The dotted vertical line marks the null value of OR of 1.
Figures 2, 8:
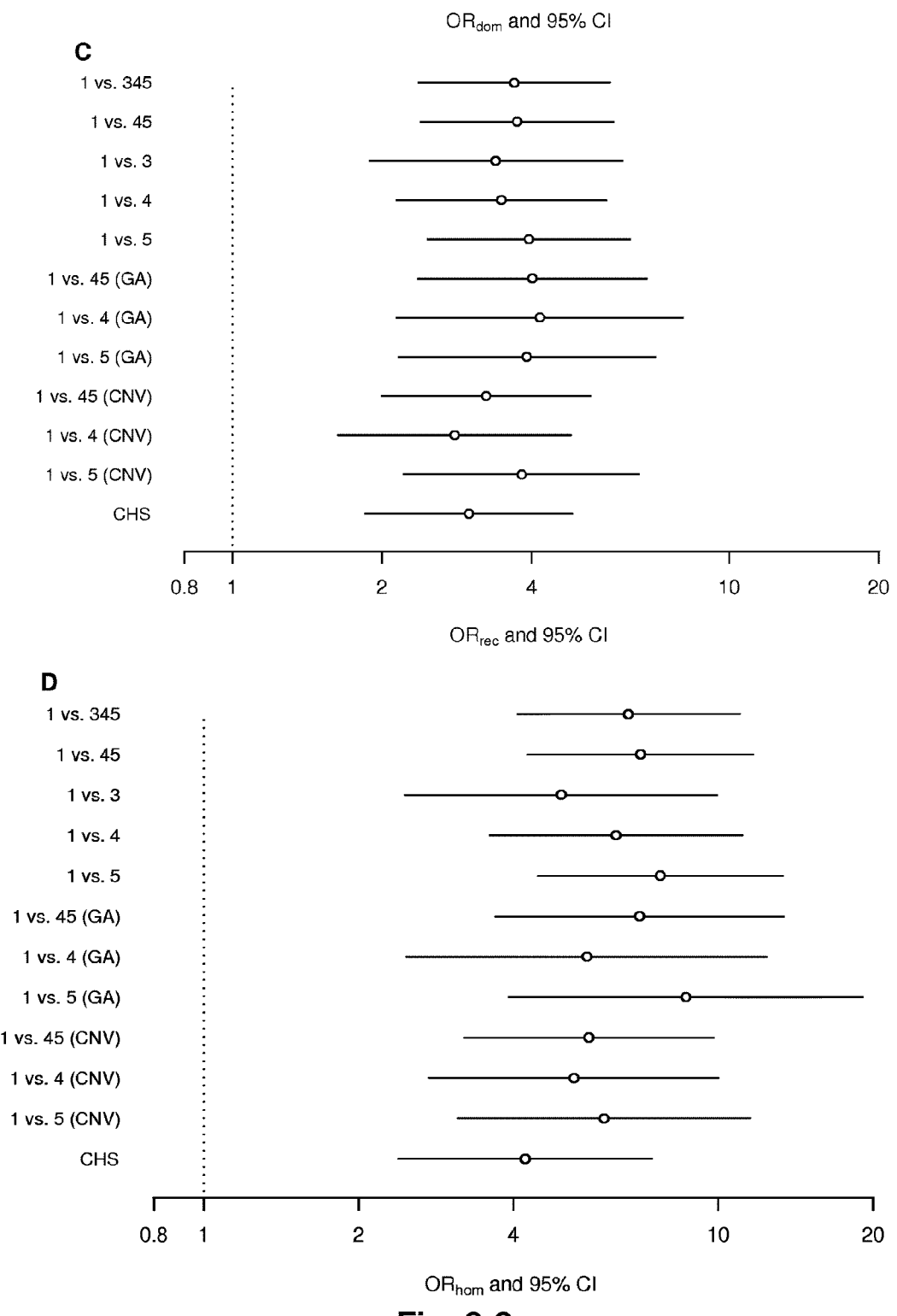
Figure 9:
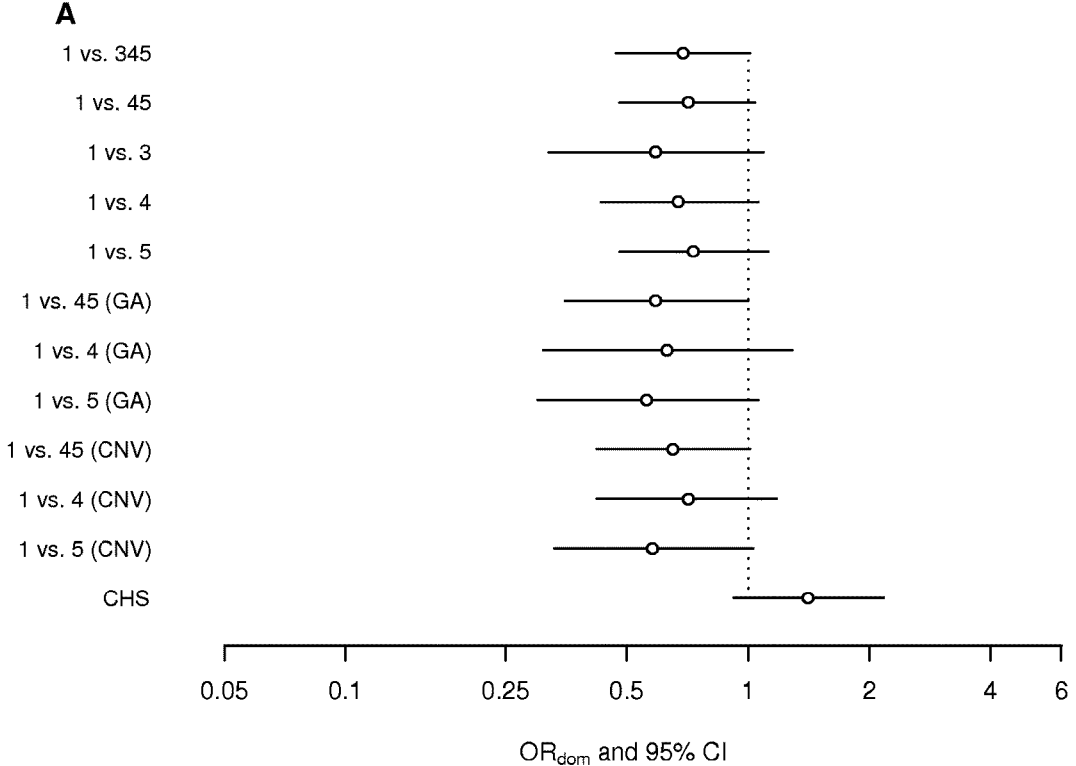
FIG. 9 shows estimated ORs and 95% CIs for ELOVL4. A: $OR_{dom}$ for evaluation of dominance effects (AG+GG vs. AA). B: $OR_{het}$ for evaluation of the risk of heterozygotes (AG vs. AA). C: $OR_{rec}$ for evaluation of recessive effects (GG vs. AG+AA). D: $OR_{hom}$ for evaluation of the risk of homozygotes (GG vs. AA). The dotted vertical line marks the null value of OR of 1.
Figure 1:
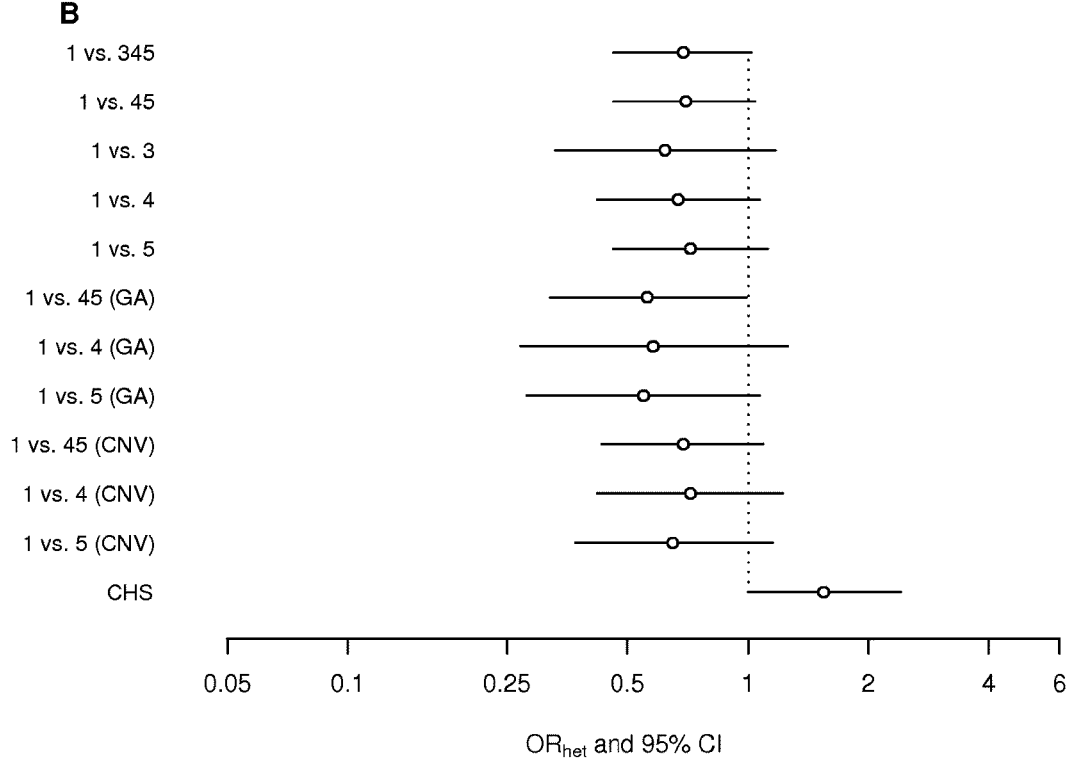
Figure 9:
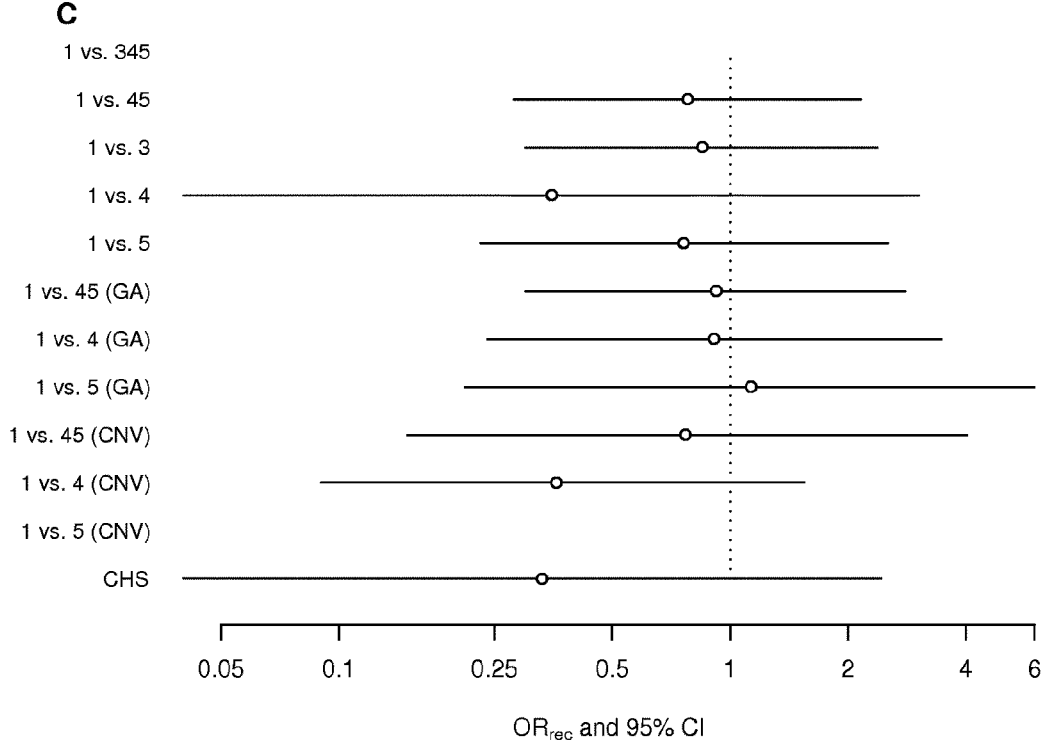
Figure 2:
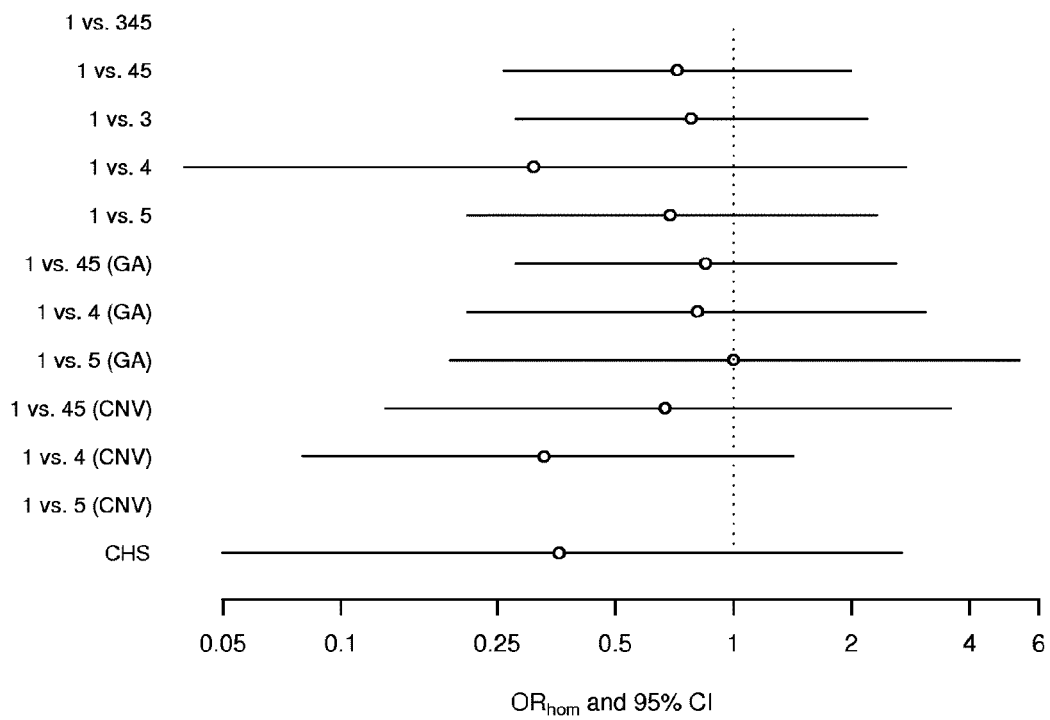

An allele-dose effect appears to be present, with carriers of two C alleles at higher risk of ARM than carriers of one C allele (Table 12 and FIG. 8). Despite the increased risk in carriers of two C alleles, the population attributable risk (PAR) is similar for the two risk genotypes, owing to relatively high frequency of the CT genotype compared to the CC genotype in the general population. PAR estimates derived from the CHS dataset suggest that the CT and CC genotypes explain 27% and 25% of ARM in the non-Hispanic white population, respectively. ELOVL4: The M299V variant in ELOVL4 is significantly associated (P=0.034) with exudative ARM in the AREDS sample (Table 18), in agreement with our previous findings (Conley, Y. P., et al. (2005). However, no ORs are statistically significant at 95% significance level (FIGS. 7 and 9 and Table 12). These results do not exclude the potential role of ELOVL4 in ARM, but do not strongly support it. The small number of individuals with exudative ARM did not allow for subphenotype analysis in the CHS cohort.

PLEKHA1 and LOC387715: The association of the S69A variant in LOC387715 with all presentations of ARM is extremely significant (P≦0.00001) in both the AREDS and CHS data sets (Table 18), confirming earlier findings by ourselves (Conley, Y. P., et al. (2005) and Jakobsdottir, J., et al. (2005)) and others (Edwards, A. O., et al. (2005); Haines, J. L., et al. (2005); Klein, R. J., et al. (2005); Rivera, A., et al. (2005) and Schmidt, S., et al. (2006)). The A320T variant in PLEKHA1, which is located on the same haplotype block as LOC387715, is highly significant (P=0.00004) in the AREDS sample but only borderline significant (P=0.08) in the CHS sample. The degree of linkage disequilibrium between A320T and S69A is statistically significant in both AREDS (D'=0.66) and CHS (D'=0.65) controls. In order to identify which gene, PLEKHA1 or LOC387715, more likely harbors the true ARM-predisposing variant, we applied the haplotype method (Valdes, A. M. and Thomson, G. (1997) Detecting disease-predisposing variants: the haplotype method. Am J Hum Genet. 60, 703-716). According to the haplotype method, the relative frequency of alleles at neutral variants is expected to be the same in cases and controls for a haplotype containing all the predisposing variants. The results based on applying the method suggest that S69A in LOC387715, and not A320T in PLEKHA1, is an ARM-predisposing variant (see "Distinguishing between PLEKHA1 and LOC387715," herein). Further, by permutation testing of the null hypothesis: $H_0$: the S69A variant in LOC387715 fully accounts for the ARM predisposition to the PLEKHA1-LOC387715 haplotype block, is not rejected (P=0.92 in the AREDS data, P=0.45 in the CHS data), while a similar hypothesis for A320T is rejected (P≦0.0001 in the AREDS data, P=0.0002 in the CHS data).

Figures 1, 10:
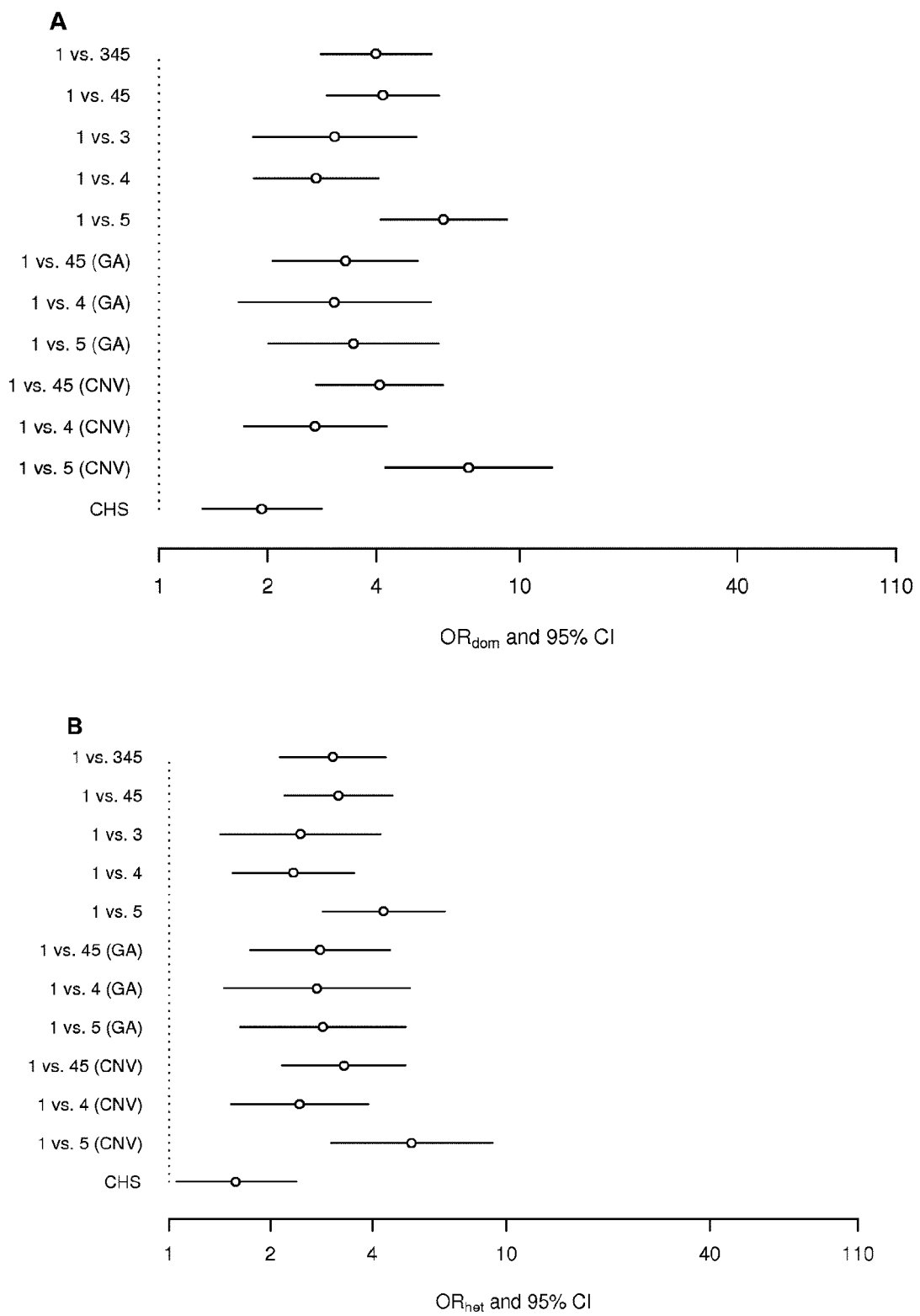
FIG. 10 shows estimated ORs and 95% CIs for LOC387715. A: $OR_{dom}$ for evaluation of dominance effects (GT+TT vs. GG). B: $OR_{het}$ for evaluation of the risk of heterozygotes (GT vs. GG). C: $OR_{rec}$ for evaluation of recessive effects (TT vs. GT+GG). D: $OR_{hom}$ for evaluation of the risk of homozygotes (TT vs. GG). The dotted vertical line marks the null value of OR of 1.
Figures 2, 10:
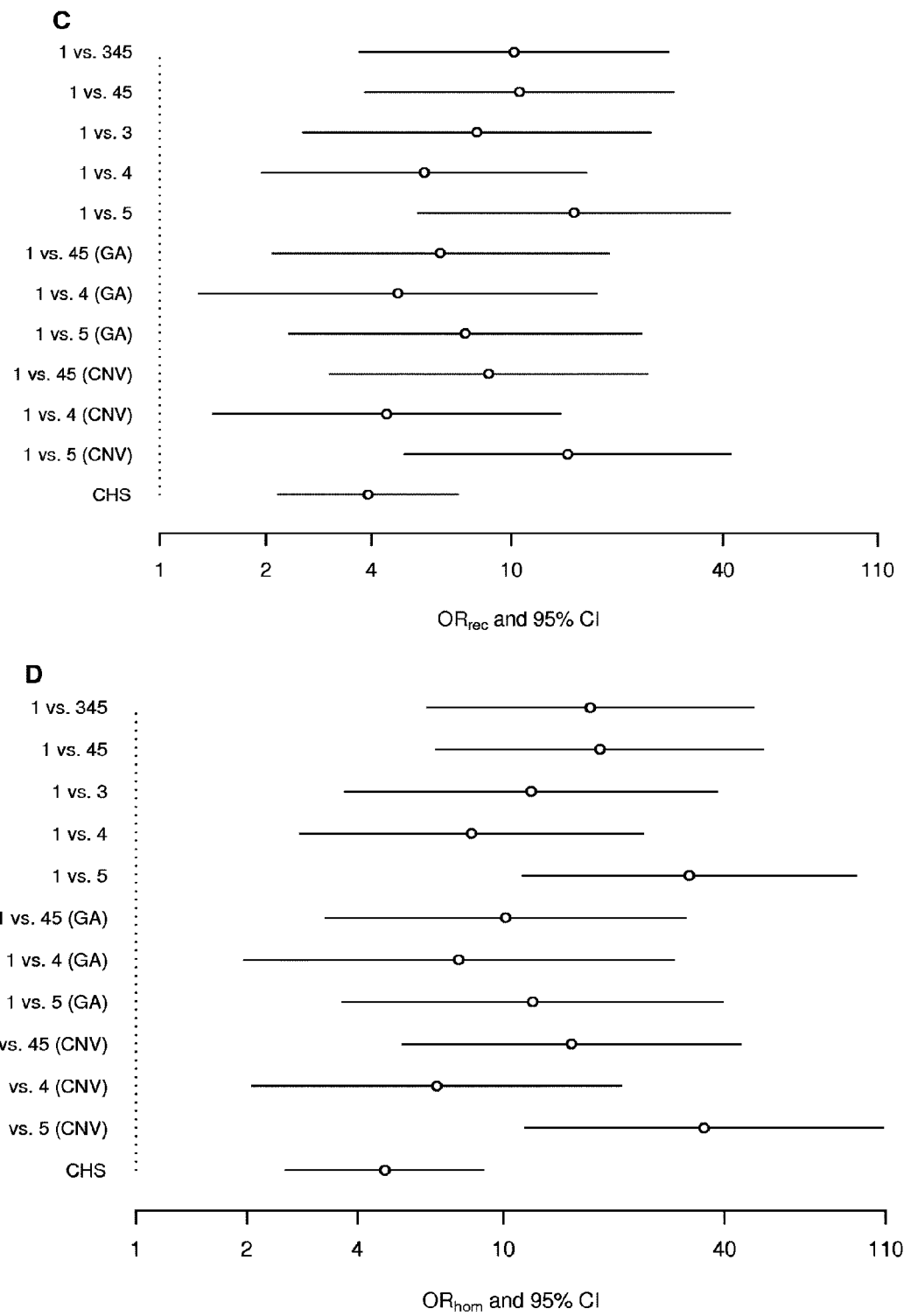
Figures 1, 11:
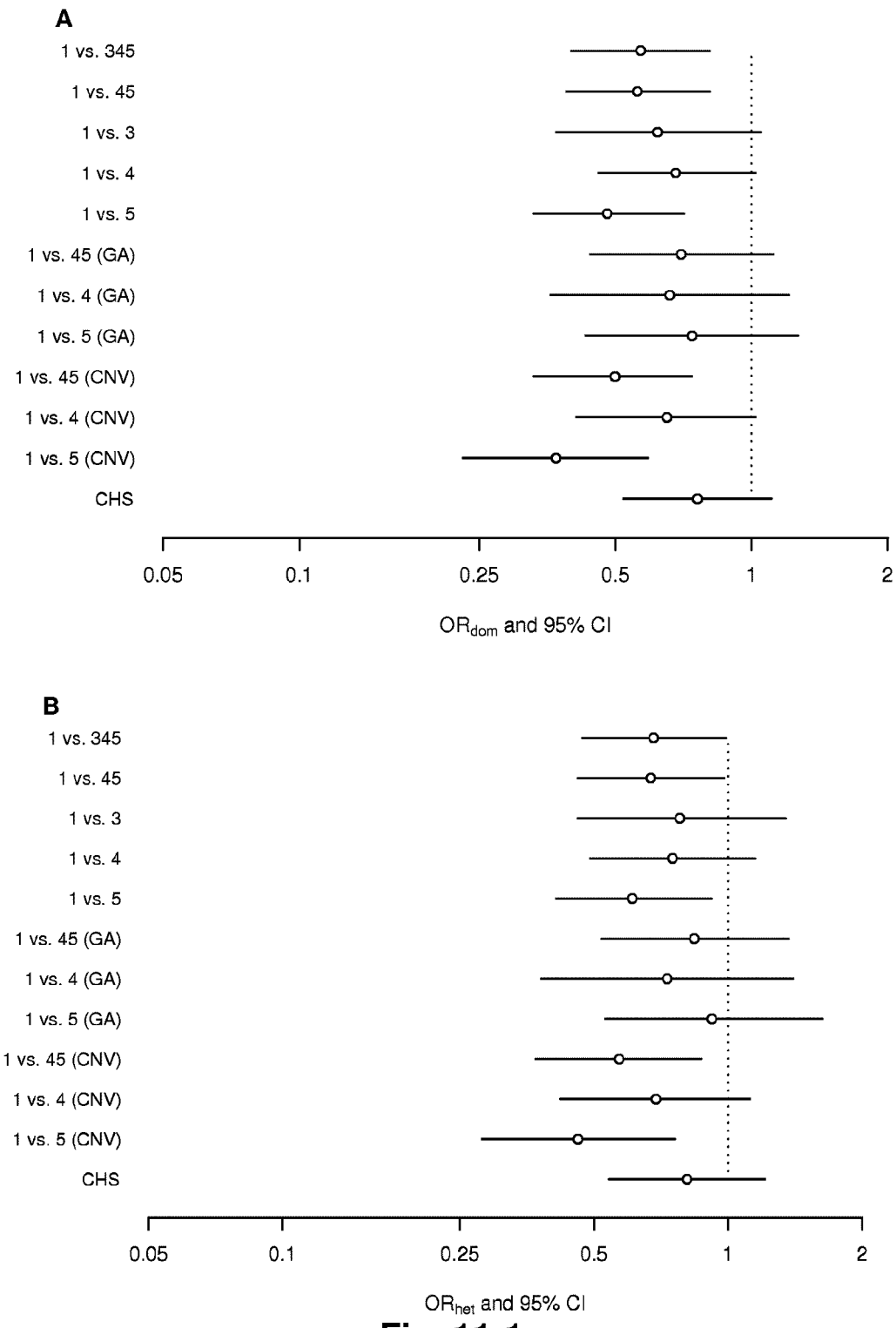
FIG. 11 shows estimated ORs and 95% CIs for PLEKHA1. A: $OR_{dom}$ for evaluation of dominance effects (AG+AA vs. GG). B: $OR_{het}$ for evaluation of the risk of heterozygotes (AG vs. GG). C: $OR_{rec}$ for evaluation of recessive effects (AA vs. AG+GG). D: $OR_{hom}$ for evaluation of the risk of homozygotes (AA vs. GG). The dotted vertical line marks the null value of OR of 1.
Figures 2, 11:
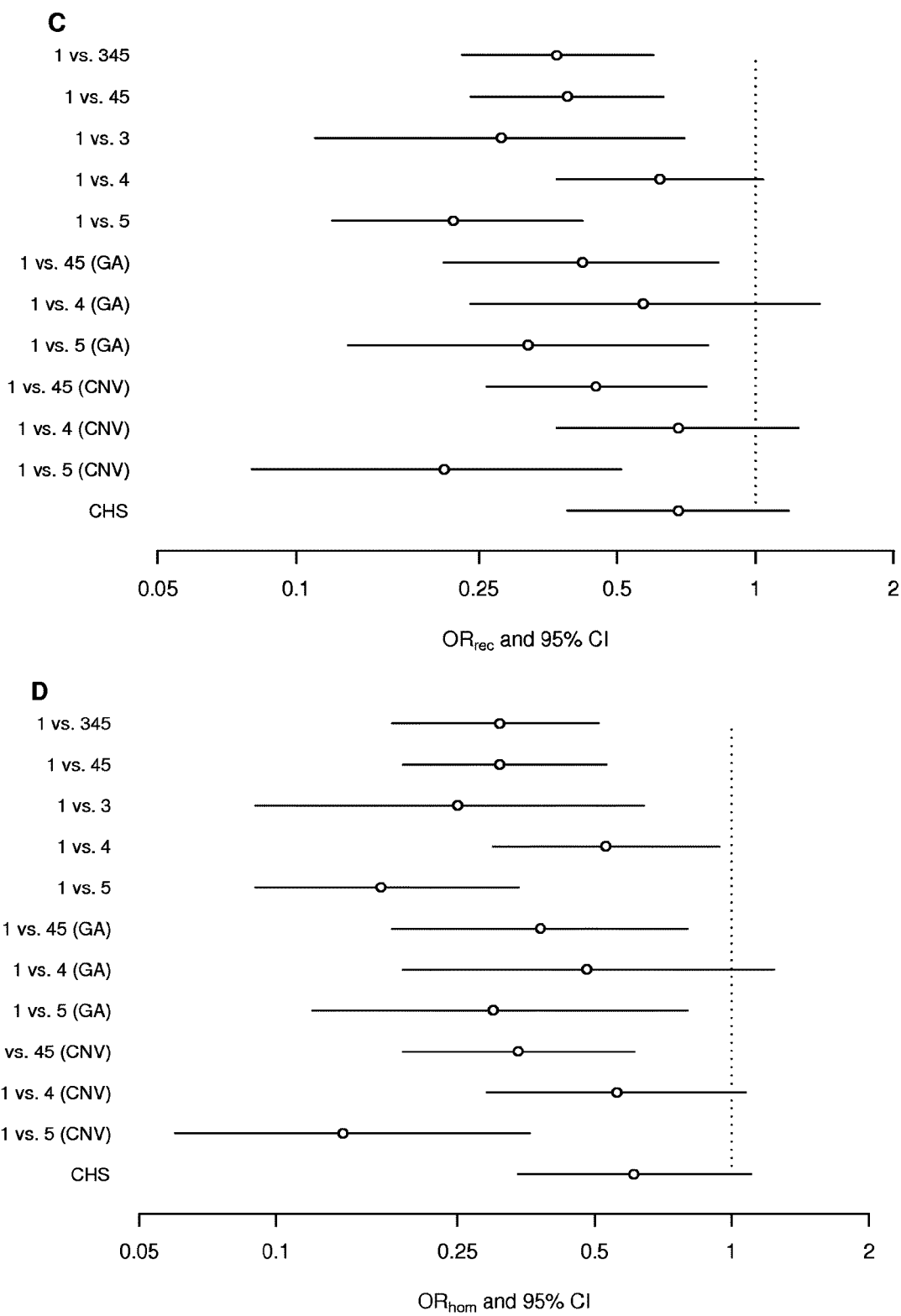

The S69A variant in LOC387715 shows different risk patterns than Y402H in CFH. The variant appears to increase the risk of severe ARM substantially more than the risk of mild ARM (FIGS. 7 and 10 [FIG. 11 gives complete results for PLEKHA1] and Table 12) in the AREDS data where severity of disease is differentiated. For example, the OR for AREDS cases of grade 3, who carry one or two T alleles, is 3.07 (95% CI 1.82-5.17), while the OR for AREDS cases, with CNV in both eyes, who carry one or two T alleles, is 7.21 (95% CI 4.24-12.27). Similar to CFH, S69A shows an allele-dose effect without dramatic differences in the population attributable risk of the GT and TT genotypes (Table 12 and FIG. 10). Since only four AREDS controls are TT homozygous at S69A, point estimates and confidence intervals, for recessive and homozygote contrasts, derived from regular logistic regression were compared to estimates from exact regression (models fitted in SAS software release 8.2 [SAS Institute Inc., Cary, N.C., USA]). These quality checks revealed no major differences in point estimates (which is the basis of the PAR estimates) and lower confidence limits (which is the basis of comparison with the ORs), but the upper confidence limits were higher (results not shown).

Interaction Analyses

We used logistic regression modeling to build a model of the joint contribution of CFH and LOC387715, CFH and cigarette smoking, and LOC387715 and cigarette smoking. A series of models were fitted in order to draw inferences about the most likely and most parsimonious model(s). As described by North et al. (2005) models were compared by using the Akaike information criterion (AIC). When the most parsimonious model had been identified we estimated joint ORs of the risk factors. Separate estimates were calculated from each cohort. In order to maximize the AREDS sample size, no subphenotype or subgrade analyses were performed; AREDS cases of grade 3-5 were compared to AREDS controls of grade 1.

In a previous paper (Jakobsdottir (2005)) we found no evidence of interacting effects of the CFH and PLEKHA1/LOC387715 loci; the joint action of the two loci was best described by independent multiplicative effects (additive on a log-scale). Rivera et al. (2005) reported that S69A in LOC387715 acted independently of Y402H in CFH. Schmidt et al. (2006a) also arrived at the same most parsimonious model, and here, again, this model is most parsimonious in both AREDS and CHS data sets (Table 19). Joint ORs for combinations of risk genotypes at Y402H and S69A were computed to further understand the joint action of the two loci (Table 20). Using all cases regardless of severity, the AREDS data suggest that individuals heterozygote for the risk allele at one of the loci and homozygote for the non-risk allele at the other are more susceptible to ARM than individuals with no risk allele at both loci (for the CT-GG joint genotype, OR 2.8, 95% CI 1.6-5.0; for the TT-GT joint genotype, OR 3.2, 95% CI 1.7-6.0). The ARM risk more then doubles if a person is heterozygote at both loci (for the CT-GT joint genotype, OR 7.2, 95% CI 3.8-13.5) and being homozygote for the risk allele for at least one of the loci further increases the risk. The joint ORs estimated from the CHS data show a similar pattern, but having only one risk allele is not sufficient to increase the risk (for the CT-GG joint genotype, OR 1.3, 95% CI 0.6-2.7; for the TT-GT joint genotype, OR 1.2, 95% CI 0.5-2.8).

TABLE 19

Results of fitting two-factor models by logistic regression.

| Two-Factor Model | AREDS data AIC | AREDS data AIC Difference | CHS data AIC | CHS data AIC Difference |
| --- | --- | --- | --- | --- |
| Y402H (Factor 1) and S69A (Factor 2) | | | | |
| ADD1 | 799.3 | 77.9 | 652.7 | 17.6 |
| ADD2 | 786.1 | 64.7 | 656.0 | 21.0 |
| ADD-BOTH | 723.0 | 1.7 | 635.1 | 0.0 |
| DOM1 | 801.2 | 79.8 | 654.4 | 19.3 |
| DOM2 | 786.9 | 65.5 | 656.0 | 21.0 |
| DOM-BOTH | 726.5 | 5.1 | 636.3 | 1.3 |
| ADD-INT | 721.4 | 0.0 | 635.8 | 0.8 |
| ADD-DOM | 724.3 | 3.0 | 638.8 | 3.8 |
| DOM-INT | — | — | 637.8 | 2.8 |
| Y402H (Factor 1) and Smoking (ever vs. never) | | | | |
| ADD1 | 787.3 | 6.0 | 677.3 | 0.0 |
| SMOKE | 848.3 | 67.0 | 700.6 | 23.3 |
| ADD1-SMOKE | 781.3 | 0.0 | 679.1 | 1.8 |
| DOM1 | 789.3 | 8.0 | 679.0 | 1.7 |
| ADD1-SMOKE-INT | 783.2 | 1.8 | 678.3 | 1.0 |
| DOM1-SMOKE-INT | 786.6 | 5.3 | 681.9 | 4.6 |
| S69A (Factor 2) and Smoking (ever vs. never) | | | | |
| ADD2 | 774.0 | 6.1 | 745.6 | 0.1 |
| SMOKE | 842.9 | 75.0 | 765.2 | 19.8 |
| ADD2-SMOKE | 767.9 | 0.0 | 747.3 | 1.8 |
| DOM2 | 774.7 | 6.7 | 745.5 | 0.0 |
| ADD2-SMOKE-INT | 769.7 | 1.8 | 749.1 | 3.7 |
| DOM2-SMOKE-INT | 772.4 | 4.4 | 748.9 | 3.4 |

Detailed model definitions are given in the "Materials and Methods - Interaction Analyses" section. AIC difference is the difference from the AIC of the best fitting model. Most parsimonious model is in bold. Model with best fit (lowest AIC) has AIC difference = 0.

TABLE 20

Joint Ors and 95% CIs at Y402H in CFH and S69A in LOC387715

| Analyzed cohort and size of sample | S69A | Main effects | OR (95% CI) for Y402H | | |
|---|---|---|---|---|---|
| | | | TT | CT | CC |
| AREDS | | | | | |
| $n_{controls}$ = 171 | | | | | |
| $n_{cases}$ = 693 | | $OR_{Y402H}$ | 1.00 (Ref) | 2.70 (1.83, 3.98) | 6.64 (4.04, 10.91) |
| | | $OR_{S69A}$ | | Joint effects | |
| | GG | 1.00 (Ref) | 1.00 (Ref) | 2.82 (1.59, 5.03) | — |
| | GT | 3.03 (2.11, 4.36) | 3.17 (1.68, 5.96) | 7.16 (3.80, 13.49) | — |
| | TT | 17.11 (6.17, 47.47) | — | — | 15.79 (8.74, 28.54) |
| CHS | | | | | |
| $n_{controls}$ = 871 | | $OR_{Y402H}$ | 1.00 (Ref) | 1.81 (1.12, 2.93) | 4.12 (2.32, 7.33) |
| $n_{cases}$ = 106 | | | | | |
| | | $OR_{S69A}$ | | Joint effects | |
| | GG | 1.00 (Ref) | 1.00 (Ref) | 1.31 (0.64, 2.69) | — |
| | GT | 1.59 (1.03, 2.47) | 1.22 (0.53, 2.83) | 2.90 (1.47, 5.73) | — |
| | TT | 4.86 (2.55, 9.26) | — | — | 4.82 (2.52, 9.23)$^a$ |

NOTE
$n_{controls}$ = number of controls fully typed at both loci,
$n_{cases}$ = number of cases fully typed at both loci.
$OR_{Y402H}$ = OR for Y402H averaged across S69A genotypes,
$OR_{S69A}$ = OR for S69A averaged across Y402H genotypes.
$^a$OR for individuals homozygote at least at one of the loci.

A recent study (Schmidt et al. (2006a)) reported a strong statistical interaction between genotypes at S69A and smoking, both on binary (ever vs. never smoked) and continuous scale (pack-years of smoking). We fail to replicate this finding in both the AREDS and CHS data sets (Table 19). Results from the AREDS sample suggests that the joint effects of Y402H and smoking are best described by independent multiplicative effects, without significant dominance or interacting effects. On the other hand, the model that best describes the CHS data includes only additive effects of Y402H. Results from the AREDS data suggest that the joint effects of S69A and smoking are best described by independent multiplicative effects, without significant dominance or interacting effects. The CHS data implicate a model with only S69A. When smoking exposure is continuous variable (pack-years of smoking) and the S69A genotypes are coded in additive fashion, the interaction term is not significant (P=0.40) in the CHS data. Pack-years of cigarette smoking were not available for participants in the AREDS study. To further understand the combined effect of the genes and cigarette smoking, joint ORs of risk genotypes at each gene and smoking were estimated from the AREDS data (Table 21). The results suggest that, while the risk of ARM due any of the risk genotypes (at Y402H and S69A) is elevated in smokers, both genes have substantially more influence on ARM risk than cigarette smoking. Both the model fitting approach and a simple chi-squared test (P=0.71) show that the main effects of cigarette smoking are insignificant (on binary scale) in the CHS data.

TABLE 21

Joint Ors and 95% CIs at Y402H in CFH and smoking, and S69A in LOC387715 and smoking

| Gene (Variant) and Genotypes | Main effects | Smoking history | |
|---|---|---|---|
| | | Never | Ever |
| AREDS cohort OR (95% CI) for | | | |
| CFH (Y402H) | $OR_{smk}$ | 1.00 (Ref) | 1.59 (1.13, 2.23) |
| $n_{controls}$ = 170 | | | |
| $n_{cases}$ = 682 | | | |
| | $OR_{Y402H}$ | Joint effects | |
| TT | 1.00 (Ref) | 1.00 (Ref) | 1.65 (0.91, 2.98) |
| CT | 2.65 (1.79, 3.90) | 2.53 (1.43, 4.48) | 4.77 (2.66, 8.54) |
| CC | 7.27 (4.37, 12.09) | 8.65 (4.03, 18.55) | 10.55 (5.14, 21.66)) |
| LOC387715 (S69A) | $OR_{smk}$ | 1.00 (Ref) | 1.57 (1.12, 2.20) |
| $n_{controls}$ = 169 | | | |
| $n_{cases}$ = 676 | | | |

TABLE 21-continued

Joint Ors and 95% CIs at Y402H in CFH and
smoking, and S69A in LOC387715 and smoking

| Gene (Variant) and Genotypes | Main effects | Smoking history | |
|---|---|---|---|
| | | Never | Ever |
| | $OR_{S69A}$ | Joint effects | |
| GG | 1.00 (Ref) | 1.00 (Ref) | 1.77 (1.11, 2.83) |
| GT | 2.98 (2.07, 4.29) | 3.19 (1.87, 5, 41) | 5.06 (2.99, 8.55) |
| TT | 17.02 (6.13, 47.26) | 21.15 (4.96, 90.22) | 25.74 (6.06, 109.34) |

| CHS cohort OR (95% CI) for | | | |
|---|---|---|---|
| CFH (Y402H) $n_{controls} = 907$ $n_{cases} = 110$ | $OR_{smk}$ | 1.00 (Ref) | 0.89 (0.60, 1.32) |
| | $OR_{Y402H}$ | Joint effects | |
| TT | 1.00 (Ref) | 1.00 (Ref) | 0.62 (0.29, 1.33) |
| CT | 1.82 (1.13, 2.92) | 1.52 (0.80, 2.91) | 1.33 (0.69, 2.58) |
| CC | 4.22 (2.39, 7.42) | 2.52 (1.10, 5.79) | 4.16 (1.95, 8.86)) |
| LOC387715 (S69A) $n_{controls} = 995$ $n_{cases} = 120$ | $OR_{smk}$ | 1.00 (Ref) | 0.89 (0.61, 1.30) |
| | $OR_{S69A}$ | Joint effects | |
| GG | 1.00 (Ref) | 1.00 (Ref) | 0.96 (0.55, 1.68) |
| GT | 1.58 (1.05, 2.39) | 1.86 (1.04, 3.31) | 1.28 (0.70, 2.34) |
| TT | 4.75 (2.56, 8.80) | 3.37 (1.32, 8.63) | 6.09 (2.63, 14.14) |

APOE Results: Main effects of the APOE gene in ARM were tested using the CHS data. Neither the distribution of APOE-ε4 carriers (P=0.41) nor APOE-ε2 (P=0.42) carriers was significantly different between cases and controls, when compared to APOE-ε3/ε3.

Meta-Analyses

Figure 12:
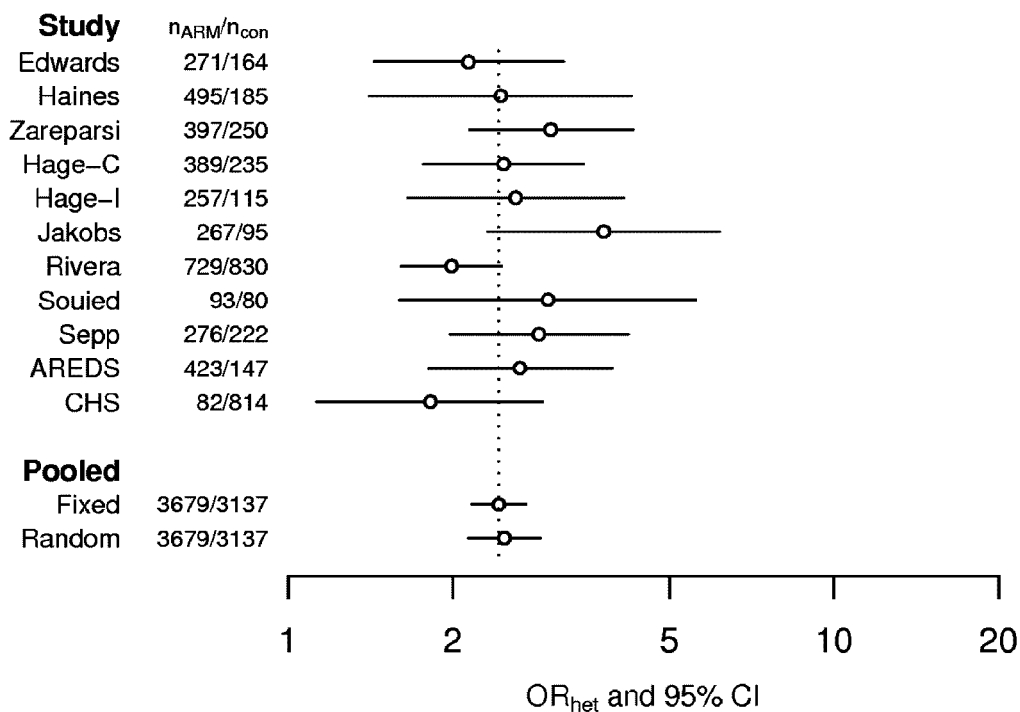
FIG. 12 provides estimated ORs and 95% CIs, derived from data sets included in meta-analysis of Y402H in CFH, and pooled estimates from fixed and random effect models. The top figure shows $OR_{het}$ (OR for CT heterozygotes compared to TT) and the bottom figure shows $OR_{hom}$ (OR for CC homozygotes compared to TT). 'Hage-C' and 'Hage-I' denote estimates derived from the Columbia and Iowa cohorts of Hageman et al. (Hageman, G. S., et al. (2005) A common haplotype in the complement regulatory gene factor H (HF1/CFH) predisposes individuals to age-related macular degeneration. Proc Natl Acad Sci USA. 2005 May 17; 102 (20):7227-32. Epub 2005 May 3), respectively, and 'Jakobs' denotes estimates from the Jakobsdottir et al. paper (Jakobsdottir, J., et al. (2005) Susceptibility genes for age-related maculopathy on chromosome 10q26. Am J Hum Genet. 77, 389-407). "Fixed" denotes pooled estimates derived from all the studies assuming the between study variability is due to chance. 'Random' denotes pooled estimates derived from all the studies allowing for heterogeneity across studies. '$n_{AMD}$' is the total number of ARM cases included in the estimates and '$n_{con}$' is the total number of controls without ARM included in the estimates. The dotted vertical line marks the point estimate of the pooled OR under homogeneity ('Fixed').
Figure 12:
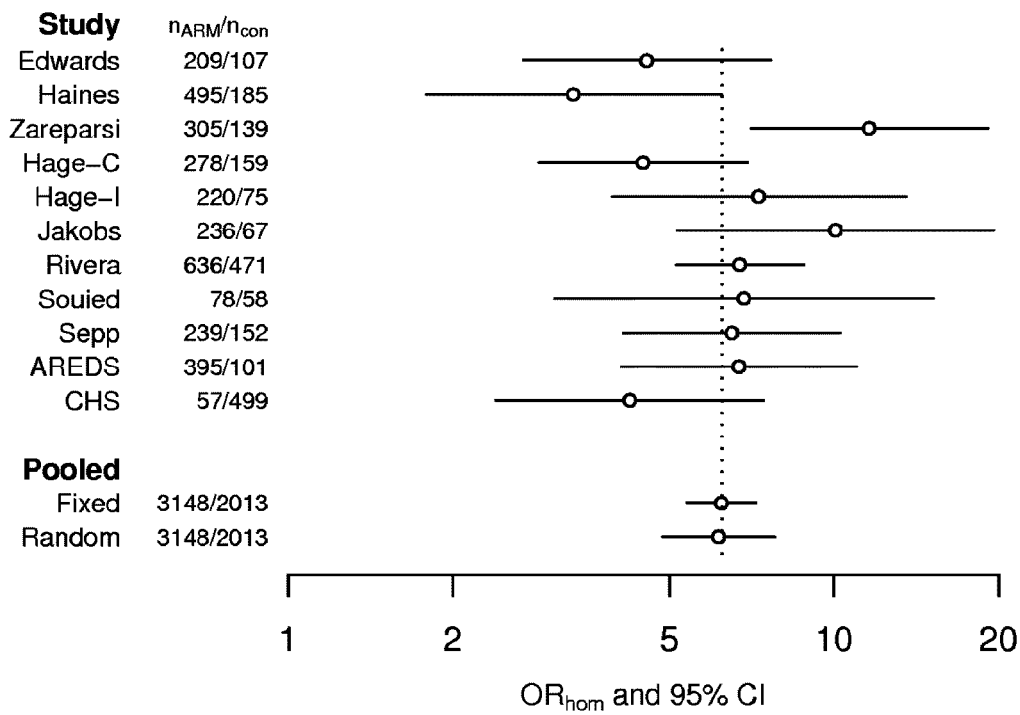

Meta-analysis of CFH: We used a meta-analysis approach to pool estimated ORs for Y402H from eleven independent data sets (including the CHS and AREDS cohorts reported here (Table 14). This resulted in the analysis of 5,451 cases and 3,540 controls all of European or European American descent. The results confirm the increased ARM risk due to the C allele in the non-Hispanic white population (FIG. 12 and Table 22). The pooled estimates have narrower CI than any individual study, and non-overlapping CI for hetero- and homozygote ORs: $OR_{het}$=2.43 (95% CI 2.17-2.72) and $OR_{hom}$=6.22 (95% CI 5.38-7.19), when assuming homogeneity across studies. When the analysis is performed under heterogeneity, the point estimates are essentially the same and the CIs are slightly wider. Leave-one-out sensitivity analysis, under a fixed effect model show that no study has dramatic influence on the pooled estimates (Table 22).

Figure 13:
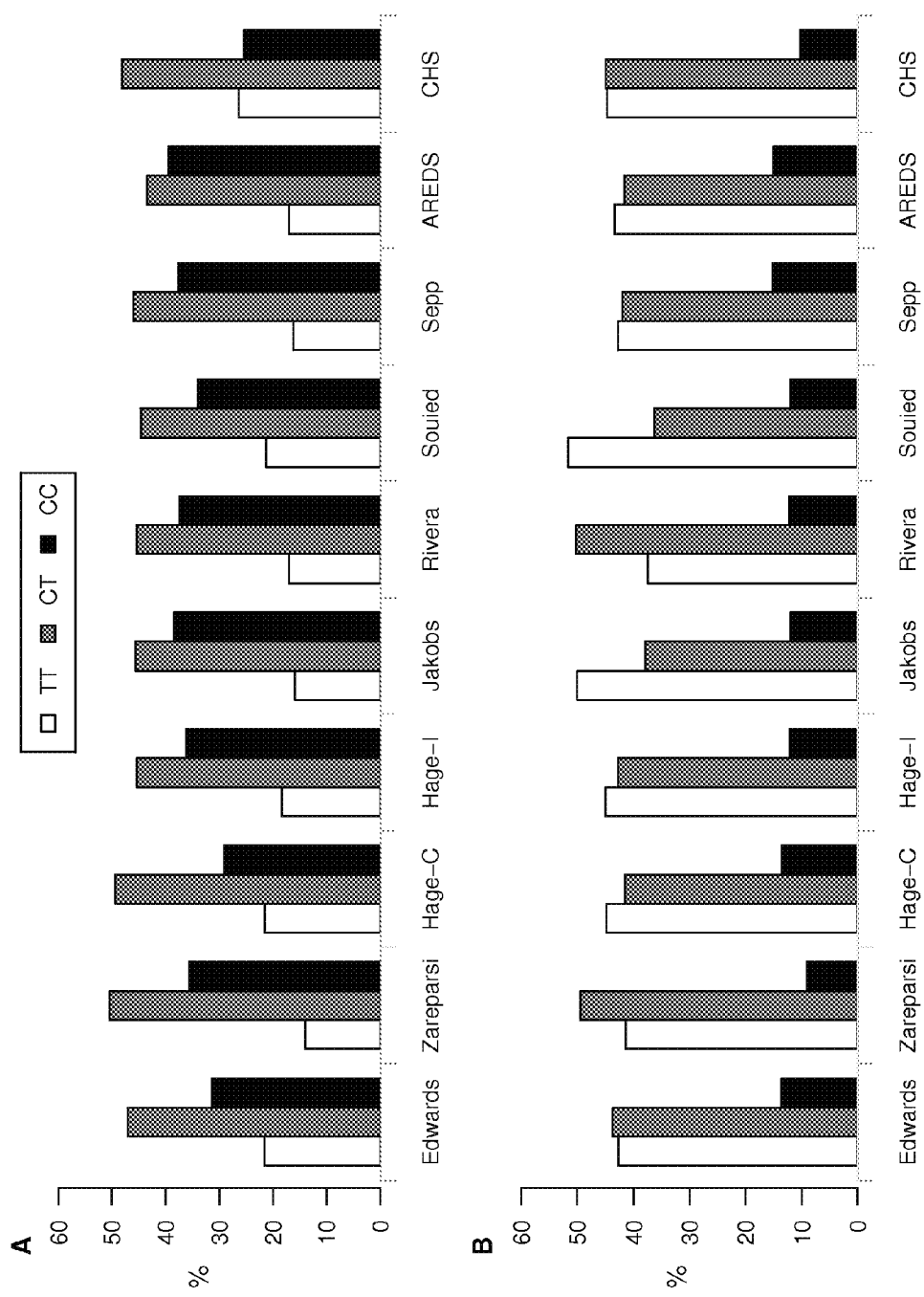
FIG. 13 provides: A: Genotype frequencies (%) in unrelated ARM cases, across cohorts included in meta-analysis of Y402H in CFH. B: Genotype frequencies (%) in unrelated controls without ARM, across studies included in meta-analysis of Y402H in CFH. "Hage-C" and "Hage-I" denote estimates derived from the Columbia and Iowa cohorts of Hageman et al., respectively, and "Jakobs" denotes estimates from the Jakobsdottir et al. paper.

The study by Rivera et al. (2005) changes the estimates more than any other study; when the study is excluded, the $OR_{dom}$ and $OR_{het}$ are lowered by approximately 0.2, while the $OR_{rec}$ and $OR_{hom}$ are approximately 0.2 higher. The Rivera et al. (2005) study is the only study where the genotype distribution, in the control group, deviates from HWE (P=0.03). The allele and genotype distributions, in cases and controls, are strikingly similar across studies. However, the genotype distribution in CHS cases differs from the other studies and the frequency of the TT risk genotype is lower compared to other cohorts (FIG. 13).

TABLE 22

Results of meta-analysis of Y402H in CFH. ORs (95% CIs) estimated from individual studies and all studies pooled. Results of leave-one-out sensitivity analysis are shown.

| | DOMINANCE (CT + CC vs. TT) | RECESSIVE (CC vs. CT + TT) | HETEROZYGOTES (CT vs. TT) | HOMOZYGOTES (CC vs. TT) |
|---|---|---|---|---|
| ORs for | $OR_{dom}$ (95% CI) | $OR_{rec}$ (95% CI) | $OR_{het}$ (95% CI) | $OR_{hom}$ (95% CI) |
| Individual study | | | | |
| Edwards et al. | 2.71 (1.86, 3.94) | 2.89 (1.82, 4.60) | 2.14 (1.44, 3.18) | 4.54 (2.70, 7.65) |
| Haines et al. | — | — | 2.45 (1.41, 4.25) | 3.33 (1.79, 6.20) |
| Zareparsi et al. | 4.36 (3.13, 6.08) | 5.52 (3.54, 8.59) | 3.03 (2.15, 4.28) | 11.61 (7.05, 19.14) |
| Hageman et al. (Columbia) | 2.97 (2.17, 4.07) | 2.61 (1.76, 3.87) | 2.48 (1.77, 3.47) | 4.47 (2.89, 6.93) |
| Hageman et al. (Iowa) | 3.64 (2.38, 5.58) | 4.08 (2.33, 7.16) | 2.61 (1.66, 4.10) | 7.28 (3.92, 13.51) |
| Jakobsdottir et al. | 5.29 (3.35, 8.35) | 4.57 (2.48, 8.42) | 3.78 (2.32, 6.17) | 10.05 (5.16, 19.59) |
| Rivera et al. | 2.92 (2.39, 3.57) | 4.29 (3.42, 5.39) | 1.99 (1.61, 2.46) | 6.72 (5.14, 8.79) |
| Souied et al. | 3.95 (2.22, 7.03) | 3.75 (1.83, 7.71) | 2.99 (1.61, 5.57) | 6.84 (3.07, 15.21) |
| Sepp et al. | 3.85 (2.71, 5.47) | 3.36 (2.28, 4.95) | 2.88 (1.98, 4.20) | 6.49 (4.12, 10.23) |
| AREDS (1 vs. 345) | 3.73 (2.60, 5.34) | 3.69 (2.37, 5.75) | 2.66 (1.81, 3.92) | 6.69 (4.08, 10.98) |
| CHS | 2.26 (1.45, 3.53) | 2.99 (1.85, 4.83) | 1.82 (1.13, 2.92) | 4.22 (2.39, 7.42) |

TABLE 22-continued

Results of meta-analysis of Y402H in CFH. ORs (95% CIs) estimated from individual studies and all studies pooled. Results of leave-one-out sensitivity analysis are shown.

| ORs for | DOMINANCE (CT + CC vs. TT) $OR_{dom}$ (95% CI) | | RECESSIVE (CC vs. CT + TT) $OR_{rec}$ (95% CI) | | HETEROZYGOTES (CT vs. TT) $OR_{het}$ (95% CI) | | HOMOZYGOTES (CC vs. TT) $OR_{hom}$ (95% CI) | |
|---|---|---|---|---|---|---|---|---|
| All studies pooled | | | | | | | | |
| Fixed effects | 3.33 (2.99, 3.71) | $P^a$ 0.11 | 3.75 (3.29, 4.27) | $P^a$ 0.32 | 2.43 (2.17, 2.72) | $P^a$ 0.32 | 6.22 (5.38, 7.19) | $P^a$ 0.05 |
| Random effects | 3.40 (2.88, 4.00) | — | 3.70 (3.09, 4.42) | — | 2.49 (2.14, 2.89) | — | 6.15 (4.86, 7.79) | — |
| Study excluded (Fixed effects) | | | | | | | | |
| Edwards et al. | 3.39 (3.03, 3.80) | $\Delta^b$ −0.06 | 3.83 (3.35, 4.39) | $\Delta^b$ −0.08 | 2.46 (2.19, 2.77) | $\Delta^b$ −0.03 | 6.39 (5.49, 7.42) | $\Delta^b$ −0.17 |
| Haines et al. | — | | — | — | 2.43 (2.17, 2.73) | 0.00 | 6.45 (5.56, 7.48) | −0.23 |
| Zareparsi et al. | 3.22 (2.87, 3.61) | 0.11 | 3.62 (3.16, 4.14) | 0.13 | 2.37 (2.10, 2.67) | 0.06 | 5.88 (5.05, 6.83) | 0.35 |
| Hageman et al. (Columbia) | 3.38 (3.01, 3.79) | −0.05 | 3.92 (3.42, 4.50) | −0.17 | 2.43 (2.15, 2.74) | 0.01 | 6.48 (5.56, 7.55) | −0.26 |
| Hageman et al. (Iowa) | 3.31 (2.96, 3.70) | 0.02 | 3.73 (3.27, 4.26) | 0.02 | 2.42 (2.16, 2.72) | 0.01 | 6.16 (5.31, 7.15) | 0.06 |
| Jakobsdottir et al. | 3.24 (2.89, 3.62) | 0.09 | 3.72 (3.25, 4.24) | 0.03 | 2.37 (2.11, 2.67) | 0.06 | 6.08 (5.24, 7.05) | 0.15 |
| Rivera et al. | 3.51 (3.09, 3.99) | −0.18 | 3.52 (3.00, 4.12) | 0.23 | 2.63 (2.30, 3.00) | −0.20 | 6.03 (5.08, 7.16) | 0.19 |
| Souied et al. | 3.31 (2.96, 3.69) | 0.02 | 3.75 (3.29, 4.28) | 0.00 | 2.42 (2.15, 2.71) | 0.02 | 6.20 (5.35, 7.18) | 0.02 |
| Sepp et al. | 3.28 (2.92, 3.67) | 0.05 | 3.80 (3.31, 4.36) | −0.05 | 2.39 (2.13, 2.69) | 0.04 | 6.19 (5.32, 7.21) | 0.03 |
| AREDS (1 vs. 345) | 3.29 (2.94, 3.68) | 0.04 | 3.76 (3.28, 4.30) | −0.01 | 2.41 (2.14, 2.72) | 0.02 | 6.18 (5.31, 7.19) | 0.04 |
| CHS | 3.41 (3.05, 3.81) | −0.08 | 3.82 (3.34, 4.37) | −0.07 | 2.48 (2.20, 2.78) | −0.04 | 6.39 (5.50, 7.42) | −0.17 |

[a]P-value for test of homogeneity of ORs across studies.
[b]Difference (Δ) of pooled point estimate when a study is excluded from the pooled estimate of all studies (under fixed effects model)

Figure 14:
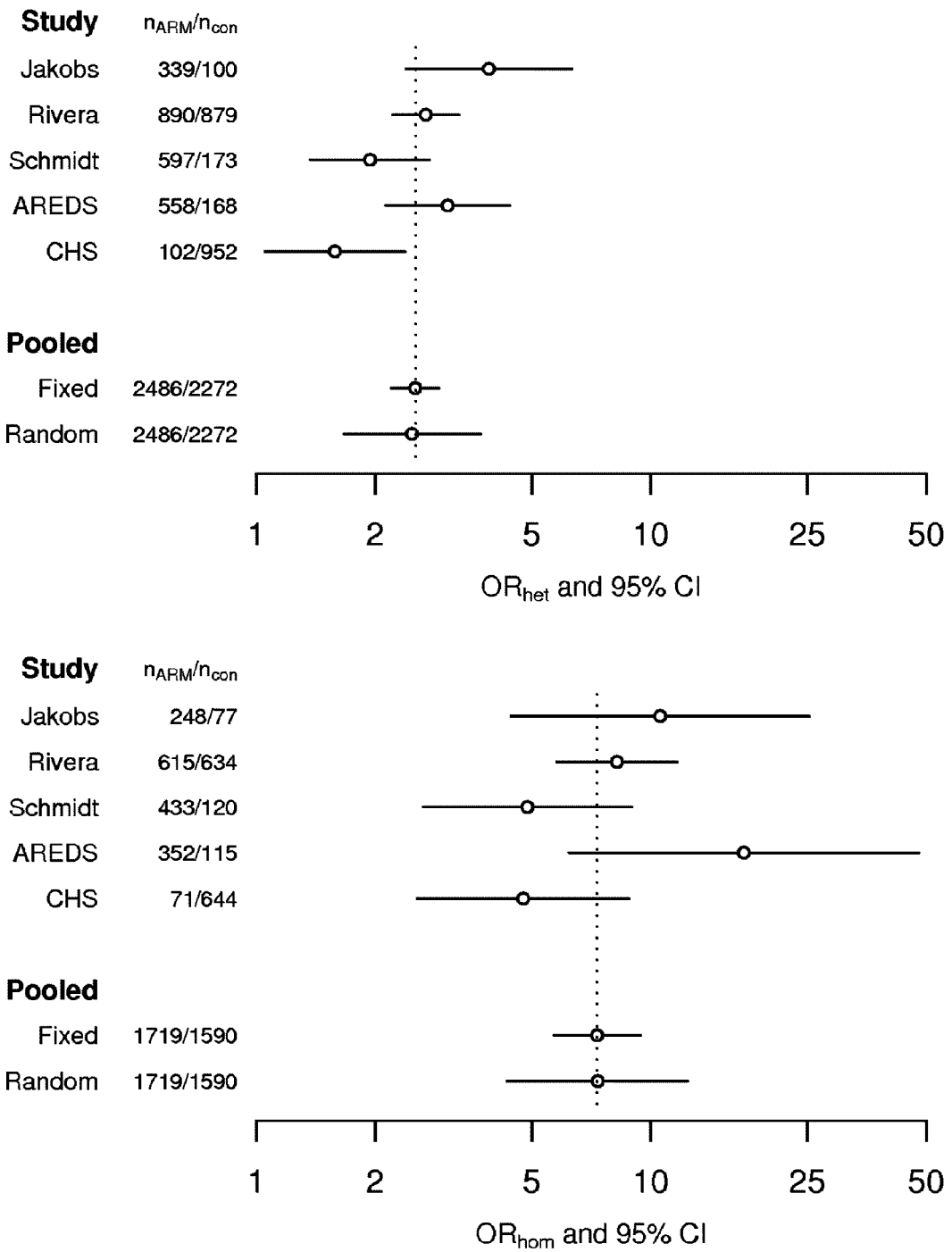
FIG. 14 provides estimated ORs and 95% CIs, derived from data sets included in meta-analysis of S69A in LOC387715, and pooled estimates from fixed and random effect models. The top figure shows $OR_{het}$ (OR for GT heterozygotes compared to GG) and the bottom figure shows $OR_{hom}$ (OR for TT homozygotes compared to GG). "Jakobs" denotes estimates from the Jakobsdottir et al. paper (Jakobsdottir, J., et al. (2005) Susceptibility genes for age-related maculopathy on chromosome 10q26. Am J Hum Genet. 77, 389-407). "Fixed" denotes pooled estimates derived from all the studies assuming the between study variability is due to chance. "Random" denotes pooled estimates derived from all the studies allowing for heterogeneity across studies. "$n_{ARM}$" is the total number of ARM cases included in the estimates and "$n_{con}$" is the total number of controls without ARM included in the estimates. The dotted vertical line marks the point estimate of the pooled OR under homogeneity ('Fixed')
Figure 15:
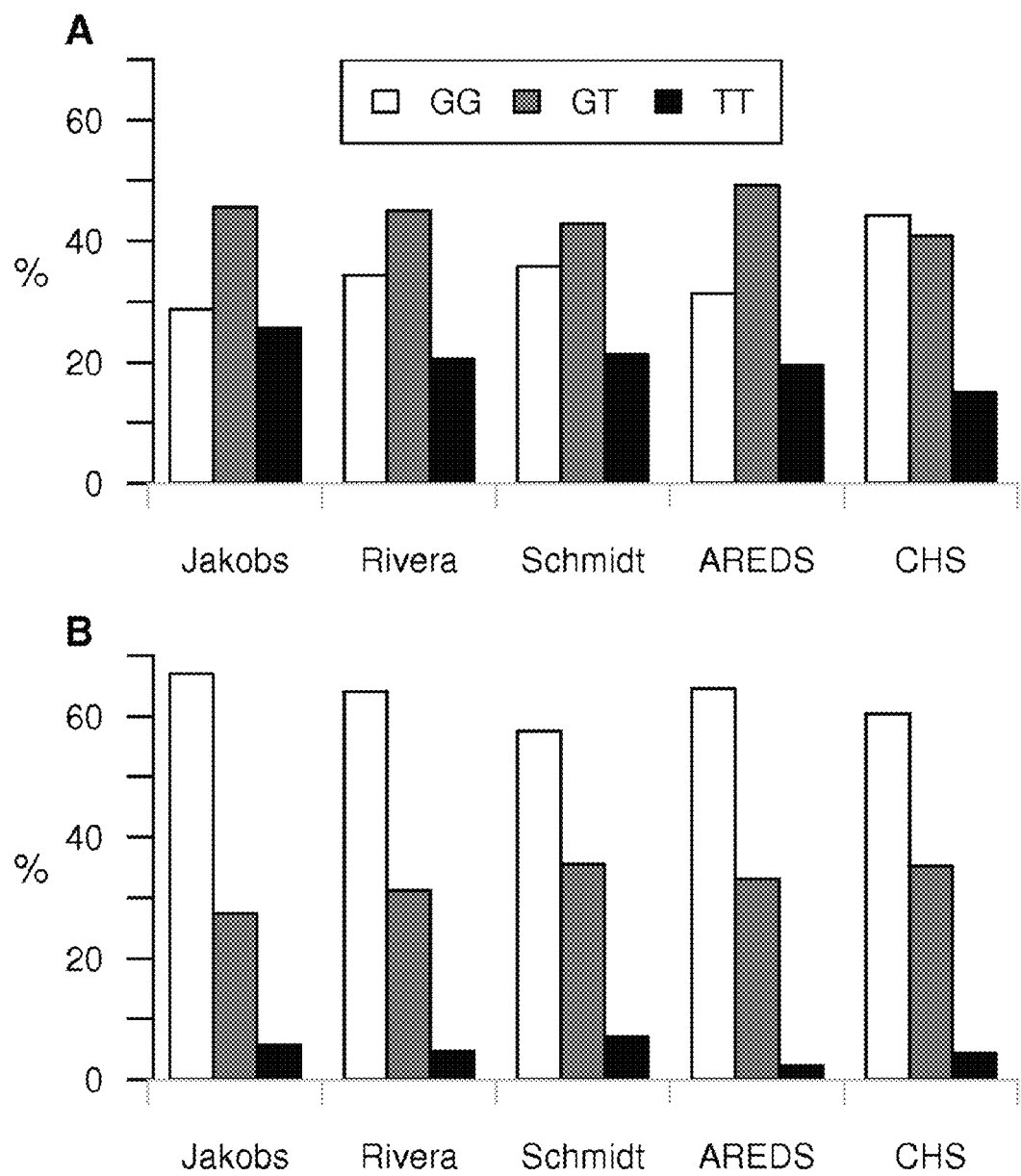
FIG. 15 provides: A: Genotype frequencies (%) in unrelated ARM cases, across cohorts included in meta-analysis of S69A in LOC387715. B: Genotype frequencies (%) in unrelated controls without ARM, across studies included in meta-analysis of S69A in LOC387715. "Jakobs" denotes estimates from the Jakobsdottir et al. paper.

Meta-analysis of LOC387715: Meta-analysis of the risk associated with S69A in ARM included five independent data sets (including the CHS and AREDS cohorts reported here (FIG. 14 and Table 15). This resulted in the analysis of 3,193 cases and 2,405 controls all of European or European American descent. The studies of LOC387715 are more heterogeneous then the studies of CFH; $OR_{dom}$ and $OR_{het}$ differ significantly across studies (P<0.01 and 0.02, respectively). The results support earlier findings of the association of the T allele with increased ARM risk (Table 23). Carriers of two T alleles are at substantially higher risk then are carriers of one T allele; when accounting for between-study variation, the $OR_{het}$ and $OR_{hom}$ are 2.48 (95% CI 1.67-3.70) and 7.33 (95% CI 4.33-12.42), respectively. The genotype distribution is similar across all control populations and across all ARM populations, except the CHS ARM population (FIG. 15).

TABLE 23

Results of meta-analysis of S69A in LOC387715. ORs (95% CIs) estimated from individual studies and all studies pooled. Results of leave-one-out sensitivity analysis are shown.

| OR for | DOMINANCE (GT + TT vs. GG) $OR_{dom}$ (95% CI) | | RECESSIVE (TT vs. GT + GG) $OR_{rec}$ (95% CI) | | HETEROZYGOTES (GT vs. GG) $OR_{het}$ (95% CI) | | HOMOZYGOTES (TT vs. GG) $OR_{hom}$ (95% CI) | |
|---|---|---|---|---|---|---|---|---|
| Individual study | | | | | | | | |
| Jakobsdottir et al. | 5.03 (3.20, 7.91) | | 5.75 (2.46, 13.46) | | 3.89 (2.40, 6.31) | | 10.57 (4.43, 25.22) | |
| Rivera et al. | 3.41 (2.84, 4.09) | | 5.28 (3.76, 7.41) | | 2.69 (2.22, 3.27) | | 8.21 (5.79, 11.65) | |
| Schmidt et al. (1 vs. 345) | 2.42 (1.75, 3.35) | | 3.59 (1.99, 6.47) | | 1.94 (1.37, 2.74) | | 4.87 (2.65, 8.95) | |
| AREDS (1 vs. 345) | 3.99 (2.81, 5.67) | | 10.16 (3.70, 27.88) | | 3.06 (2.13, 4.39) | | 17.26 (6.22, 47.89) | |
| CHS | 1.93 (1.32, 2.83) | | 3.91 (2.17, 7.03) | | 1.58 (1.05, 2.39) | | 4.75 (2.56, 8.80) | |
| All studies pooled | | | | | | | | |
| Fixed effects | 3.19 (2.80, 3.63) | $P^a$ <0.01 | 4.91 (3.85, 6.27) | $P^a$ 0.41 | 2.53 (2.20, 2.90) | $P^a$ 0.02 | 7.32 (5.69, 9.42) | $P^a$ 0.11 |
| Random effects | 3.15 (2.02, 4.90) | — | 4.91 (3.48, 6.94) | — | 2.48 (1.67, 3.70) | — | 7.33 (4.33, 12.42) | — |
| Study excluded (Fixed effects) | | | | | | | | |
| Jakobsdottir et al. | 3.06 (2.67, 3.51) | $\Delta^b$ 0.13 | 4.84 (3.76, 6.24) | $\Delta^b$ 0.07 | 2.43 (2.11, 2.81) | $\Delta^b$ 0.09 | 7.08 (5.44, 9.21) | $\Delta^b$ 0.24 |
| Rivera et al. | 2.98 (2.48, 3.58) | 0.21 | 4.54 (3.20, 6.45) | 0.37 | 2.37 (1.95, 2.88) | 0.16 | 6.48 (4.51, 9.31) | 0.84 |
| Schmidt et al. (1 vs. 345) | 3.36 (2.92, 3.87) | −0.17 | 5.24 (4.01, 6.85) | −0.33 | 2.66 (2.29, 3.08) | −0.13 | 7.97 (6.04, 10.51) | −0.65 |

TABLE 23-continued

Results of meta-analysis of S69A in LOC387715. ORs (95% CIs) estimated from individual studies and all studies pooled. Results of leave-one-out sensitivity analysis are shown.

| OR for | DOMINANCE (GT + TT vs. GG) $OR_{dom}$ (95% CI) | | RECESSIVE (TT vs. GT + GG) $OR_{rec}$ (95% CI) | | HETEROZYGOTES (GT vs. GG) $OR_{het}$ (95% CI) | | HOMOZYGOTES (TT vs. GG) $OR_{hom}$ (95% CI) | |
|---|---|---|---|---|---|---|---|---|
| AREDS (1 vs. 345) | 3.08 (2.68, 3.54) | 0.11 | 4.70 (3.65, 6.04) | 0.22 | 2.45 (2.11, 2.84) | 0.08 | 6.93 (5.34, 8.98) | 0.40 |
| CHS | 3.41 (2.97, 3.91) | −0.22 | 5.15 (3.94, 6.73) | −0.24 | 2.68 (2.32, 3.10) | −0.15 | 7.99 (6.06, 10.52) | −0.66 |

[a]P-value for test of homogeneity of ORs across studies.
[b]Difference (Δ) of pooled point estimate when a study is excluded from the pooled estimate of all studies (under fixed effects model)

Major discoveries of associations of the CFH and PLEKHA1/LOC387715 genes with ARM have been published after the findings of Example 1. A number of reports established a strong association of the Y402H coding change in CFH with ARM and three reports found association with ARM of the S69A coding change in LOC387715 that was of similar magnitude as the association of Y402H. Both of those genes lie within chromosomal regions, CFH on 1q31 and LOC387715 on 10q26, consistently identified by family-based linkage studies (Seddon, J. M., et al. (2003); Majewski, J., et al. (2003); Iyengar, S. K., et al. (2004); Weeks, D. E., et al. (2001) Age-related maculopathy: an expanded genome-wide scan with evidence of susceptibility loci within the 1q31 and 17q25 regions. Am J Ophthalmol. 132, 682-692; Weeks, D. E., et al. (2004); Klein, M. L., et al. (1998); and Kenealy, S. J., et al. (2004)).

Because the majority of the studies of Y402H and all three studies of S69A were specially designed to search for (and find) genes involved in ARM complex etiology, it is possible that they overestimate the effect size of the risk alleles at Y402H and S69A. Therefore, two independent case-control cohorts were analyzed with minimal inclusion and exclusion criterion based on ARM status, the AREDS and CHS cohorts. The AREDS cohort did have health-related inclusion and exclusion criterion including criterion based on eye disease status; however, both affected and non-affected individuals were enrolled (Age-Related Eye Disease Study Research Group (1999) The Age-Related Eye Disease Study (AREDS): design implications. AREDS report no. 1. Control Clin Trials. 20, 573-600). The CHS cohort is a population-based cohort that utilized community-based recruitment of individuals 65 years and older with minimal inclusion and exclusion criteria (Fried et al. (1991)). Retinal assessments were conducted during the eighth year follow-up visit and retinal diseases were not a factor for recruitment. Given the difference in ascertainment of subjects into the two studies, replication of association of a candidate gene in both cohorts greatly strengthens the support for its causal involvement in ARM pathogenesis.

We evaluated associations of four genes, CFH (1q31), ELOVL4 (6q14), PLEKAH1 (10q26), and LOC387715 (10q26). Both CFH and LOC387715 are extremely significantly (P≦0.00001) associated with ARM in both AREDS and CHS cohorts. Both genes show an allele-dose effect on the ARM risk and a model of independent multiplicative contribution of the two genes is most parsimonious in both AREDS and CHS cohorts. The A320T coding change in the PLEKHA1 gene, adjacent to and in linkage disequilibrium with LOC387715 on 10q26, is significantly associated with ARM in the AREDS cohort (P=0.00004) but not in the CHS cohort (P=0.08). These results based on applying the haplotype method to both the AREDS and CHS cohorts, combined with the findings of Rivera et al. (2005), who used conditional haplotype analysis and detected, for the first time, a weak expression of LOC387715 in the retina, and Schmidt et al. (2006), who detected only a weak association signal at PLEKHA1, strongly indicate that S69A in LOC387715 is a major ARM-predisposing variant on 10q26. The results of the haplotype method show that PLEKHA1 may not be sufficient to account for the ARM-predisposition at 10q26; however A320T in PLEKHA1 cannot be excluded as a causative haplotype with S69A and other unknown variants.

The replication of associations of CFH and LOC387715 genes with ARM in AREDS and CHS cohorts, two cohorts with different ascertainment schemes, continues to provide strong support for their involvement in ARM. Variable findings for PLEKHA1 in AREDS and CHS cohorts do however need to be considered in the light of differences between the two cohorts. In addition to differences in ascertainment of the case and control populations, the evaluation of retinal changes, documentation of retinal findings, and prevalence of advanced ARM differed between the two cohorts. In the CHS study, fundus photography was only available for one randomly selected eye and the photography was performed with non dilated pupils and these limitations could certainly influence the sensitivity to detect disease pathology, although this is more likely to influence the detection of early retinal changes. The proportion of advanced ARM in the entire CHS cohort that was evaluated at the 8 year follow up evaluation was approximately 1.3% (Klein, R., Klein, B. E., Marino, E. K., Kuller, L. H., Furberg, C., Burke, G. L. and Hubbard, L. D. (2003) Early age-related maculopathy in the cardiovascular health study. Ophthalmology. 110, 25-33) compared to approximately 17% in the AREDS (Age-Related Eye Disease Study Research Group (2000)) and the variation in the proportion of advanced ARM disease pathology between the two cohorts could lead to variation in findings, especially if a gene is more likely to influence progression of the disease. Additionally, one important difference between these two cohorts is the timing of the retinal evaluations. AREDS participants had retinal evaluations conducted at baseline as well as during follow-up evaluations, while CHS participants had retinal evaluations done 8 or more years after enrollment, when they would have been at least 73 years old. It is possible that survival to the retinal evaluation for the CHS participants could bias the population available for this particular type of study. It also should be noted that in the AREDS cohort, subjects in categories other than the unaffected group were randomized into a clinical trial using vitamin and mineral supplements to evaluate the impact of these on ARM progression. The effect of this is not clear.

As mentioned previously, most studies that have investigated the genetic etiology of ARM were designed to optimize identification of regions of the genome housing susceptibility genes for ARM and for ARM candidate gene testing. Utilizing these retrospective studies to estimate attributable risk may lead to overestimates. Published attributable risks range from 43% to 68% (Edwards et al. (2005); Haines et al. (2005); Jakobsdottir (2005); and Schmidt et al. (2006)) for the Y402H variant in CFH and from 36% to 57% (Jakobsdottir (2005) and Schmidt et al. (2006)) for the S69A variant in LOC387715. Interestingly, the adjusted population attributable risks (PARs) for the CHS population are lower than those previously published: 38% for the Y402H variant in CFH and 25% for the S69A variant in LOC387715 (Table 13). Because the majority of the CHS cases have moderate ARM the PAR estimates derived from the CHS data are not completely comparable to estimates from previous studies where the proportion of patients with advanced ARM was considerably higher. However, they are comparable to estimates derived from using AREDS cases of grade 3. Those estimates are within in the previously published range of PARs: 49% for Y402H in CFH and 46% for S69A in LOC387715. These findings may indicate that the risk of ARM attributed to these two susceptibility variants may be lower than previously thought given that the CHS cohort was not ascertained based on ARM status. A prospective design is needed to more precisely estimate the relative risks, which are approximated by ORs estimated from retrospective case-control designs, and corresponding PARs.

We were not able to replicate the association of ELOVL4 with overall ARM (Conley et al. (2005)). The number of individuals with exudative ARM allowed us to perform subphenotype analysis in the AREDS but not the CHS cohort. Subphenotype analysis was especially important with regard to ELOVL4, where our previous findings indicated a role for ELOVL4 in exudative ARM; this is (weakly) supported in the AREDS cohort. Given the lack of strong association and significant ORs for ELOVL4 in ARM susceptibility in both cohorts and the lack of association reported by Ayyagari et al., it is very unlikely that ELOVL4 plays a substantial role in ARM susceptibility. The power to detect an OR of 0.6 for overall ARM is reasonable, with type I error rate 5%, minor allele frequency 0.15, and population prevalence 6% the power is ~81% in AREDS and ~69% in CHS. The power to detect the same effect in exudative ARM is only ~53% in AREDS data, under the same conditions. Therefore the possibility that ELOVL4 plays a role in overall ARM is unlikely but mild effect in exudative ARM cannot be refuted. These power estimates were performed using QUANTO (Gauderman, W. J. and Morrison, J. M. (2006) QUANTO 1.1: A computer program for power and sample size calculations for genetic-epidemiology studies).

The AREDS and CHS data support the independent contribution of Y402H in CFH and S69A in LOC387715 to ARM susceptibility. A multiplicative risk model for these two variants is the most parsimonious based on evaluation of the AREDS and CHS cohorts; this model was also supported by our previous paper Jakobsdottir et al. (2005) as well as data presented by Rivera et al. (2005) and Schmidt et al. (2006a). The ARM risk appears to increase as the total number of risk alleles at Y402H and S69A increases (Table 20).

Prior to the discovery of CFH and LOC387715 cigarette smoking was one of the more important known ARM-related risk factors. Cigarette smoking is generally accepted as a modifiable risk factor for ARM; van Leeuwen et al. provide a review of the epidemiology of ARM and discuss the support of smoking as ARM risk factor (van Leeuwen, R., Klaver, C. C., Vingerling, J. R., Hofman, A. and de Jong, P. T. (2003) Epidemiology of age-related maculopathy: a review. Eur J Epidemiol. 18, 845-854). Schmidt et al. (2006) recently reported statistically significant interaction between LOC387715 and cigarette smoking in ARM. Their data suggested that the association of LOC387715 with ARM was primarily driven by the gene effect in heavy smokers. Our own analyses of interaction do not support this finding and the AREDS data suggest that the joint action of S69A and smoking is multiplicative.

A role for CFH and LOC387715 in ARM susceptibility is further supported via the results of our meta-analysis. The meta-analysis, which include the CHS and AREDS cohorts reported in this paper, indicates that having one or two copies of the risk allele at CFH or LOC387715 increases the risk of ARM, and with those who have two copies are at higher risk. The combined results from all studies as well as the results from each independent study were remarkably tight (FIGS. 12 and 14). One known limitation of meta-analysis is the susceptibility to publication bias. Generally, such bias is a result of non-publication of negative findings (Normand, S. L. (1999) Meta-analysis: formulating, evaluating, combining, and reporting. Stat Med. 18, 321-359). In the case of CFH and LOC387715, all published studies have reported strong association with ARM in the same direction with the risk allele for CFH being the allele that codes for histidine and the risk allele for LOC387715 being the allele that codes for serine. Preferential publication of statistically significant associations were expected to show random directionality if the significant association is a false-positive result (Lohmueller, K. E., Pearce, C. L., Pike, M., Lander, E. S. and Hirschhorn, J. N. (2003) Meta-analysis of genetic association studies supports a contribution of common variants to susceptibility to common disease. Nat Genet. 33, 177-182). It is therefore unlikely that the consistency of the association of CFH and LOC387715 with ARM is a result of publication bias.

While the results of our statistical analyses are in agreement with LOC387715 being the major ARM-related gene on 10q26, they do not prove causality. The possible causal role of CFH in ARM pathogenesis has been further supported by the localization of its protein within drusen deposits of ARM patients and involvement in activation of the complement pathway. Regarding LOC387715, little is currently known about the biology of the gene and nothing about how its protein may affect ARM susceptibility. Until recently the expression of LOC387715 appeared limited to the placenta but recently weak expression was reported in the retina (Rivera et al. (2005)), which opens up the possibility of a tissue-specific role of the gene.

In summary, the results presented in this Example continue to support a role of both CFH and LOC387715 in etiology of ARM, given that both genes are highly associated with ARM regardless of how the subjects were ascertained. Evaluation of PLEKHA1 and ELOVL4 in the AREDS and CHS cohorts demonstrates that these genes are much less likely to play role in ARM susceptibility. The CFH and LOC387715 genes appear to act independently in a multiplicative way in ARM pathogenesis and individuals homozygote for the risk alleles at either locus are at highest risk.

Having described this invention above, it will be understood to those of ordinary skill in the art that the same can be performed within a wide and equivalent range of conditions, formulations and other parameters without affecting the scope of the invention or any embodiment thereof.

We claim:

1. A method of determining risk of developing severe Age-Related Maculopathy in a human subject comprising detecting the presence of a thymine or guanine at base 270 of SEQ ID NO: 20 (rs 10490924) from a sample obtained from the subject, wherein the presence of thymine for one or both alleles indicates increased risk of developing severe Age-Related Maculopathy and the presence of guanine for both alleles indicates decreased risk of developing severe Age-Related Maculopathy.

2. The method of claim 1 further comprising examining one or more allelic variations in one or more of PLEKHAI, PRSS11 and LOC387715.

3. The method of claim 1 in which the patient has one or more symptoms of Age-related Maculopathy and the presence of thymine—for one or both alleles indicates increased risk of developing end-stage Age-Related Maculopathy and the presence of guanine for both alleles indicates decreased risk of developing end-stage Age-Related Maculopathy.

4. The method of claim 3 in which the patient has one or more symptoms of Age-related Maculopathy and the presence of thymine for one or both alleles indicates increased risk of developing one or both of geographic atrophy and choroidal neovascular membranes and the presence of guanine for both alleles indicates decreased risk of developing one or both of geographic atrophy and choroidal neovascular membranes.

5. The method of claim 1 in which the presence of thymine for one or both alleles indicates increased risk of developing end-stage Age-Related Maculopathy and the presence of guanine for both alleles indicates decreased risk of developing end-stage Age-Related Maculopathy.

6. The method of claim 5 in which the presence of thymine for one or both alleles indicates increased risk of developing one or both of geographic atrophy and choroidal neovascular membranes and the presence of guanine for both alleles indicates decreased risk of developing one or both of geographic atrophy and choroidal neovascular membranes.

* * * * *

UNITED STATES PATENT AND TRADEMARK OFFICE
CERTIFICATE OF CORRECTION

| | | |
|---|---|---|
| PATENT NO. | : 8,053,190 B2 | Page 1 of 1 |
| APPLICATION NO. | : 12/701098 | |
| DATED | : November 8, 2011 | |
| INVENTOR(S) | : Michael B. Gorin et al. | |

It is certified that error appears in the above-identified patent and that said Letters Patent is hereby corrected as shown below:

Title Page of Patent, Column 2, OTHER PUBLICATIONS, Line 15, delete "366,1121" and insert -- 366, 1121 --

Title Page of Patent, Column 2, OTHER PUBLICATIONS, Line 38, delete "http://hydra.usc.edu/gxe)." and insert -- http://hydra.usc.edu/gxe. --

Column 71, Line 51, Claim 2, delete "PLEKHAI" and insert -- PLEKHA1 --

Column 71, Line 54, Claim 3, "thymine—for" should read -- thymine for --

Signed and Sealed this
Eighth Day of May, 2012

David J. Kappos
*Director of the United States Patent and Trademark Office*